US011166983B2

(12) United States Patent
Anjos et al.

(10) Patent No.: US 11,166,983 B2
(45) Date of Patent: Nov. 9, 2021

(54) METHODS FOR THE PRODUCTION OF TCRγδ+ T CELLS

(71) Applicant: LYMPHACT—LYMPHOCYTE ACTIVATION TECHNOLOGIES, S.A., Cantanhede (PT)

(72) Inventors: Diogo Antonio Remechido Anjos, Cantanhede (PT); Daniel Vargas Correia, Cantanhede (PT); Anfonso Rocha Martins De Almeida, Cantanhede (PT)

(73) Assignee: LYMPHACT—LYMPHOCYTE ACTIVATION TECHNOLOGIES, S.A., Cantanhede (PT)

( * ) Notice: Subject to any disclaimer, the term of this patent is extended or adjusted under 35 U.S.C. 154(b) by 598 days.

(21) Appl. No.: 15/735,371

(22) PCT Filed: Jun. 8, 2016

(86) PCT No.: PCT/EP2016/063077
§ 371 (c)(1),
(2) Date: Dec. 11, 2017

(87) PCT Pub. No.: WO2016/198480
PCT Pub. Date: Dec. 15, 2016

(65) Prior Publication Data
US 2018/0169147 A1    Jun. 21, 2018

(30) Foreign Application Priority Data

Jun. 9, 2015   (PT) .......................... 20151000047568
May 12, 2016  (PT) .......................... 20161000032002

(51) Int. Cl.
*C12N 5/0783*   (2010.01)
*A61K 35/17*    (2015.01)
*A61K 39/00*    (2006.01)

(52) U.S. Cl.
CPC ............ *A61K 35/17* (2013.01); *C12N 5/0638* (2013.01); *A61K 2039/5158* (2013.01); *C12N 2501/2301* (2013.01); *C12N 2501/2302* (2013.01); *C12N 2501/2304* (2013.01); *C12N 2501/2307* (2013.01); *C12N 2501/2315* (2013.01); *C12N 2501/2321* (2013.01); *C12N 2501/24* (2013.01); *C12N 2501/515* (2013.01); *C12N 2501/599* (2013.01)

(58) Field of Classification Search
CPC ............ A61K 35/17; C12N 2501/2304; C12N 2501/2315
See application file for complete search history.

(56) References Cited

U.S. PATENT DOCUMENTS

| 6,537,812 B1 * | 3/2003 | Bell ........................ A61P 35/00 435/405 |
| 2003/0157060 A1 | 8/2003 | Bell et al. |
| 2009/0098095 A1 * | 4/2009 | Zhang ..................... A61P 35/00 424/93.71 |
| 2014/0141513 A1 | 5/2014 | De Carvalho Silva Santos et al. |

FOREIGN PATENT DOCUMENTS

| CN | 106399245 A  * | 2/2017 |
| WO | 2000/026347 A1 | 5/2000 |
| WO | 2001/75072 A2 | 10/2001 |
| WO | 2015/061694 A2 | 4/2015 |

OTHER PUBLICATIONS

International Search Report dated Aug. 10, 2016, from International Application No. PCT/EP2016/063077, 4 pages.
Ribot, J.C. et al. "Human Vδ Thymocytes Are Functionally Immature and Differentiate into Cytotoxic Type 1 Effector T Cells upon IL-2/IL-15 Signaling", The Journal of Immunology, vol. 192, No. 5, Mar. 1, 2014, pp. 2237-2243.
Wu, D. et al. "Ex vivo expanded human circulating Vδ1 VδT cells exhibit favorable therapeutic potential for colon cancer", Oncoimmunology, vol. 4, No. 3, Mar. 4, 2015.
Fisher, J. et al. "Neuroblastoma Killing Properties of Vδ2 and Vδ2-Negative VδT Cells Following Expansion by Artificial Antigen-Presenting Cells", Clinical Cancer Research, vol. 20, No. 22, Jun. 3, 2014, pp. 5720-5732.
Vermijlen, D. et al. "Distinct Cytokine-Driven Responses of Activated Blood Vδ T Cells: Insights into Unconventional T Cell Pleiotropy", The Journal of Immunology, vol. 178, No. 1, Apr. 1, 2007, pp. 4304-4314.
Siegers, G.M. et al. "Human Vδ1 Vδ T cells expanded from peripheral blood exhibit specific cytotoxicity against B-cell chronic lymphocytic leukemia-derived cells", Cytotherapy, Isis Medical Media, vol. 13, No. 6, Jul. 1, 2011, pp. 753-764.

\* cited by examiner

*Primary Examiner* — Daniel C Gamett
(74) *Attorney, Agent, or Firm* — Meunier Carlin & Curfman LLC

(57) ABSTRACT

The present invention relates to novel methods for the isolation and the selective ex vivo expansion of Vδ2⁻ TCRγδ+T cells and to their clinical application.

18 Claims, 17 Drawing Sheets

Figure 1:
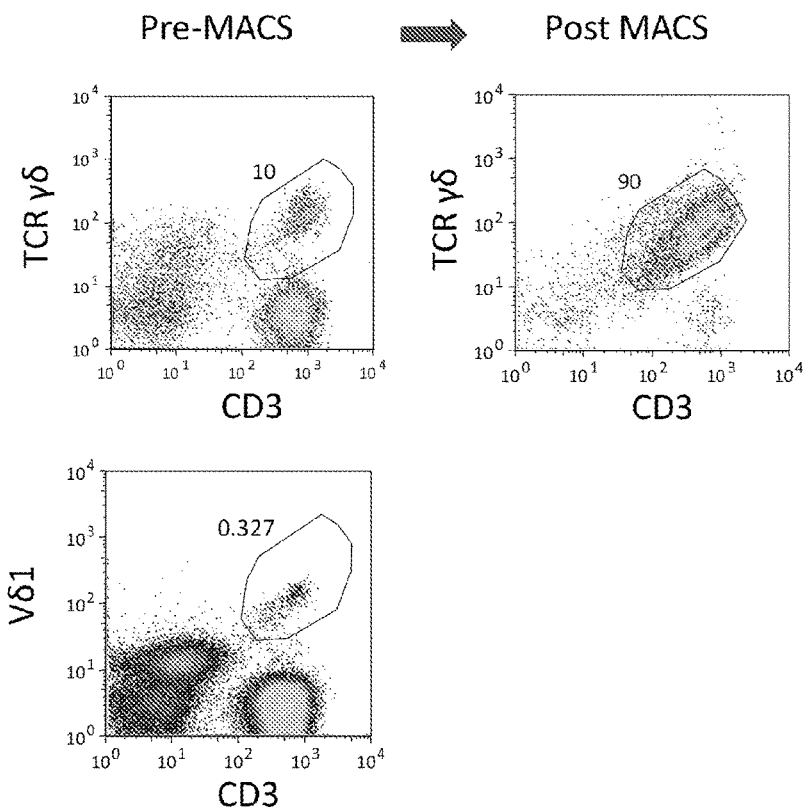

FIG. 3A, FIG. 3B, and FIG. 3C
A
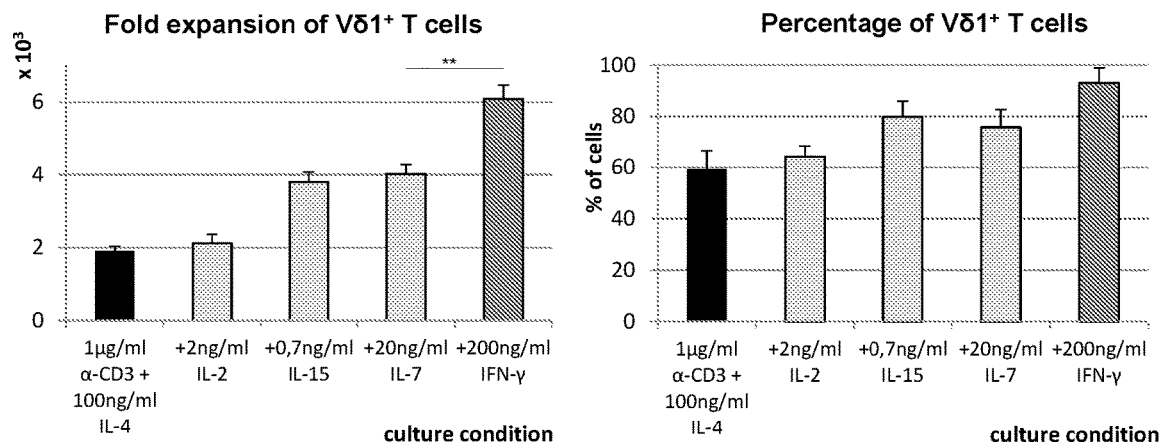
B
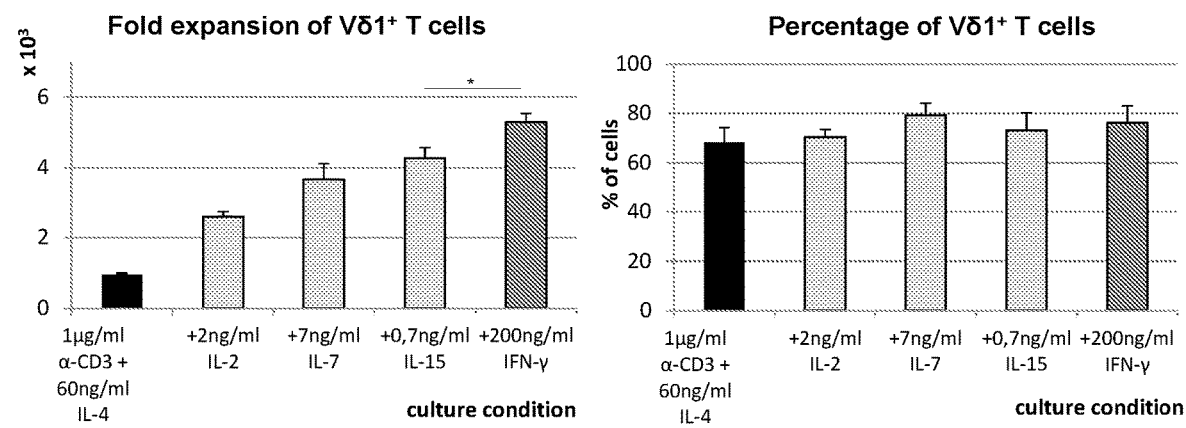
C
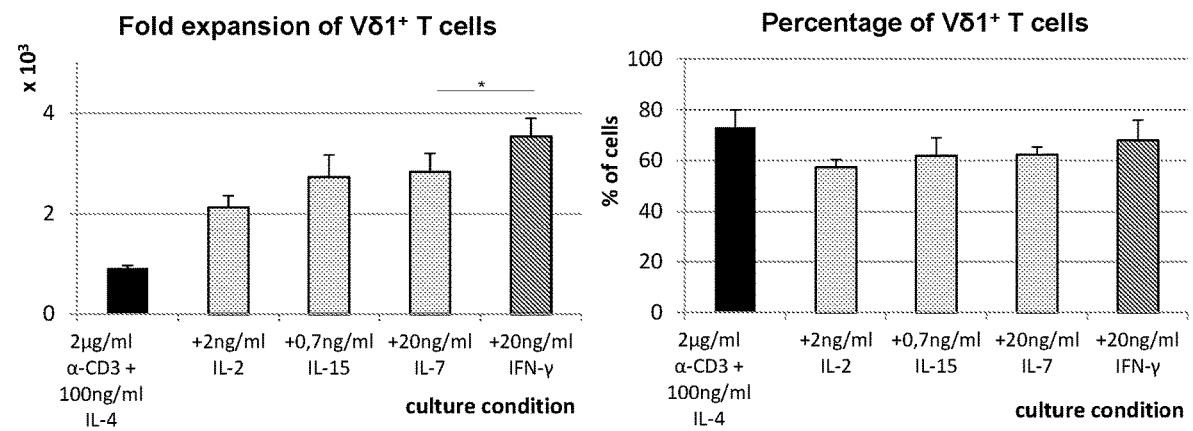

FIG. 8A, FIG. 8B, and FIG. 8C
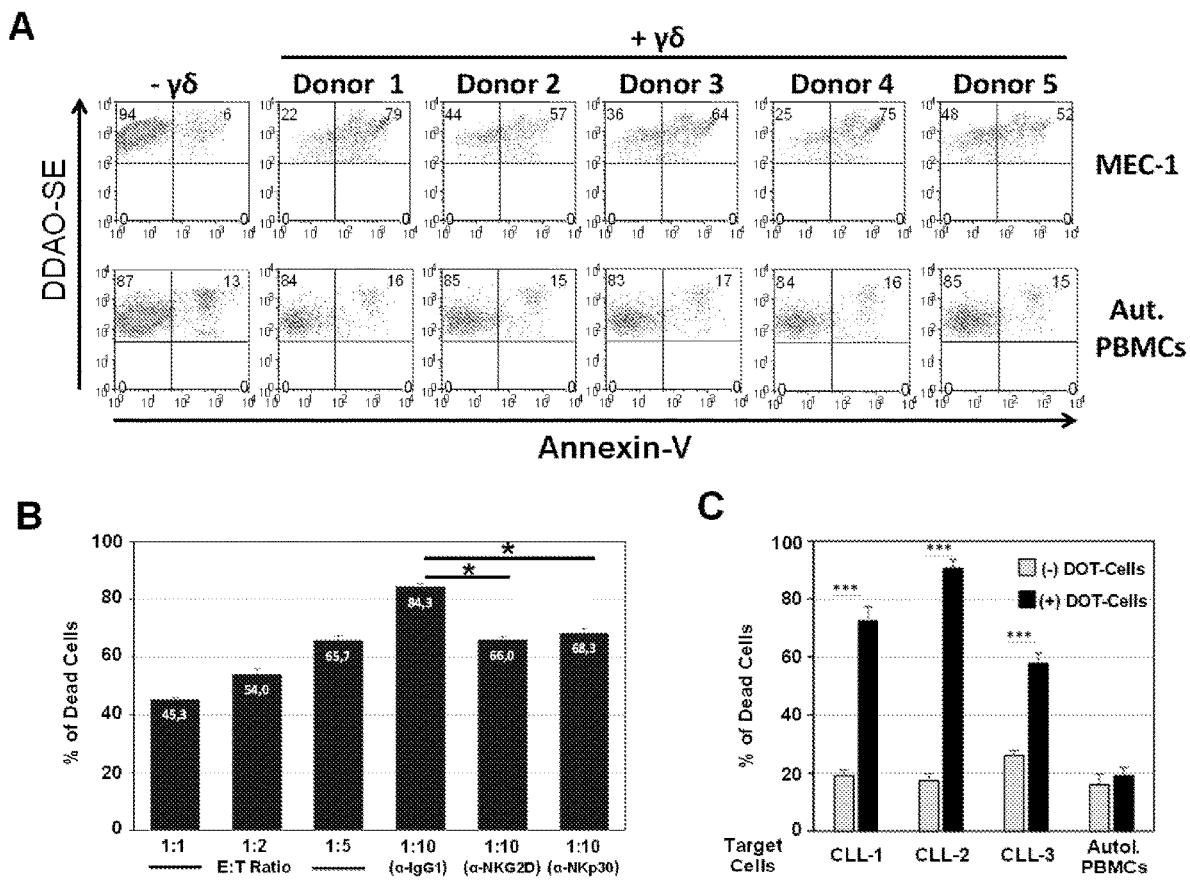
FIG. 9
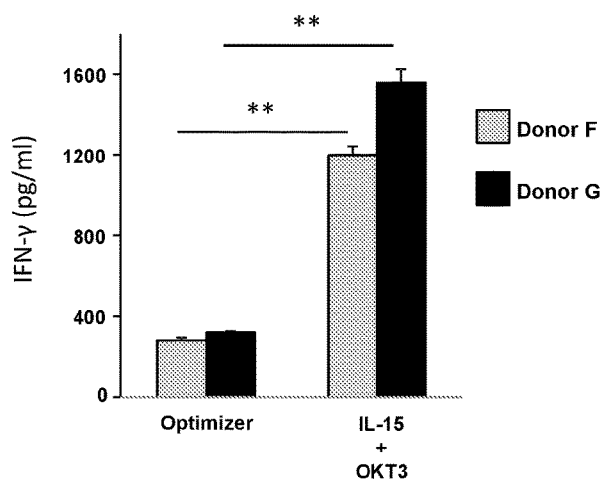

A

B

C

D

■ with tumor cell invasion
□ no tumor cell invasion
n, number of mice

METHODS FOR THE PRODUCTION OF TCRγδ+ T CELLS

FIELD OF THE INVENTION

The present invention relates to novel methods for the isolation and the selective ex vivo expansion of Vδ2⁻ TCRγδ⁺ T cells and to their clinical application.

BACKGROUND TO THE INVENTION

TCRγδ⁺ T Cells

The immune system of jawed vertebrates includes various lymphocyte populations capable of recognizing and eliminating tumor cells, which constitutes the basis of cancer immunotherapy. One population is characterized by the expression of a T-cell receptor (TCR) formed by the junction of a gamma (γ) chain and a delta (δ) chain. TCRγδ⁺ T cells (here also designated as γδ T cells) account for 1-10% of human peripheral blood lymphocytes (PBLs) but are substantially enriched in epithelial tissues of healthy individuals, where they reach up to 50% of T cells.[1] TCRγδ⁺ T cells have potent Major Histocompatibility Complex (MHC)-unrestricted cytotoxicity against malignant and infected cells, while leaving unharmed healthy cells and tissues. Therefore, they are usually considered a first-line surveillance mechanism against infection and tumors.[1]

In humans, different subsets or subpopulations of TCRγδ⁺ T cells are identified and classified based on the genes that encode their δ chain. Around 60-95% of TCRγδ⁺ T cells in the peripheral blood express the Vδ2 chain in association with Vγ9 chain, while most of the remainder TCRγδ⁺ T cells express the Vδ1 chain in association with various Vγ elements: Vγ2, Vγ3, Vγ4, Vγ5 or Vγ8. Other (rarer) human TCRγδ⁺ T cell populations express Vδ3, Vδ5, Vδ6, Vδ7 and Vδ8 chains.[2-4]

Vδ2⁺ TCRγδ⁺ T Cells

Current adoptive immunotherapy approaches based on TCRγδ⁺ T cells are limited to the Vδ2⁺ TCRγδ⁺ T cell subpopulation (here also designated as Vδ2⁺ T cells).[5,6] Most Vδ2⁺ T cells specifically respond to nonpeptide alkylphosphates such as isopentenyl pyrophosphate (IPP), which is produced at abnormal levels in tumor cells and in individuals exposed to bone-strengthening aminobisphosphonates, such as zoledronate and pamidronate. These compounds, when combined with interleukin-2, stimulate the proliferation and anti-tumour cytotoxic function of Vδ2⁺ T cells in vitro, and generate purified cell populations for clinical applications.[5-7] However, the clinical trials completed to date have shown a low percentage of objective responses in cancer patients.[8] Thus, current γδ T cell-based treatments, although feasible and safe, have obvious limitations.[6]

Vδ1⁺ TCRγδ⁺ T Cells

Human Vδ1⁺ TCRγδ⁺ T cells (here also designated as Vδ1⁺ T cells), constitute 1-40% of all TCRγδ⁺ PBLs but are the major γδ T cell population at epithelial sites, such as the intestine and the skin. While it has never been evaluated in clinical trials, this cell subset can also display strong anti-tumor activity. Vδ1⁺ T cells infiltrating skin, colon, kidney and lung tumours were cytotoxic against both autologous and allogeneic cancer cells.[9-13] An interesting correlation was also found between the increase in number of donor-derived peripheral blood Vδ1⁺ T cells and improved 5-10-year disease-free survival following bone marrow transplantation for acute lymphoblastic leukaemia (ALL).[14] Importantly, the infused Vδ1⁺ T cells persisted in these patients for several years.[14,15] In another setting, low-grade non-Hodgkin lymphoma patients with high Vδ1⁺ T cell counts experienced stable disease at 1 year follow-up, an improved clinical course compared to those with a lower number of Vδ1⁺ T cells.[18] Circulating Vδ1⁺ T cells are also typically increased in chronic lymphocytic leukemia (CLL) patients[17] and have been associated with non-progression in low risk B-CLL patients.[18] Finally, quantitative increases in circulating Vδ1⁺ T cells were also observed in human immunodeficiency virus (HIV)[19] and malaria[20] infections, as well as in human cytomegalovirus (HCMV) infections following renal transplantation.[4,21] In different circumstances, however, subpopulations of Vδ1⁺ T cells can exhibit immunosuppressive and regulatory properties, a function that can also be exploited for therapeutic purposes.[22]

A small number of methods to specifically expand Vδ1⁺ T cells in vitro have been described, although none of them could be adapted for clinical applications (reviewed in Siegers, G. et al., 2014, ref.[22]). Meeh et al. first showed that Vδ1⁺ T cells from healthy donors could expand ex vivo in response to ALL leukemic blasts.[23] Knight, A. and colleagues and Merims, S. and colleagues isolated peripheral blood Vδ1⁺ T cells and treated them in the presence of phytohemagglutinin (PHA) or anti-CD3 monoclonal antibody (mAb), IL-2 and irradiated allogeneic peripheral blood mononuclear cells (PBMCs), for 3 weeks.[24,25] In a more recent study, PHA was used in combination with interleukin-7 (IL-7).[26] Siegers, G. et al, reported a two-step culture protocol, in which sorted TCRγδ⁺ T cells were first treated with concanavalin-A (ConA), IL-2 and IL-4 for 6-8 days, followed by stimulation with IL-2 and IL-4 for another 10 days.[27] After the culture period, Vδ1⁺ T cells were expanded in 59% of cultures and were the dominant subset (average 70% of Vδ1⁺ T cells) in half of the cultures; however, a maximum 25 fold increase of Vδ1⁺ T cells could be achieved with this method.[27] This 2-step culture method was also described in International Patent Application Number PCT/CA99/01024 (published as WO 00/26347). According to those inventors, for continued cell proliferation following the removal of the mitogen, both IL-2 and IL-4 in the second culture medium were essential. A variation of this protocol was later developed, in which total PBMCs were first cultured in the presence of ConA, IL-2 and IL-4 for 6-13 days, followed by the magnetic depletion of contaminant TCRαβ⁺ T cells and stimulation of the remaining cells with IL-2, IL-4 and ConA for another 10 days. After 21 days, Vδ1⁺ T cells expanded from 136 up to 24,384 fold, although a much lower purity level could be achieved (less than 30% of cells in culture were Vδ1⁺ T cells), while most contaminant cells (around 55% of cells) were Vδ2⁺ T cells.[28]

Finally, our group has previously described a method to selectively expand and differentiate cell populations enriched in Vδ1⁺ T cells expressing natural cytotoxicity receptors (NCRs) that could mediate improved killing of leukemia cell lines and CLL patient neoplastic cells.[29] This patented method consisted in culturing TCRγδ⁺ T cells or precursors thereof in a culture medium upon stimulation with common γ-chain cytokines (such as IL-2 or IL-15) and TCR agonists (e.g., PHA or anti-CD3 mAb) for 2-3 weeks (International Patent Application Number PCT/IB2012/052545 published as WO 2012/156958). One important limitation of this method is the small number of cells obtained, inappropriate for clinical applications.

Other Human TCRγδ⁺ T Cell Subsets

The majority of non-Vδ1⁺ and non-Vδ2⁺ TCRγδ⁺ T cells in humans express the Vδ3 TCR chain. Human TCRγδ⁺

Vδ3+ T cells account for ~0.2% of circulating T cells,[30] but are enriched in the peripheral blood of renal and stem cell transplant recipients with CMV activation,[4, 21] in patients with HIV infection[31] or with B-CLL,[17] and in healthy livers.[32] Activated TCRγδ+ Vδ3+ T cells were able to kill CD1d+ cells and epithelial tumors in vitro.[4] However, available cell culture methods cannot produce large numbers of TCRγδ+ Vδ3+ T cells for clinical applications.

Other Methods for the Production of TCRγδ+ T Cell-Enriched Populations

Several methods have been used for the simultaneous expansion of several subsets of TCRγδ+ T cell populations in vitro. Total PBMCs were treated with plate-bound anti-TCRγδ mAb and IL-2 for 3 weeks, resulting in about 90% of TCRγδ+ T cells, most of which were Vδ2+ T cells, and a small percentage of Vδ1+ T cells.[33] Lopez, et al, generated apoptosis-resistant TCRγδ+ T cells by treating cells with high dose interferon-γ (IFN-γ), IL-12, anti-CD2 mAb and soluble anti-CD3 mAb, in the presence of IL-2. Vδ2+ T cells were the dominant subset after cell expansion.[34] More recently, polyclonal TCRγδ+ T cells were expanded in the presence of γ-irradiated artificial antigen-presenting cells (aAPC) of tumor origin genetically modified to co-express CD19, CD64, CD86, CD137L, and membrane bound IL-15.[3, 35] Cells were further cultured in the presence of soluble IL-2 and IL-21.

Need for Improved Methods for Expanding Vδ2− TCRγδ+ T Cells In Vitro

Recent studies have demonstrated that TCRγδ+ T cells with the Vδ1 chain and those with neither Vδ1 nor Vδ2 chains have properties which makes them more attractive anticancer effectors in adoptive immunotherapy.[36] Vδ2− TCRγδ+ T cells (here also designated as Vδ2− γδ T cells) exhibited higher anti-tumor cytotoxicity and increased survival capacities than Vδ2+ T cells, both in vitro and in vivo.[26, 29, 37] Consequently, a medicinal product highly enriched in Vδ2− γδ T cells is expected to generate more potent anti-tumor effects and to provide improved benefits to treated patients. While several methods have been described in the past 5 years that can generate substantial numbers of tumor-targeting Vδ2− γδ T cells in vitro, key unresolved problems still excluded a clinical application of these cells: 1) the use of unsafe reagents and materials in the manufacturing process; 2) the high level of variation in the composition of the final cell products, especially of cell products obtained from different donors, or obtained from cancer patients; and/or 3) the low anti-tumor activity of the final product.[22, 27, 28, 38] There is a need in the art for reliable clinical-grade cell culture methods that can generate a large number of essentially pure Vδ2− γδ T cells (i.e., comprising >90% of these cells) in vitro or ex vivo, consistently and with similar efficacy from different donors, especially from cancer patients.

Previous clinical data on infused Vδ2+ T cells suggested that a clinically relevant dose of TCRγδ+ T cells for treating a disease comprises at least about 1×10⁹ live cells.[39] Consequently, methods aiming to generate Vδ2− γδ T cells for clinical applications should be able to expand these cells in vitro by at least 1.000 fold. However, Vδ2− γδ T cells do not respond to alkylphosphates and the very limited knowledge about the antigens they recognize has limited their expansion in vitro. Plant lectins such as PHA and Con-A have been used to expand and enrich (to very high purity levels) these cells in vitro, at a pre-clinical scale. Accordingly, and because of yet unknown reasons, these common mitogens are remarkably selective for Vδ2− γδ T cells, promoting their proliferation in culture, while inhibiting growth (or inducing apoptosis) of contaminant Vδ2+ T cells.[27, 29] Nevertheless, plant lectins can be toxic if inadvertently infused in humans and regulatory agencies do not recommend their use for clinical applications, due to safety concerns. Moreover, according to our data, plant lectins are not as efficient as monoclonal antibodies at inducing the expansion of Vδ2− γδ T cells in vitro, generating smaller numbers of cells. Several groups have cultured TCRγδ+ T cells in the presence of an anti-CD3 monoclonal antibody, instead of PHA. However, the anti-CD3 mAb binds to CD3 molecules also expressed on contaminant CD3+ TCRαβ+ T cells and CD3+Vδ2+ T cells, causing a decrease in the purity levels of the final cell product. Consequently, Vδ2− γδ T cells must be isolated by magnetic-activated cell sorting (MACS) or by fluorescence-activated cell sorting (FACS) prior to stimulation with anti-CD3 mAb.[25, 40] To complicate things further, critical reagents such as the anti-TCRγδ mAb, anti-TCRVδ1 mAb and anti-TCRVδ3 mAb used to isolate total TCRγδ+ T cells, TCRγδ+Vδ1+ T cells and TCRγδ+Vδ3+ T cells, respectively, are not currently manufactured or approved (by regulatory agencies) for clinical use. Therefore, sufficient numbers of purified Vδ2− γδ T cells suitable for direct application in humans have not been possible to generate.[22] There is a need in the art for methods that do not rely on plant lectins and other unsafe reagents for the production of purified Vδ2− γδ T cell populations. In a previous study, Deniger et al. developed tumor-derived artificial antigen presenting cells (aAPCs) to propagate high numbers of TCRγδ+ T cells expressing a polyclonal repertoire of γ and δ TCR chains.[37] However, as pointed out by the authors,[41] the method could not resolve critical obstacles associated with clinical application of TCRγδ+ T cells. For example, most ingredients are not currently produced in GMP quality and further developments still depend on future interest of manufacturers, complex regulatory approvals, while assuming that the same cell product can be obtained with different reagents, and from cancer patients. Furthermore, key details regarding the exact composition (and variability) of the generated cell products were missing in this study, thus hindering the potential application of this method.

Interleukin-2, interleukin-7 and interleukin-15 are very pleiotropic molecules, with strong stimulatory effects on multiple immune cells, including TCRαβ+ T and Vδ2+ T cells. Consequently, these reagents are not appropriate for expanding Vδ2− γδ T cells in vitro, as contaminating cells will also expand in culture, compromising cell purity. Furthermore, the typical combination of these pro-inflammatory cytokines with γδTCR agonists often leads to activation-induced-cell-death (AICD) of stimulated cells and to smaller numbers of cells obtained. There is a need in the art for methods that can rely on more selective reagents for expanding Vδ2− γδ T cells from highly impure starting samples.

The combination of IL-2 and IL-4 has been used with some success to expand Vδ1+ T cells in vitro. However, we found that the presence of IL-4 in the culture medium induces a strong downregulation of natural killer (NK) activating receptors (such as NKG2D and NCRs) on Vδ2− γδ T cells, weakening their anti-tumor responses (Table 3). The inhibitory effect of IL-4 on Vδ2− γδ T cells occurred even when IL-2 was present. Along the same line, in an independent study, Mao, Y. and colleagues recently demonstrated that cultured Vδ1+ T cells treated with IL-4 and anti-TCRVδ1 mAb secreted significantly less IFN-γ and more IL-10 relative to Vδ2+ T cells. Furthermore, IL-4-treated Vδ1+ T cells expressed lower levels of NKG2D, also indicating that IL-4 weakens the TCRγδ+ T cell-mediated anti-tumor immune response.[42] These observations, together with recent findings on the tumor-promoting effects of Vδ1+ T cells producing interleukin-17 (ref.[43, 44]), have raised concerns about their application, and stressed the need for a detailed characterization of effector Vδ1+ lymphocytes that might be considered for adoptive cell therapy. There is clearly a need in the art for methods able to expand Vδ2− γδ T cells in vitro without the immunosuppressive or inhibitory effects of IL-4.

Finally, several published methods aiming to expand Vδ2− γδ T cells ex vivo require the presence of natural or artificial feeder cells, usually in the form of virus-infected or transformed cells or cell lines, bacteria and parasites. These culture methods are more complex, more prone to microbial contamination and less suitable for clinical applications.

SUMMARY OF THE INVENTION

The present invention provides novel methods for expanding and differentiating human Vδ2− TCRγδ+ T cells in vitro, without the need for the use of feeder cells or microbial or viral components. First, the inventors aimed at improving the expansion and purity levels of cultured Vδ2− TCRγδ+ T cells. A novel, more efficient and selective method to expand these cells in culture was developed, in the presence of a T cell mitogen and IL-4, and in the absence of IL-2, IL-7 and IL-15. Finally, the obtained Vδ2− TCRγδ+ T cells were differentiated towards a more cytotoxic phenotype through additional in vitro optimization steps. After the removal of IL-4 and the addition of a T cell mitogen and IL-15, IL-2, or IL-7 to the culture medium, the previously obtained Vδ2− TCRγδ+ T cells produced pro-inflammatory cytokines and expressed high levels of activating Natural Killer receptors (NKR), which mediated tumor cell killing in vitro. Importantly, upon infusion in mice, the differentiated TCRγδ+ T cells maintained their cytotoxic phenotype and inhibited tumor growth in vivo.

The cell culture method described herein is very robust, highly reproducible and fully compatible with large-scale clinical applications. It generates sufficient numbers of differentiated Vδ2− TCRγδ+ T cells for use in adoptive immunotherapy of cancer, and in a variety of experimental, therapeutic and commercial applications.

Accordingly, in a first aspect, the present invention provides a method for expanding and differentiating Vδ2− TCRγδ+ T cells in a sample comprising:

(1) culturing cells in the sample in a first culture medium comprising a T cell mitogen and at least one growth factor having interleukin-4-like activity; in the absence of growth factors having interleukin-15-like activity; and (2) culturing the cells obtained in step (1) in a second culture medium comprising a T cell mitogen and at least one growth factor having interleukin-15-like activity, in the absence of growth factors having interleukin-4-like activity.

Preferably, the present invention provides a method for expanding and differentiating Vδ2− TCRγδ+ T cells in a sample comprising:

(1) culturing cells in the sample in a first culture medium comprising a T cell mitogen and interleukin-4; in the absence of interleukin-15, interleukin-2 and interleukin-7; and (2) culturing the cells obtained in step (1) in a second culture medium comprising a T cell mitogen and interleukin-15, in the absence of interleukin-4.

The newly obtained method (detailed herein), is based on previously unidentified biological properties of Vδ2− TCRγδ+ T cells and has not been described elsewhere.

DETAILED DESCRIPTION OF THE INVENTION

The present invention relates to novel methods for the isolation and the selective in vitro/ex vivo expansion and differentiation of Vδ2− TCRγδ+ T cells, and to their clinical application. The inventors tested multiple combinations of clinical-grade agonist antibodies and cytokines for their capacity to expand and differentiate (over 2-3 weeks) peripheral blood Vδ2− TCRγδ+ T cells in culture. TCRγδ+ T cells were isolated and expanded in culture in the absence of feeder cells and molecules of microbial origin. The inventors have shown that Vδ2− TCRγδ+ T cells (here also designated as Vδ2− γδ T cells), can be selectively expanded in vitro by culturing these cells in a first culture medium comprising a T cell mitogen and interleukin-4, in the absence of interleukin-2, interleukin-7 and interleukin-15, and sub-culturing these cells in a second culture medium containing a T cell mitogen and interleukin-15, interleukin-2, or interleukin-7, in the absence of interleukin-4. Other key growth factors such as interferon-γ, interleukin-21 and interleukin-1β were also added to one or both culture media to further increase the expansion and purity levels of cultured Vδ2− γδ T cells.

The first culture medium supported the selective survival and expansion of Vδ2− γδ T cells (up to 8.000-fold increase of Vδ1+ T cells in 14 days; Table 3). Importantly, the absence of interleukin-2, interleukin-7 and interleukin-15 during the first days of culture contributed to the starvation and apoptosis of contaminant cells (including TCRαβ+ T and Vδ2+ T cells), which critically depend on these cytokines for survival.

Finally, the presence of IL-2, IL-7, or IL-15 and the absence of IL-4 in the second culture medium permitted the differentiation of the previously selected Vδ2− γδ T cell population, which expanded in vitro a total of several thousand fold and reached >90% of total cells after 21 days of culture (Tables 3 and 7). This second culture step is necessary to change the physiological properties of the cells towards a more appropriate phenotype for use as an anti-tumor or anti-viral treatment. Expanded and differentiated Vδ2− γδ T PBLs obtained after the second culture step expressed high levels of activating Natural Killer receptors (NKR), including NKp30 and NKp44, which synergized with the T-cell receptor to mediate tumor cell targeting in vitro, while not targeting healthy cells. Infusion of the expanded and differentiated Vδ2− γδ T PBLs cells in tumor-bearing immunodeficient mice inhibited tumor growth and limited tumor dissemination to multiple organs, compared to non-treated animals. No evidence of treatment-associated toxicity in biochemical and histological analyses was found. Importantly, expanded and differentiated Vδ2− γδ T PBLs were obtained with similar efficacy from blood samples of healthy donors and leukemia patients. Finally, the present invention discloses methods for isolating and culturing cells using materials and reagents fully compatible with industrial and clinical applications. TCRγδ+ T cells were first sorted in a two-step protocol suitable to be used in a clinical-grade cell sorting machine (CliniMACS; Miltenyi Biotec, GmbH; Germany). Then, cells were cultured with minimum manipulation in a serum-free cell culture medium. Closed, large-scale, gas-permeable plastic cell culture bags were used as recipients for cell culture, instead of open culture plates or flasks. All used reagents and materials (or equivalent reagents and materials) are currently available and manufactured in clinical-grade quality, or in Good Manufacturing Practice (GMP) quality, free of animal-derived components. Therefore, cells produced by this method can be used in a variety of experimental, therapeutic and commercial applications.

In a first aspect, the present invention provides a method for expanding and differentiating Vδ2− TCRγδ+ T cells from a sample containing TCRγδ+ T cells or precursors thereof, comprising:

(1) culturing cells in the sample in a first culture medium comprising a T cell mitogen and at least one growth factor having interleukin-4-like activity; in the absence of growth factors having interleukin-15-like activity; and (2) culturing the cells obtained in step (1) in a second culture medium comprising a T cell mitogen and at least one growth factor having interleukin-15-like activity, in the absence of growth factors having interleukin-4-like activity.

The method of the first aspect of the invention results in expanded cell populations of Vδ2− TCRγδ+ T cells. By "expanded" it is meant that the number of the desired or target cell type in the final preparation is higher than the number in the initial or starting cell population.

The term "a T cell mitogen" means any agent that can stimulate T cells through TCR signaling including, but not limited to, plant lectins such as phytohemagglutinin (PHA) and concanavalin A (ConA) and lectins of non-plant origin, antibodies that activate T cells, and other non-lectin/non-antibody mitogens. Preferred antibody clones include anti-CD3 antibodies such as OKT-3 and UCHT-1 clones, anti-TCRγδ antibodies such as B1 and IMMU510, or anti-TCRVδ1 antibodies such as δTCS1. Within the context of the present invention, antibodies are understood to include monoclonal antibodies (mAbs), polyclonal antibodies, antibody fragments (e.g., Fab, and F(ab')2), single chain antibodies, single chain variable fragments (ScFv) and recombinantly produced binding partners. In one embodiment, the antibody is an anti-CD3 monoclonal antibody (mAb). Other mitogens include phorbol 12-myristate-13-acetate (TPA) and its related compounds, such as mezerein, or bacterial compounds (e.g., Staphylococcal enterotoxin A (SEA) and Streptococcal protein A). The T cell mitogen may be soluble or immobilized and more than one T cell mitogen may be used in the method of the invention.

In the present invention, it was clearly demonstrated that two distinct groups of cytokines, interleukin-4 on one hand, and interleukine-15, interleukin-2 and interleukin-7 on the other hand, must be used for very specific purposes in each culture step, and have opposite actions on cultured Vδ2− γδ T cells. Based on the present study of the effects of IL-4 and IL-15/IL-2/IL-7 on Vδ2− γδ T cells, it should be obvious for any one skilled in the art that these two groups of cytokines are representative members of two groups of growth factors, either having "interleukin-4-like activity" or "interleukin-15-like activity", which can be used under the scope of the present invention.

The term "a growth factor having interleukin-4-like activity" means any compound that has the same activity as IL-4 with respect to its ability to promote similar physiological effects on Vδ2− γδ T cells in culture and includes, but is not limited to, IL-4 and IL-4 mimetics, or any functional equivalent of IL-4. The physiological effects promoted by IL-4 on Vδ2− γδ T cells (as described in the present invention), include the decrease of NKG2D and NCR expression levels, the inhibition of cytotoxic function and improved selective survival. Some of the referred activities of IL-4 on Vδ2− γδ T cells were also reported independently by another group. In that study, IL-4 significantly inhibited the secretion of pro-inflammatory cytokines, including IFN-γ, TNF-α, from activated TCRγδ+ T cells.[45]

The term "a growth factor having interleukin-15-like activity" means any compound that has the same activity as IL-15 with respect to its ability to promote similar physiological effects on Vδ2− γδ T cells in culture and includes, but is not limited to, IL-15 and IL-15 mimetics, or any functional equivalent of IL-15, including IL-2 and IL-7. The physiological effects promoted by IL-15, IL-2 and IL-7 on cultured Vδ2− γδ T cells (as described in the present invention) were essentially equivalent, namely, the induction of cell differentiation towards a more cytotoxic phenotype, including the upregulation of NKG2D and NCR (NKp30 and NKp44) expression levels, increased anti-tumor cytotoxic function and increased production of pro-inflammatory cytokines, such as IFN-γ.

The terms "in the absence of interleukin-15, interleukin-2 and interleukin-7" and "in the absence of interleukin-4" refer not only to the complete absence of these cytokines in the culture medium, but also include the use of such cytokines at concentration levels so low that they cannot produce a measurable response or physiological effect in target cells and thus can be considered absent for practical purposes. Furthermore, "a measurable physiological effect in target cells" refers to any measurable change in the cells' physiological state, within the scope of the present invention and according to standard definitions. For example, changes in the cell's physiological state can be detected by changes in their activation state (recognized by the up-regulation or downregulation of the expression levels of the early-activation cell marker CD69); or detected by changes in their differentiation state (recognized by the up-regulation or downregulation of NKG2D or NCRs), a few hours or a few days after contact with such cytokines. A measurable physiological effect may also be a change in the cell's proliferation rate, as measured by CFSE staining or by other techniques known in the art. It should be apparent for any one skilled in the art that cells cultured in the first culture medium must not receive a functionally relevant stimulus by IL-2, IL-7 and IL-15 or functionally similar growth factors. Additionally, cells in the second culture medium must not receive a functionally relevant stimulus by IL-4 or functionally similar growth factors. Preferably, these cytokines must not be present in the cell culture medium at a final concentration higher than 2 ng/ml; more preferably, not higher than 1 ng/ml, more preferably not higher than 0.1 ng/ml, more preferably, they should be absent.

Preferably, the present invention provides a method for expanding and differentiating Vδ2− γδ T cells in a sample comprising:

(1) culturing cells in the sample in a first culture medium comprising a T cell mitogen and interleukin-4; in the absence of interleukin-15, interleukin-2 and interleukin-7; and (2) culturing the cells obtained in step (1) in a second culture medium comprising a T cell mitogen and interleukin-15, in the absence of interleukin-4.

In another embodiment, the present invention provides a method for expanding and differentiating Vδ2− γδ T cells in a sample comprising:

(1) culturing cells in the sample in a first culture medium comprising a T cell mitogen and interleukin-4; in the absence of interleukin-15, interleukin-2 and interleukin-7; and (2) culturing the cells obtained in step (1) in a second culture medium comprising a T cell mitogen and interleukin-2, in the absence of interleukin-4.

Additionally, in another embodiment, the present invention provides a method for expanding and differentiating Vδ2⁻ γδ T cells in a sample comprising:

(1) culturing cells in the sample in a first culture medium comprising a T cell mitogen and interleukin-4; in the absence of interleukin-15, interleukin-2 and interleukin-7; and (2) culturing the cells obtained in step (1) in a second culture medium comprising a T cell mitogen and interleukin-7, in the absence of interleukin-4.

The first or second culture medium, or both culture media, may additionally include other ingredients that can assist in the growth and expansion of the Vδ2⁻ γδ T cells. Examples of other ingredients that may be added, include, but are not limited to, plasma or serum, purified proteins such as albumin, a lipid source such as low density lipoprotein (LDL), vitamins, amino acids, steroids and any other supplements supporting or promoting cell growth and/or survival.

The first or second culture medium, or both culture media, may also contain other growth factors, including cytokines that can further enhance the expansion of Vδ2⁻ γδ T cells. Examples of such cytokines include, but are not limited to: (i) Interferon-γ and any growth factor having interferon-γ-like activity, (ii) interleukin-21 and any growth factor having interleukin-21-like activity and (iii) IL-1β and any growth factor having interleukin-1β-like activity. Examples of other growth factors that can be added include co-stimulatory molecules such as a human anti-SLAM antibody, any soluble ligand of CD27, or any soluble ligand of CD7. Any combination of these growth factors can be included in the first or second culture medium, or in both media.

The term "a growth factor having interferon-γ-like activity" means any compound that has the same activity as IFN-γ with respect to its ability to promote survival or proliferation of Vδ2⁻ γδ T cells in culture and includes, but is not limited to, IFN-γ and IFN-γ mimetics, or any functional equivalent of IFN-γ.

The term "a growth factor having interleukin-21-like activity" means any compound that has the same activity as IL-21 with respect to its ability to promote survival or proliferation of Vδ2⁻ γδ T cells in culture and includes, but is not limited to, IL-21 and IL-21 mimetics, or any functional equivalent of IL-21.

The term "a growth factor having interleukin-1β-like activity" means any compound that has the same activity as IL-1β with respect to its ability to promote survival or proliferation of Vδ2⁻ γδ T cells in culture and includes, but is not limited to, IL-1β and IL-1β mimetics, or any functional equivalent of IL-1β.

In particular, the inventor has found that the addition of a second growth factor having interferon-γ-like activity to the first or second culture medium, or to both culture media, resulted in enhanced expansion of Vδ2⁻ γδ T cells as compared to the expansion obtained using one growth factor.

Accordingly, in one embodiment, the method of the first aspect of the invention comprises:

(1) culturing cells in the sample in a first culture medium comprising a T cell mitogen, interleukin-4 and interferon-γ, in the absence of interleukin-2, interleukin-7 and interleukin-15; and (2) culturing the cells obtained in step (1) in a second culture medium comprising a T cell mitogen, interleukin-15 and interferon-γ, in the absence of interleukin-4, to expand and differentiate Vδ2⁻ γδ T cells.

Preferably, the growth factor having IFN-γ-like activity is present in an amount from about 1 to about 1000 ng/ml. More preferably, this growth factor is present in an amount from about 2 to about 500 ng/ml. More preferably, this growth factor is present in an amount from about 20 to about 200 ng/ml. Most preferably, the second culture medium comprises about 70 ng/mL of a growth factor having IFN-γ-like activity, such as IFN-γ.

The inventor has also found that the addition of a second growth factor having IFN-γ-like-activity and a third growth factor having IL-21-like-activity to the first or second culture medium, or to both culture media, resulted in enhanced expansion of Vδ2⁻ γδ T cells as compared to the expansion obtained using one or two growth factors.

Accordingly, in one embodiment, the method of the first aspect of the invention comprises:

(1) culturing cells in the sample in a first culture medium comprising a T cell mitogen, interleukin-4, interferon-γ and interleukin-21, in the absence of interleukin-2, interleukin-7 and interleukin-15; and (2) culturing the cells obtained in step (1) in a second culture medium comprising a T cell mitogen, interleukin-15 and interferon-γ, in the absence of interleukin-4, to expand and differentiate Vδ2⁻ γδ T cells.

Preferably, the growth factor having IL-21-like-activity is present in an amount from about 1 to about 500 ng/ml. More preferably, this growth factor is present in an amount from about 2 to about 200 ng/ml. More preferably, this growth factor is present in an amount from about 5 to about 100 ng/ml. Most preferably, the second culture medium comprises about 15 ng/mL of a growth factor having IL-21-like-activity, such as IL-21.

The inventor has also found that the addition of a second growth factor having IFN-γ-like-activity, and a third growth factor having IL-21-like-activity, and a fourth growth factor having IL-1β-like activity, to the first or second culture medium, or to both culture media, resulted in enhanced expansion of the Vδ2⁻ γδ T cells as compared to the expansion obtained using one, two or three growth factors.

Accordingly, in one embodiment, the method of the first aspect of the invention comprises:

(1) culturing cells in the sample in a first culture medium comprising a T cell mitogen, interleukin-4, interferon-γ, interleukin-21 and interleukin-1β, in the absence of interleukin-2, interleukin-7 and interleukin-15; and (2) culturing the cells obtained in step (1) in a second culture medium comprising a T cell mitogen, interleukin-15, interferon-γ and interleukin-21, in the absence of IL-4, to expand Vδ2⁻ γδ T cells.

Preferably, the growth factor having IL-1β-like-activity is present in an amount from about 1 to about 500 ng/ml. More preferably, this growth factor is present in an amount from about 2 to about 200 ng/ml. More preferably, this growth factor is present in an amount from about 5 to about 100 ng/ml. Most preferably, the second culture medium comprises about 15 ng/mL of a growth factor having IL-1β-like-activity, such as IL-1β.

The inventor has also found that the addition of a co-stimulatory molecule to the first or second culture medium, or to both culture media, resulted in enhanced expansion of the Vδ2⁻ γδ T cells as compared to the expansion obtained without using such molecule.

Accordingly, in one embodiment, the method of the first aspect of the invention comprises:

(1) culturing cells in the sample in a first culture medium comprising a T cell mitogen, interleukin-4, and any molecular ligand of CD27, or any molecular ligand of SLAM or any molecular ligand of CD7 receptors, in the absence of interleukin-2, interleukin-7 and interleukin-15; and (2) culturing the cells obtained in step (1) in a second culture medium comprising a T cell mitogen and interleukin-15, in the absence of IL-4, to expand $V\delta2^- \gamma\delta$ T cells.

The term "a molecular ligand" means any molecule or compound that binds to a specific target receptor. In particular, the inventor has found that the addition of a soluble ligand of CD27, or a soluble ligand of CD7 or a soluble ligand of SLAM resulted in enhanced expansion of $V\delta2^- \gamma\delta$ T cells. These soluble ligands constitute functional agonists of each one of these molecular receptors, and any similar agonists binding to these receptors can induce the same effect on $V\delta2^- \gamma\delta$ T cells, for example, agonistic antibodies such as human anti-SLAM antibodies, human anti-CD27 antibodies and human anti-CD7 antibodies.

More than one subculture step can be performed during the total culture period. For example, each of the previously described subculture steps can be further divided into two subculture steps (1a) and (1b) and (2a) and (2b), and different combinations of ingredients can be used according to the originally described method.

Accordingly, in one embodiment, the method of the first aspect of the invention comprises:

(1) culturing cells in the sample in a first culture medium comprising a T cell mitogen, interleukin-4, interferon-γ, interleukin-1β and interleukin-21, in the absence of interleukin-2, interleukin-7 and interleukin-15; and (2a) culturing the cells obtained in step (1) in a second culture medium comprising a T cell mitogen, interleukin-15 and interleukin-21, in the absence of interleukin-4; and (2b) culturing the cells obtained in step (2a) in a third culture medium comprising a T cell mitogen, interleukin-15 and interferon-γ, in the absence of interleukin-4, to expand $V\delta2^- \gamma\delta$ T cells.

In another embodiment, the method of the first aspect of the invention comprises:

(1a) culturing cells in the sample in a first culture medium comprising a T cell mitogen, interleukin-4, interferon-γ, and interleukin-21, in the absence of interleukin-2, interleukin-7 and interleukin-15; and (1 b) culturing the cells obtained in step (1a) in a second culture medium comprising a T cell mitogen, interleukin-4, interferon-γ, and interleukin-1β, in the absence of interleukin-2, interleukin-7 and interleukin-15; and (2) culturing the cells obtained in step (1 b) in a third culture medium comprising a T cell mitogen and interleukin-15, in the absence of interleukin-4; to expand $V\delta2^- \gamma\delta$ T cells.

The $TCR\gamma\delta^+$ T cells obtained by the method of the invention can be used in a variety of experimental, therapeutic and commercial applications. This includes, but is not limited to, subsequent genetic modification or genetic editing of such cells, for example with the objective of improving their therapeutic potential. For example, with the objective of redirecting the specificity of the $TCR\gamma\delta^+$ T cells through the expression of a chimeric antigen receptor (CAR) or TCR on these cells. CAR expression can be induced through electroporation of $TCR\gamma\delta^+$ cells for the insertion of genetic material, or by infecting these cells with viral vectors, such as lentiviruses or retroviruses containing the desired genetic material. Such genetic editing may improve the potency of the $TCR\gamma\delta^+$ T cells by improving homing, cytokine production, recycle killing, and/or improved engraftment.

The present invention provides novel methods for selectively expanding $V\delta2^- TCR\gamma\delta^+$ T cells in culture. The methods of the first aspect of the invention are carried out on a sample, which is also referred to herein as a "starting sample". The methods can use either unfractionated samples or samples which have been enriched for $TCR\gamma\delta^+$ T cells.

The sample can be any sample that contains $TCR\gamma\delta^+$ T cells or precursors thereof including, but not limited to, blood, bone marrow, lymphoid tissue, epithelia, thymus, liver, spleen, cancerous tissues, lymph node tissue, infected tissue, fetal tissue and fractions or enriched portions thereof. The sample is preferably blood including peripheral blood or umbilical cord blood or fractions thereof, including buffy coat cells, leukapheresis products, peripheral blood mononuclear cells (PBMCs) and low density mononuclear cells (LDMCs). In some embodiments the sample is human blood or a fraction thereof. The cells may be obtained from a sample of blood using techniques known in the art such as density gradient centrifugation. For example, whole blood may be layered onto an equal volume of Ficoll-Hypaque™ followed by centrifugation at 400×g for 15-30 minutes at room temperature. The interface material will contain low density mononuclear cells which can be collected and washed in culture medium and centrifuged at 200×g for 10 minutes at room temperature.

Isolated or unpurified $TCR\gamma\delta^+$ T cells can be cultured or maintained in any suitable mammalian cell culture medium such as AIM-V™, RPMI 1640, OPTMIZER CTS™ (Gibco, Life Technologies), EXVIVO-10, EXVIVO-15 or EXVIVO-20 (Lonza), in the presence of serum or plasma. Cells can be transferred, for example, to VueLife® clinical-grade gas-permeable cell culture static bags (Saint Gobain) or to Miltenyi Biotec's clinical-grade cell culture bags. Cell bags containing cells and culture medium can be placed in an incubator at 37° C. and 5% $CO_2$, in the dark.

Prior to culturing the sample or fraction thereof (such as PBMCs) in the first culture medium, the sample or fraction thereof may be enriched for certain cell types and/or depleted for other cell types. In particular, the sample or fraction thereof may be enriched for T cells, or enriched for $TCR\gamma\delta^+$ T cells, or depleted of $TCR\alpha\beta^+$ T cells or depleted of non-$TCR\gamma\delta^+$ T cells. In a preferred embodiment, the sample is first depleted of $TCR\alpha\beta^+$ T cells and then enriched for $CD3^+$ cells.

The sample may be enriched or depleted of certain cell types using techniques known in the art. In one embodiment the cells of a particular phenotype may be depleted by culturing the sample or fraction thereof with an antibody cocktail containing antibodies that bind to specific molecules on the cells to be depleted. Preferably, the antibodies in the cocktail are coupled to magnetic microbeads that can be used to magnetically deplete or enrich target cells when these cells are forced to pass through a magnetic column.

Once the cells in the sample have been fractionated and enriched, if desired, the cells are cultured in a first culture medium comprising a T cell mitogen and at least one growth factor having interleukin-4-like activity, such as interleukin-4, in the absence of growth factors having interleukin-15-like activity, such as interleukin-15, interleukin-2 and interleukin-7.

Preferably, the T cell mitogen in the first culture medium is present in an amount from about 10 to about 5000 ng/ml. More preferably, the T cell mitogen is present in an amount from about 20 to about 2000 ng/ml. More preferably, the T cell mitogen is present in an amount from about 50 to about 1000 ng/ml. Most preferably, the medium comprises 70 ng/mL of a T cell mitogen.

Preferably, the growth factor having interleukin-4-like activity is present in an amount from about 1 to about 1000 ng/ml. More preferably, this growth factor is present in an amount from about 5 to about 500 ng/ml. More preferably, this growth factor is present in an amount from about 20 to about 200 ng/ml. Most preferably, the medium comprises 100 ng/mL of a growth factor having interleukin-4-like activity, such as IL-4.

The cells are preferably cultured in the first culture medium for a period of time ranging from about 2 days to about 21 days. More preferably, from about 3 days to about 14 days. More preferably, from about 4 days to 8 days.

Following culture in the first culture medium, cells are sub-cultured in a second culture medium comprising a T cell mitogen and at least one growth factor having interleukin-15-like activity, such as IL-15, IL-2 or IL-7, in the absence of growth factors having interleukin-4-like activity, such as IL-4. If the cells are sub-cultured, for example, in the presence of both IL-15 and IL-4, then proliferation continues but cell viability decreases and key NK receptors located at the cell surface (such as NKG2D, NKp30 and NKp44) are internalized to the interior of the cell. Consequently, these receptors can no longer bind to their ligands expressed on tumor cells, which reduces the anti-tumor cytotoxic activity of these cells.

The subculture step consists in culturing the cells obtained in step 1 in a new culture medium. This can be achieved through the addition of fresh culture medium to the first culture medium, preferably after the removal of a fraction of the first culture medium. This can be done by centrifuging and/or decanting the cells, removing a fraction of the first culture medium and resuspending the cells in the second culture medium. Preferably, the subculture step involves the removal of at least ¾ of the first culture medium. The subculture step should be carried out because it is important for the expansion and differentiation of Vδ2⁻ γδ T cells that the growth factor having interleukin-4-like activity is removed during the subculture step.

Preferably, in the second culture medium, the T cell mitogen is present in an amount from about 0.1 to about 50 μg/ml. More preferably, the T cell mitogen is present in an amount from about 0.3 to about 10 μg/ml. More preferably, the T cell mitogen is present in an amount from about 0.5 to about 5 μg/ml. Most preferably, the medium comprises 1 μg/mL of a T cell mitogen.

Preferably, the growth factor having interleukin-15-like activity, such as IL-15, IL-2 or IL-7, is present in an amount from about 1 to about 1000 ng/ml. More preferably, this growth factor is present in an amount from about 2 to about 500 ng/ml. More preferably, this growth factor is present in an amount from about 20 to about 200 ng/ml. Most preferably, the second culture medium comprises about 70 ng/mL of a growth factor having interleukin-15-like activity, such as IL-15, IL-2 or IL-7.

The cells are preferably cultured in the second culture medium for a period of time ranging from about 2 days to about 30 days. More preferably, from about 5 days to about 21 days. More preferably, from about 10 days to 15 days.

Preferably, in the first aspect of the invention, both the first and second culture media are supplemented with serum or plasma. The amount of plasma in the first and second culture media is preferably from about 0.5% to about 25% by volume, for example from about 2% to about 20% by volume or from about 2.5% to about 10% by volume, for example is about 5% by volume. The serum or plasma can be obtained from any source including, but not limited to, human peripheral blood, umbilical cord blood, or blood derived from another mammalian species. The plasma may be from a single donor or may be pooled from several donors. If autologous TCRγδ⁺ T cells are to be used clinically, i.e. reinfused into the same patient from whom the original sample was obtained, then it is preferable to use autologous plasma as well (i.e. from the same patient) to avoid the introduction of hazardous products (e.g. viruses) into that patient. The plasma should be human-derived to avoid the administration of animal products to the patient.

The TCRγδ⁺ T cells obtained according to the method of the first aspect of the invention can be separated from other cells that may be present in the final culture using techniques known in the art including fluorescence activated cell sorting, immunomagnetic separation, affinity column chromatography, density gradient centrifugation and cellular panning.

TCRγδ⁺ T cells obtained by the method of the first aspect of the invention are also of use. Accordingly, the inventor describes a cell preparation of TCRγδ⁺ T cells.

In a second aspect, the present invention provides a cell preparation enriched in TCRγδ⁺ T cells prepared according to the method of the first aspect of the invention.

In a third aspect, the present invention provides a cell preparation enriched in TCRγδ⁺ T cells wherein greater than 80% of the total cells are TCRγδ⁺ T cells.

Preferably, in the second and third aspects of the invention the TCRγδ⁺ T cells comprise greater than 80%, more preferably greater than 90% and most preferably greater than 95%, of the total cells in the enriched population.

The TCRγδ⁺ T cells obtained by the method of the first and second aspect of the invention may be used in any and all applications. TCRγδ⁺ T cells are thought to be a first line of defense against infectious pathogens. In addition, TCRγδ⁺ T cells possess intrinsic cytolytic activity against transformed cells of various origins including B-cell lymphomas, sarcomas and carcinomas. As a result, the TCRγδ⁺ T cells obtained and cultured ex vivo according to the methods of the invention can be transfused into a patient for the treatment or prevention of infections, cancer or diseases resulting from immunosuppression.

Accordingly, in a fourth aspect the present invention provides a method of modulating an immune response comprising administering an effective amount of TCRγδ⁺ T cells prepared according to a method of the first or second aspect of the invention or obtained from a cell preparation according to the second or third aspect of the invention to an animal in need thereof.

The term "effective amount" as used herein means an amount effective, at dosages and for periods of time necessary to achieve the desired results.

The term "animal" as used herein includes all members of the animal kingdom. Preferably, the animal is a mammal, more preferably a human.

In a fifth aspect, the present invention provides a method of treating an infection comprising administering an effective amount of TCRγδ⁺ T cells prepared according to the method of the first or second aspect of the invention or obtained from a cell preparation according to the second or third aspect of the invention to an animal in need thereof.

Examples of infections that may be treated include, but are not limited to, bacterial infections such as those caused by *Mycobacteria* (e.g. tuberculosis), viral infections such as those caused by herpes simplex virus (HSV), human immunodeficiency virus (HIV) or the hepatitis viruses, and parasitic infections such as those caused by *Plasmodium* (e.g. malaria).

In a sixth aspect, the present invention provides a method for treating cancer comprising administering an effective amount of TCRγδ+ T cells prepared according to the method of the first or second aspect of the invention or obtained from a cell preparation according to the second or third aspect of the invention to an animal in need thereof.

Examples of cancer that may be treated include, but are not limited to, leukemias including chronic lymphocytic leukemia, chronic myelogenous leukemia, acute myelogenous leukemia, acute lymphoblastic leukemia, and T cell and B cell leukemias, lymphomas (Hodgkin's and non-Hodgkins), lymphoproliferative disorders, plasmacytomas, histiocytomas, melanomas, adenomas, sarcomas, carcinomas of solid tissues, hypoxic tumors, squamous cell carcinomas, genitourinary cancers such as cervical and bladder cancer, hematopoietic cancers, head and neck cancers, and nervous system cancers.

In one embodiment, the cancer to be treated is chronic lymphocytic leukemia. In such an embodiment, PBMCs can be obtained from a patient with chronic lymphocytic leukemia (CLL). After culturing and expanding for TCRγδ+ T cells, the expanded cells will not significantly contain cancerous CLL cells making them well suited for re-infusion back to the patient.

These aspects of the invention also extend to the TCRγδ+ T cells obtained by a method of the first or second aspect of the invention or obtained from a cell preparation according to the second or third aspect of the invention for use in a method of modulating an immune response, treating an infection or treating cancer as described herein above. The invention further includes the use of the TCRγδ+ T cells obtained according to methods of the first or second aspect of the invention in the manufacture of a medicament or pharmaceutical composition to modulate an immune response, to treat an infection or to treat cancer as described hereinabove.

The TCRγδ+ T cells obtained according to the present invention can also be used in experimental models, for example, to further study and elucidate the function of the cells. Additionally, these cells may be used for studies directed towards the identification of the antigens/epitopes recognized by TCRγδ+ T cells and for the design and development of vaccines.

Accordingly, in a seventh aspect, the present invention provides a method for vaccinating an animal comprising administering an effective amount of TCRγδ+ T cells obtained by a method of the first aspect of the invention or obtained from a cell preparation according to the second or third aspect of the invention to an animal in need thereof. Such vaccine can be given to immunocompromised patients or individuals with elevated risk of developing an infectious disease or cancer.

This aspect of the invention also extends to the use of TCRγδ+ T cells prepared according to the first aspect of the invention or obtained from a cell preparation according to the second or third aspect of the invention for the manufacture of a vaccine, and to TCRγδ+ T cells prepared according to the method of the first aspect of the invention or obtained from a cell preparation according to the second or third aspect of the invention for use in a method of vaccinating an animal.

The obtained TCRγδ+ T cells, according to the invention may be immediately used in the above therapeutic, experimental or commercial applications or the cells may be cryopreserved for use at a later date.

Preferred features of the second and subsequent aspects of the invention are as described for the first aspect of the invention mutatis mutandis.

Other features and advantages of the present invention will be apparent from this detailed description. It should be understood, however, that the detailed description and the specific examples while indicating preferred embodiments of the invention are given by way of illustration only, since various changes and modifications will become apparent to those skilled in the art from this detailed description.

The present invention is completely different from other inventions that were previously described in this field. Patent Application no PCT/CA1999/001024 (WO/2000/026347; Filing Date of 4 Nov. 1999), describes a method for the production of TCRγδ+ T cells. The method involves two steps, wherein TCRγδ+ T cells in the starting sample are cultured in a first culture medium comprising a T cell mitogen and at least two cytokines, preferably interleukin-2 and interleukin-4. Cells obtained in the first step are then cultured in a second culture medium comprising at least two cytokines, which are preferably interleukin-2 and interleukin-4. Importantly, cytokines used in each step can be the same or different.

In contrast, the present invention discloses a 2-step method for selectively expanding and differentiating Vδ2− γδ T cells in culture, wherein the first and second culture steps are necessarily different from each other. The first step comprises culturing TCRγδ+ T cells in the starting sample in a culture medium comprising a T cell mitogen and a growth factor having IL-4-like activity, preferably interleukin-4, in the absence of interleukin-2, interleukin-7 and interleukin-15. In the present invention, it was clearly demonstrated that IL-4 and IL-2 (or IL-7 or IL-15) execute a very specific function in each culture step, and have opposite activities. The first culture medium contains a growth factor having IL-4-like activity, which cannot be mixed with (IL-2/IL-7/IL-15-like) growth factors, otherwise cell viability and proliferation will decrease and the expected cell product will not be produced. The first cell culture step is used to expand TCRγδ+ T cells many fold in an exceptional short period of time, generating a cell product highly enriched in Vδ2− γδ T cells. In fact, the absence of IL-2/IL-7-IL15 like growth factors in the culture medium allows the elimination of many impurities (other cell types) that would not be eliminated without this innovation. The expanded Vδ2− γδ T cells are in a less differentiated state since they have not contacted interleukin-2/-15/-7-like growth factors. In order to differentiate cells towards a more cytotoxic and pro-inflammatory phenotype, Vδ2− γδ T cells obtained in the first step must then be cultured in a second culture medium comprising a T cell mitogen and a growth factor having interleukin-15-like activity, in the absence of a growth factor having interleukin-4-like activity. Again, it is critical that these different growth factors are not mixed, since the presence of IL-4 in the second culture medium decreased cell viability and cytotoxic function. The second culture step further expands Vδ2− γδ T cells in culture and makes them better effector cells, generating a distinctive cell product that can be used for many therapeutic purposes.

Patent no US2003/0157060 A1 (Application no U.S. Ser. No. 10/239,854); and Filing Date of 3 Mar. 2000), describes another method for expanding TCRγδ+ T cells in culture. The method also involves two steps, wherein TCRγδ+ T cells in the starting sample are cultured in a first culture medium comprising (1) a T cell mitogen, (2) a growth factor having interleukin-2-like activity and (3) a growth factor having interleukin-7-like activity. Cells obtained in the first step are then cultured in a second culture medium comprising (1) a growth factor having interleukin-2-like activity and a (2) growth factor having interleukin-7-like activity to expand TCRγδ+ T cells.

In contrast, the present invention is different since the two culture steps are necessarily different, as they serve distinct purposes. The invention clearly excludes the use of growth factors having interleukin-2-like activity or interleukin-7-like activity in the first culture step, due to reasons already explained (see above). Although the present invention describes the presence of other growth factors in the first and/or second culture medium, including cytokines such as Interferon-γ, IL-1β and IL-21, these cytokines cannot be considered to have interleukin-2-like or interleukin-7-like activity since the physiological effects that they exert on Vδ2− γδ T cells are very different. For example, cells cultured in the presence of Interferon-γ, IL-1β and IL-21 (in the absence of IL-2, IL-7 and IL-15) could not acquire their full cytotoxic function and differentiated state, thus Interferon-γ, IL-1β and IL-21 could not mimic the high pro-inflammatory effects induced by IL-2, IL-7 and IL-15 on cultured Vδ2− γδ T cells (Table 2). Additionally, some of these cytokines, such as Interferon-γ and IL-1β, belong to a structurally different family of cytokines.

The invention will now be described with reference to the following Examples and Figures, in which:

FIGURES

FIG. 1 shows percentages of TCRγδ+ T PBLs in a peripheral blood sample collected from a healthy donor, before and after magnetic activated cell sorting (MACS). 50-150 ml of fresh peripheral blood was obtained from a healthy volunteer and diluted in a 1:1 ratio (volume-to-volume) with PBS (Invitrogen Gibco) and centrifuged in Ficoll-Paque (Histopaque-1077; Sigma-Aldrich) in a volume ratio of 1:3 (1 part ficoll to 3 parts of diluted blood) for 35 minutes at 1.500 rpm and 25° C. The interphase containing mononuclear cells (PBMCs) was collected and washed (in PBS). Total TCRγδ+ T cells were labeled with an anti-TCRγδ mAb conjugated with magnetic microbeads and TCRγδ+ T cells were isolated (to above 75% purity) with a magnetic column (Miltenyi Biotec, German). Cells were labeled with the following fluorescent monoclonal antibodies: anti-CD3PerCP-Cy5.5 (Biolegend; clone SK7); anti-TCR-Vδ1-APC (Miltenyi Biotec, clone REA173); anti Mouse IgG1κ-APC Isotype Ctrl (Miltenyi Biotec; clone IS5-21F5). Cells were analyzed on a Fortessa II flow cytometer (BD Biosciences). Shows representative results of 6 independent experiments.

Figure 2:
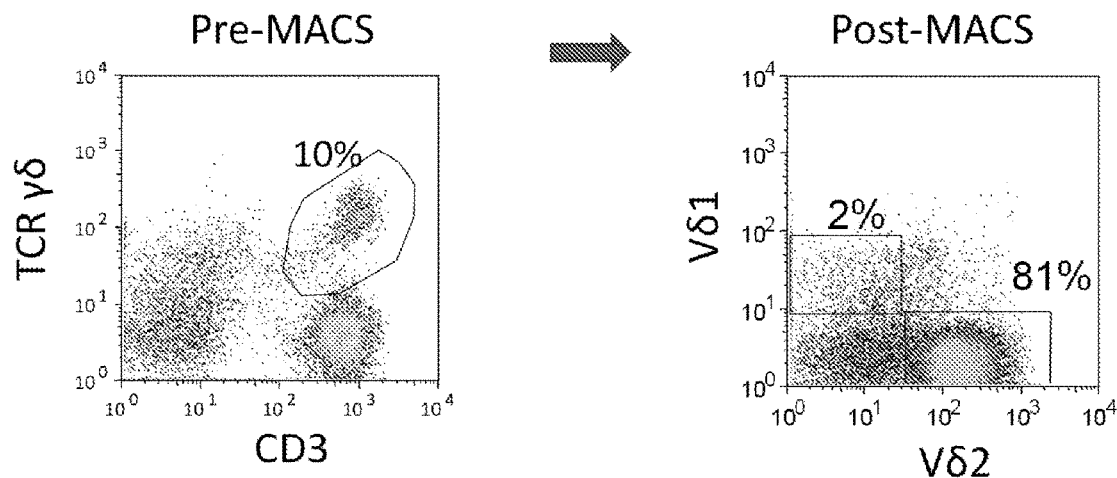

FIG. 2 shows percentages of TCRγδ+ T PBLs in a peripheral blood sample collected from the previously selected healthy donor, before and after the 2-steps MACS sorting procedure. 50-150 ml of fresh peripheral blood was obtained from healthy volunteers and diluted in a 1:1 ratio (volume-to-volume) with PBS (Invitrogen Gibco) and centrifuged in Ficoll-Paque (Histopaque-1077; Sigma-Aldrich) in a volume ratio of 1:3 (1 part ficoll to 3 parts diluted blood) for 35 minutes at 1.500 rpm and 25° C. The interphase containing mononuclear cells (PBMCs) was collected and washed (in PBS). Unwanted TCRαβ+ T lymphocytes were then labelled by incubation in the presence of a murine anti-human TCRαβ monoclonal antibody (mAb) conjugated to Biotin (Miltenyi Biotec Ref #701-48, clone BW242/412). Cells were then labelled again with a murine anti-Biotin mAb coupled to magnetic microbeads (Miltenyi Biotec Ref #173-01). Finally, the cell suspension was loaded onto a magnetic column (Miltenyi Biotec, Germany) and TCRαβ+ T lymphocytes were magnetically depleted (and discarded). CD3+ cells (of which most of them were TCRγδ+ T cells) present in the remaining cell population were labelled with a murine anti-human CD3 mAb (Miltenyi Biotec Ref #273-01, clone OKT-3, targeting an epitope located on the CD3epsilon chain), conjugated to superparamagnetic iron dextran particles. Cells were loaded onto a magnetic MACS separation column and CD3+ cells were positively selected (purified). Cells were stained for TCRγδ, CD3, TCRVδ1 and TCRVδ2 markers, and analysed on a Fortessa II flow cytometer (BD Biosciences). Shows representative results of 6 independent experiments.

FIGS. 3A, 3B, 3C and 3D show a summary of tested culture conditions. A-C. TCRγδ+ PBLs from a healthy donor were isolated by MACS as previously described and cultured in 96-well plates at 1 million cells/ml in complete medium (Optmizer CTS, GIBCO) supplemented with 5% human serum, 1 mM L-glutamine, at 37° C. and 5% $CO_2$. Cells were equally distributed by multiple wells and cultured in the presence of three fixed combinations of anti-CD3 mAb and IL-4, further supplemented with various concentrations of IL-2, IL-7, IL-15 or IFN-γ. Fresh medium supplemented with the same growth factors was added every 5-6 days. At the end of the culture period, cells were counted and cell phenotype was analyzed by flow cytometry. Each growth factor was used separately in serial dilutions from 500 ng/ml to 0.1 ng/ml. Graphs show the best culture condition (i.e., highest fold expansion of Vδ1+ cells) obtained, for each cytokine (IL-2, IL-7, IL-15 and IFN-γ). The control sample contained IL-4 and anti-CD3 mAb only. D. Total CD3+ PBLs were isolated by MACS with an anti-human CD3 mAb (coupled with paramagnetic beads) from the peripheral blood of the same donor and cultured and analyzed as previously described. Shows average±SD of 3 technical replicates. Statistical analysis was performed using Graphpad-Prism software. Differences between subpopulations were assessed using the Student t test and are indicated when significant as *$P<0.05$; $P<0.01$; and *$P<0.001$ in the figures.

Figure 4:
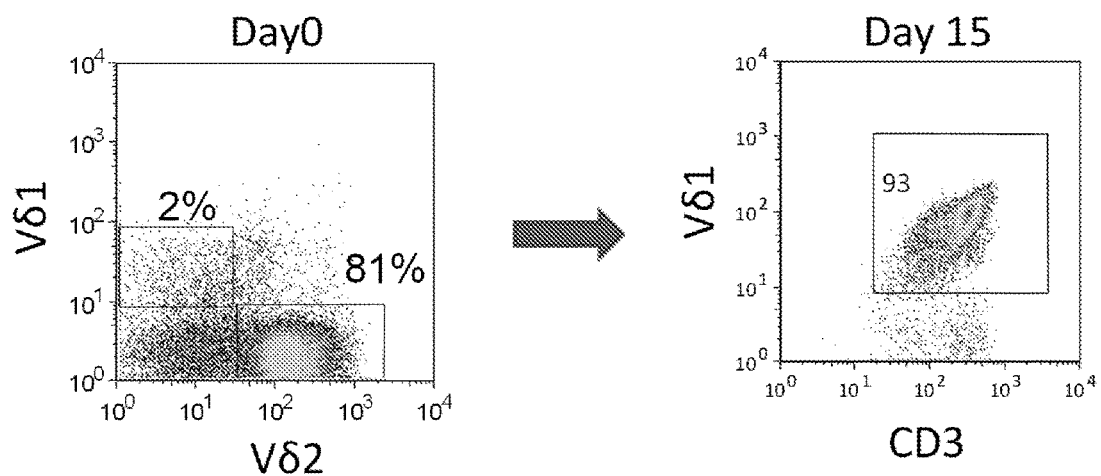

FIG. 4 shows the percentages of Vδ1+ T PBLs before and after in vitro culture for 15 days. TCRγδ+ PBLs from a healthy donor were isolated by MACS as previously described and cultured in the presence of 200 ng/ml IFN-γ, 1 ug/ml α-CD3 and 100 ng/ml IL-4. A fraction of fresh medium containing the same combination of growth factors was added every 5-6 days. Shows the FACS-plot analysis at day 15. Representative results of 3 independent experiments.

Figure 5A:
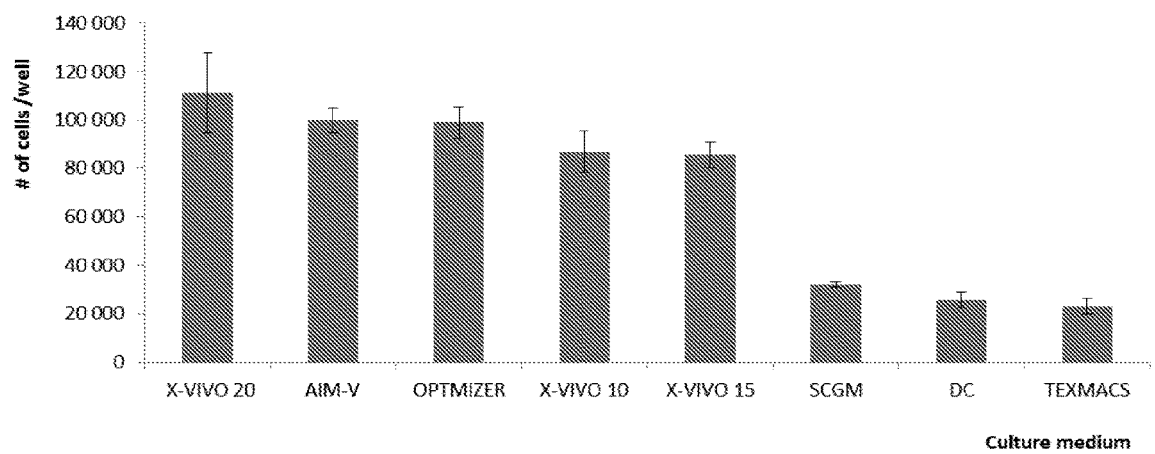
Figure 5B:
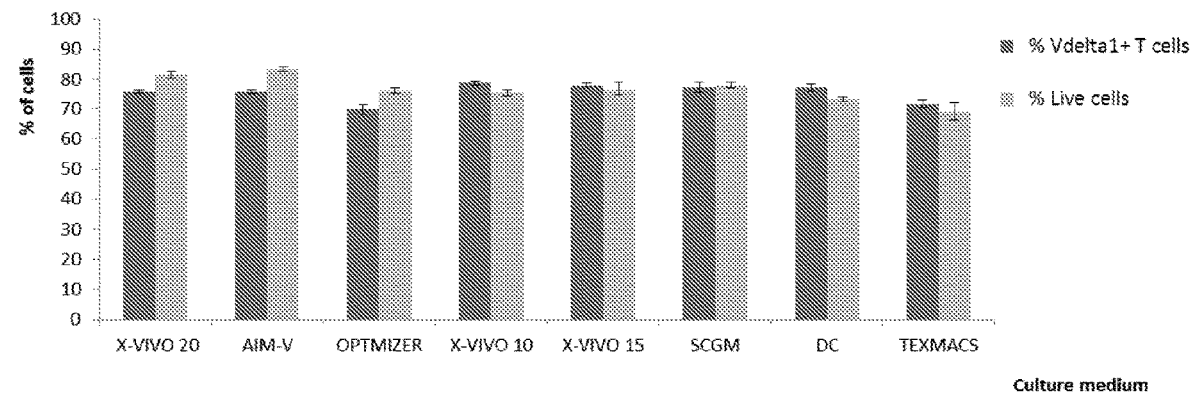

FIGS. 5A and 5B show a panel of tested cell culture media. TCRγδ+ T PBLs from a healthy donor were isolated by MACS as previously described and cultured in different commercially available serum-free, clinical grade cell culture media. Cells were cultured in a first culture medium in the presence of 70 ng/ml IFN-γ, 1 μg/ml α-CD3 and 100 ng/ml IL-4, followed by culture in a second culture medium in the presence of 100 ng/ml IL-15 and 2 μg/ml anti-CD3 mAb, (in the absence of IL-4). Shows final number of cells (5A) and percentages (5B) of cells after FACS analysis at day 15. Shows average±SD of 3 technical replicates.

Figure 6:
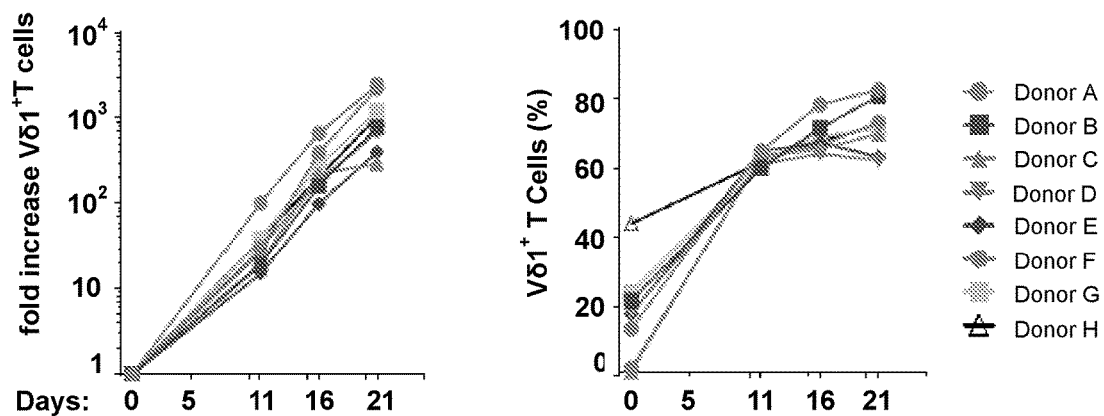
Figure 7:
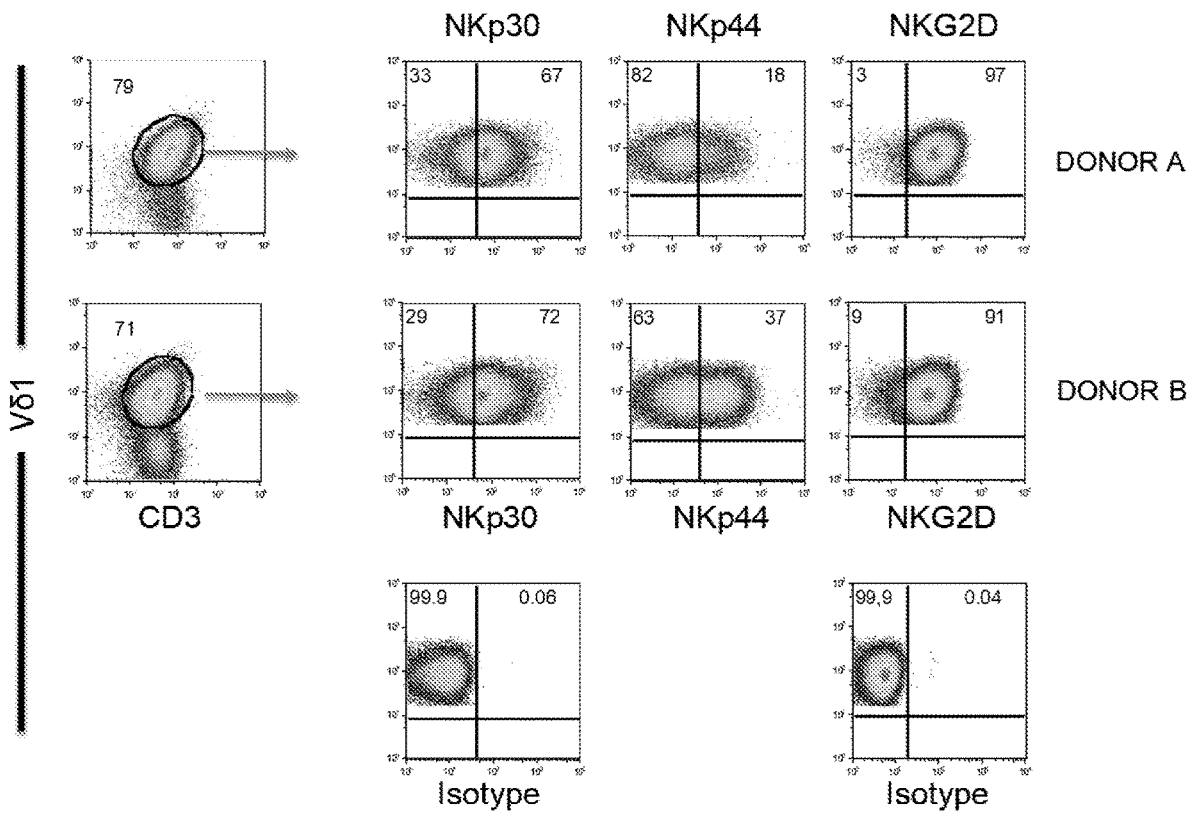

FIG. 6 shows that Vδ1+ T cells expand in vitro to become the dominant cell subset in culture. 70 ml of concentrated peripheral blood (corresponding to 450 ml of peripheral blood) was obtained from 8 Buffy Coat units collected from 8 healthy donors. Blood was centrifuged undiluted in Ficoll-Paque (Histopaque-1077; Sigma-Aldrich) in a volume ratio of 1:3 (1 part ficoll to 3 parts of blood) for 35 minutes at 1.600 rpm and 25° C. The interphase containing mononuclear cells (PBMCs) was collected and washed (in saline buffer). TCRγδ+ PBLs were isolated by the previously described 2-step MACS and resuspended in serum-free culture medium (OPTMIZER, GIBCO) supplemented with 5% autologous plasma and 1 mM L-glutamine. Cells were seeded at a concentration of $0.5 \times 10^6$ cells/ml and expanded in closed gas-permeable, 1 L cell culture plastic bags in the incubator at 37° C. and 5% $CO_2$. Growth factors were added to the cell culture media according to the previously described 2-step protocol: 70 ng/ml anti-CD3 mAb, 100 ng/ml IL-4, 70 ng/ml IFN-γ, 7 ng/ml IL-21 and 15 ng/ml IL-1β were added to the first culture medium and 70 ng/ml IL-15, 100 ng/ml IFN-γ, 15 ng/ml IL-21 and 1 μg/ml anti-CD3 mAb were added to the second culture medium. A fraction of old medium was removed and fresh medium was added every 5-6 days, supplemented with growth factors. Accessory "feeder" cells were not required in this system. Left panel shows percentages of CD3+Vδ1+ cells among total live cells as analyzed by flow cytometry. Right panel shows fold increase in the absolute number of CD3+Vδ1+ T cells relative to the initial cell number. Live cells were counted using Trypan Blue-positive exclusion in a haemocytometer. Shows an average of 3 measurements of number of cells FIG. 7 shows the expression of several cell surface markers in in vitro expanded Vδ1+ T cells. Expression of the activating receptors NKp30, NKp44 and NKG2D in CD3+ Vδ1+ T cells after 16 days of culture (as in Table 8). Isotype mAb control stainings are also shown (note that the control for NKp30 and NKp44 expression is the same).

FIGS. 8A, 8B, and 8C show that in vitro expanded TCRγδ+ T cells are cytotoxic against CLL cells but not against autologous PBMCs. After 21 days of expansion and differentiation (as described in FIG. 6), the resulting TCRγδ+ T cells were co-incubated with target cells (pre-labelled with DDAO-SE) for 3 h at 37° C., and target cell death was assessed by Annexin V staining. (A) Flow cytometry analysis of susceptible MEC-1 CLL cells (upper panel) and non-susceptible autologous PBMCs (lower panel). Representative plots of 3 technical replicates. (B) Impact of different target:effector cell ratios or of blocking antibodies against NKG2D or NKp30 on MEC-1 leukemia cell killing. Error bars represent SD (n=3, *P<0.05). (C) Expanded (and differentiated) TCRγδ+ T cells (designated herein as "DOT-cells") of donor A were co-incubated with three B-CLL primary cell samples (collected from the peripheral blood of CLL/SLL patients and enriched for CD19 by MACS) or with autologous healthy PBMCs. Shows Mean+SD of 3 technical replicates.

Detailed methods: The MEC-1 CLL cell line[46] was obtained from the German Resource Center for Biologic Material (DSMZ). MEC-1 tumor cells were cultured in T25 flasks in complete 10% RPMI 1640 with 10% Fetal Bovine Serum, 2 mM L-Glutamine and maintained at $10^5$ up to $10^6$ cells/mL by dilution and splitting in a 1:3 ratio every 3-4 days. For cytotoxicity assays, in vitro expanded TCRγδ+ T cells were plated in 96-well round-bottom plates. Tumor cell lines or leukemia primary samples were stained with CellTrace Far Red DDAO-SE (1 μM; Molecular Probes, Invitrogen) and incubated at the indicated target:effector ratio with TCRγδ+ T cells in RPMI 1640 medium for 3 hours at 37° C. and 5% $CO_2$, in the presence of 70 ng/ml IL-15. All cells were then stained with Annexin V-FITC (BD Biosciences) and analyzed by flow cytometry.

FIG. 9 shows that activated TCRγδ+ T cells produce high levels of IFN-γ. TCRγδ+ T cells were produced from two healthy donors in cell culture bags for 21 days, following the 2-step culture protocol, as previously described. Cells were washed, plated in 96-well plate and re-stimulated with fresh medium supplemented with 100 ng/ml IL-15 and 2 μg/ml anti-CD3 mAb. After 48 h, cell culture supernatants were analyzed by flow cytometry by Cytometric bead array (BD Biosciences). OpTmizer refers to cells kept in media not supplemented with activating compounds. Shows Mean+SD of 3 technical replicates. Error bars represent SD (n=3, **P<0.01).

Figures 10A, 10B:
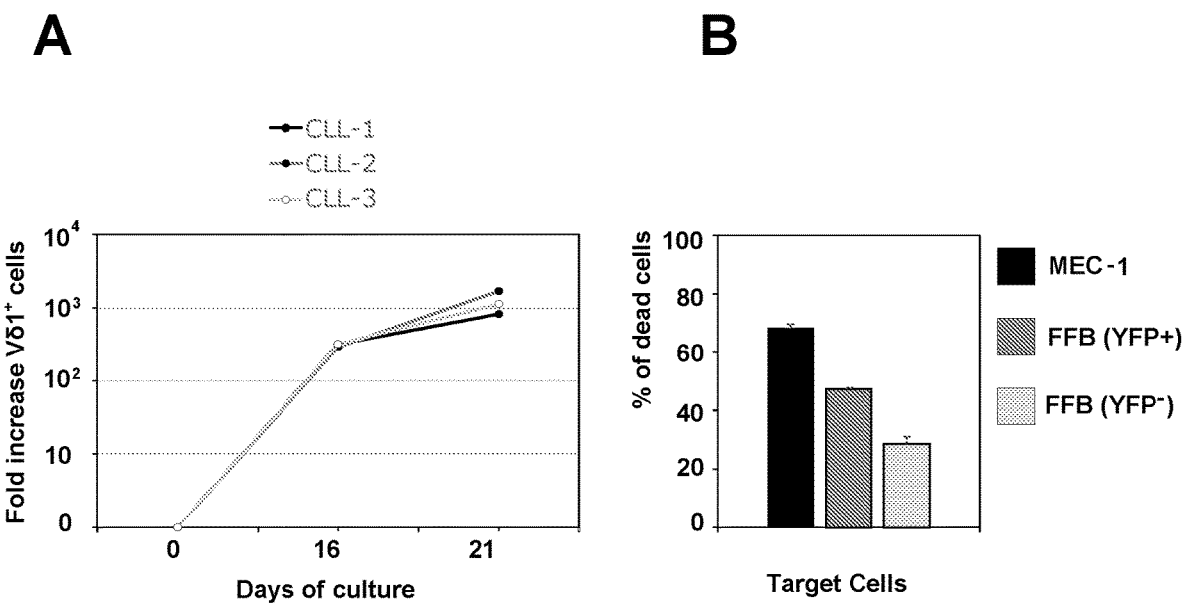

FIGS. 10A and 10B show that TCRγδ+ T cells from CLL/SLL patients expand robustly in vitro and are highly cytotoxic against CLL/SLL cells and CMV-infected cells. MACS-sorted TCRγδ+ PBLs from three CLL/SLL patients were cultured for 21 days with cytokines and mAb as previously described. Left panel: Cells were analysed by flow cytometry for TCRVδ1/CD3 co-expression and fold increase of CD3+Vδ1+ T cells was calculated. Live cells were identified by flow cytometry with a viability dye (Zombie Violet; Biolegend) and counted with Trypan Blue in a haemocytometer. Right panel: TCRγδ+ T cells from a CLL/SLL patient were co-cultured for 3 h at 1:10 target-effector ratio in 96-well plate with CLL/SLL-derived MEC-1 cells or with human foreskin fibroblasts (FFB), either healthy or previously infected with YFP+ Cytomegalovirus strain AD169 (m.o.i 0.005; error bars represent SD (n=3 for each group). Percentage of dead tumor cells before incubation with DOT-cells was around 20% in each group. SLL is for Small Lymphocytic Lymphoma.

Figure 11:
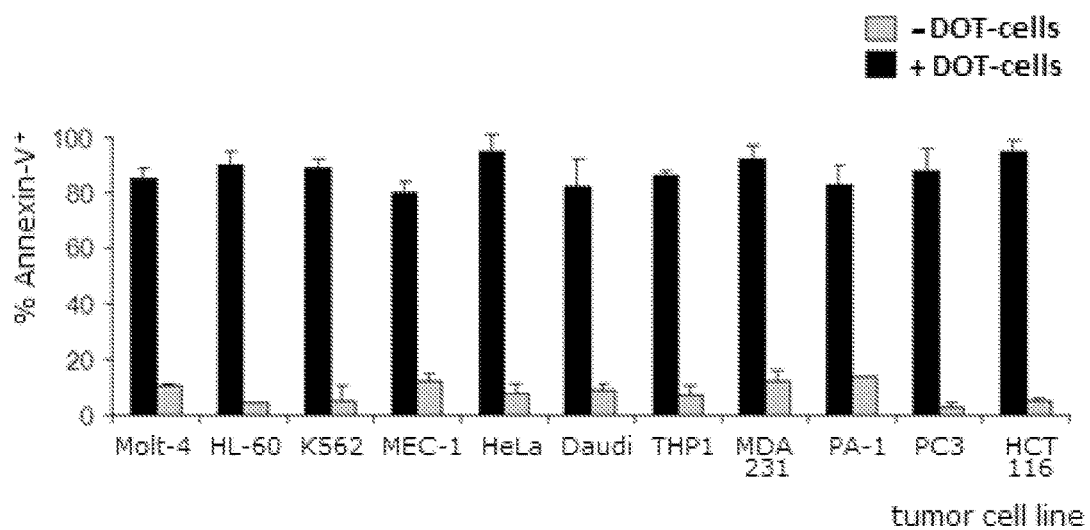

FIG. 11 shows that in vitro expanded TCRγδ+ T cells are cytotoxic against cancer cells of diverse tissue origins. Peripheral blood TCRγδ+ T lymphocytes from one healthy donor were MACS-sorted and stimulated ex vivo in the presence of cytokines and anti-CD3 mAb for 21 days, according to the described two-step culture protocol. Cells were co-incubated for 3 h in 96-well plates with a panel of tumor cell lines: MOLT-4 (Acute lymphoblastic leukemia; ALL); HL-60 (Acute myeloid leukemia; AML); K562 (Chronic myeloid leukemia; CML); MEC-1 (Chronic lymphocytic leukemia; CLL); HELA (Cervical carcinoma); Daudi (Burkitt's lymphoma); THP-1 (Acute monocytic leukemia; AMoL); MDA-231 (Breast carcinoma), PA-1 (Ovarian carcinoma); PC3 (Prostate carcinoma) and HCT116 (Colon carcinoma). Tumor cell death was evaluated by Annexin-V staining (n=3 technical replicates).

Figures 12A, 12B:
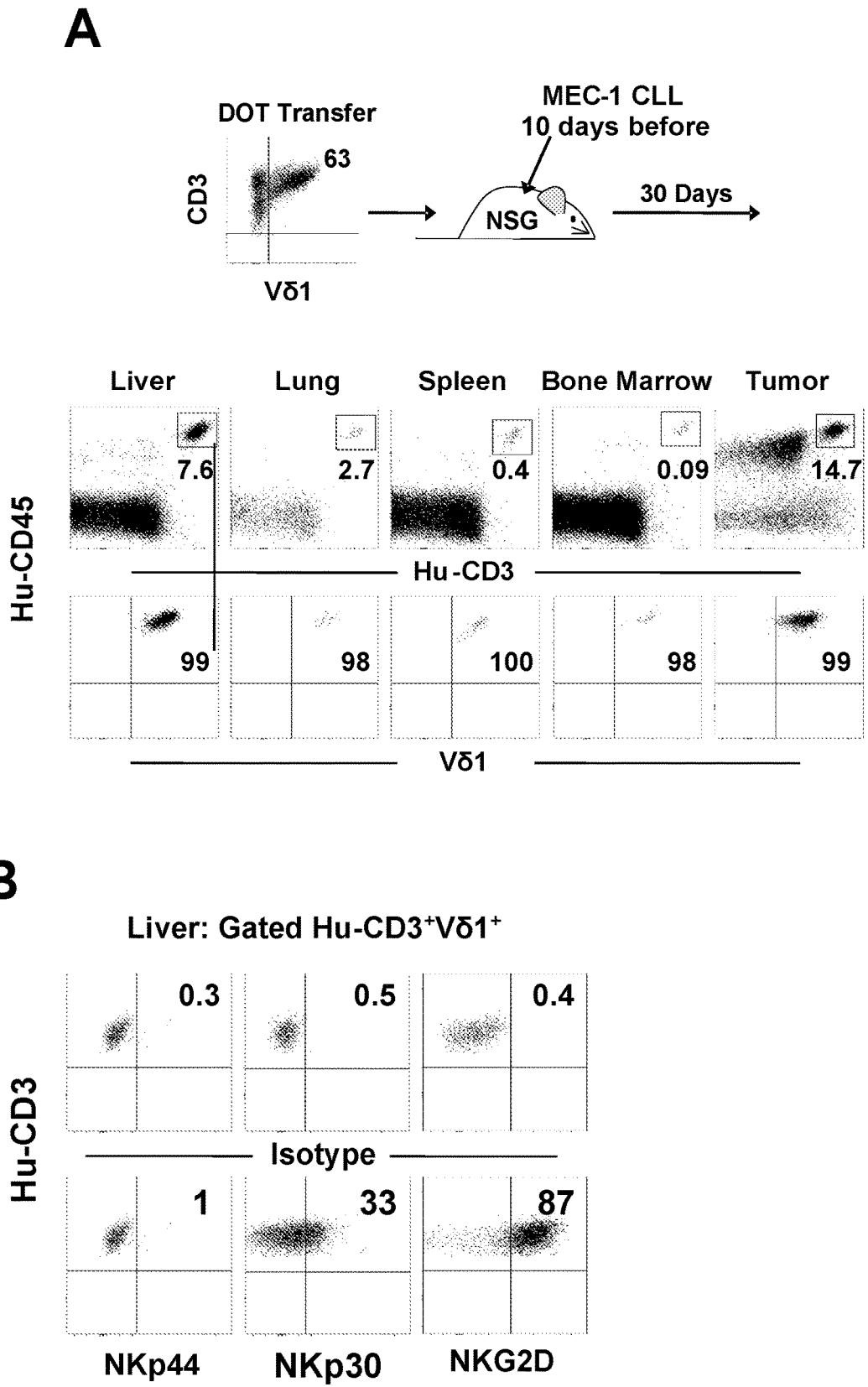
Figure 12C:
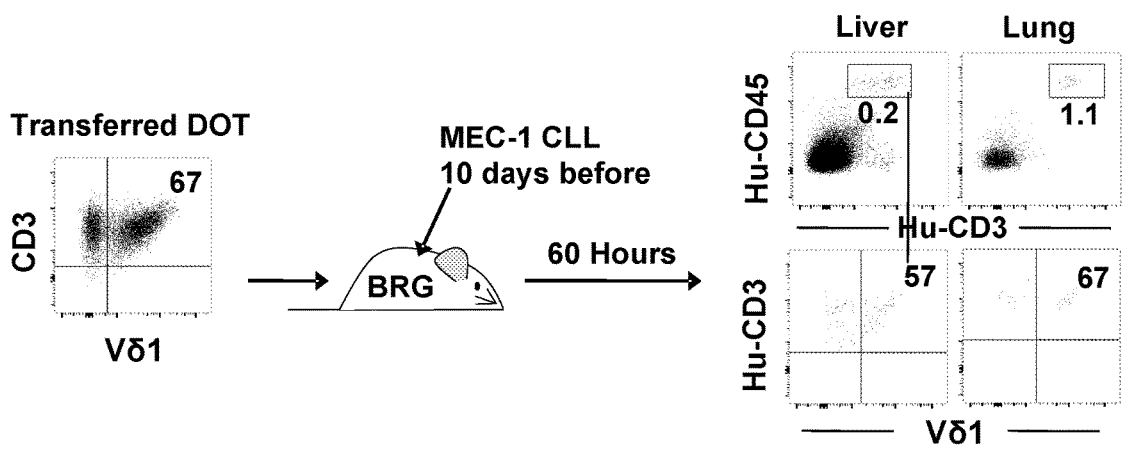

FIGS. 12A, 12B, and 12C show that infused TCRγδ+ T cells home and survive in xenograft tumor models. A. $2 \times 10^7$ TCRγδ+ T cells were transferred into tumor-bearing (MEC-1 CLL\SLL cell-line) NSG immunodeficient hosts. 30 days after transfer of TCRγδ+ T cells, animals were sacrificed and TCRγδ+ T cell-progeny was evaluated by FACS in the indicated tissues. Note that TCRγδ+ T cells were present in all tissues analyzed and also that CD3+ Vδ1+ T cells were highly enriched, suggesting preferential fitness and/or activation in presence of CLL tumor. Dot-Plots are from a representative animal of 6 animals analyzed. B. Infused TCRγδ+ T cells express NCRs in vivo. TCRγδ+ T cells recovered from the liver at day 30 after transfer were analyzed by FACS for NCR expression. Note high expression of NKp30 and NKG2D. Top dot plots are isotype controls. A representative animal of 3 animals analyzed is shown. C. Infused TCRγδ+ T cells are able to home into BRG immunodeficient hosts. $10^7$ TCRγδ+ T cells from a different donor were transferred into CLL tumor-bearing BRG hosts and quantified by FACS 72 hours after transfer.

TCRγδ+ T cells could be recovered from both the lung and liver and TCRVδ1+-expressing cells were found at proportions similar to the initial transfer. One animal out of two is shown.

Figure 13:
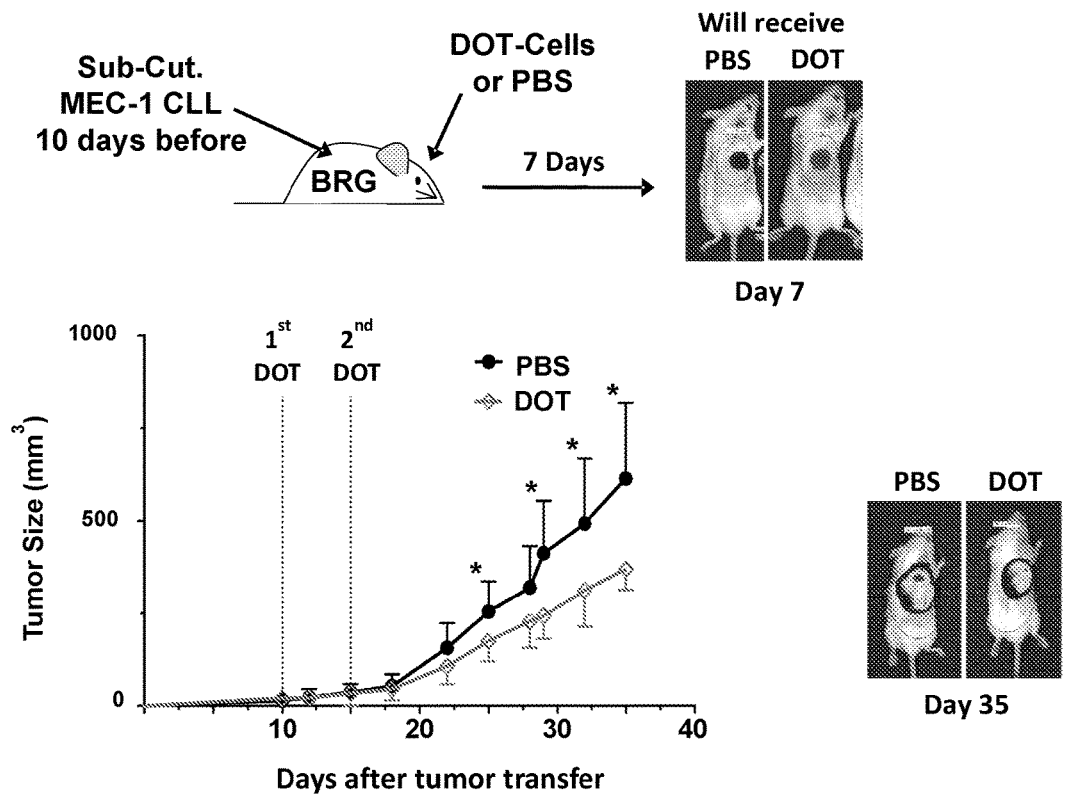
Figure 14A:
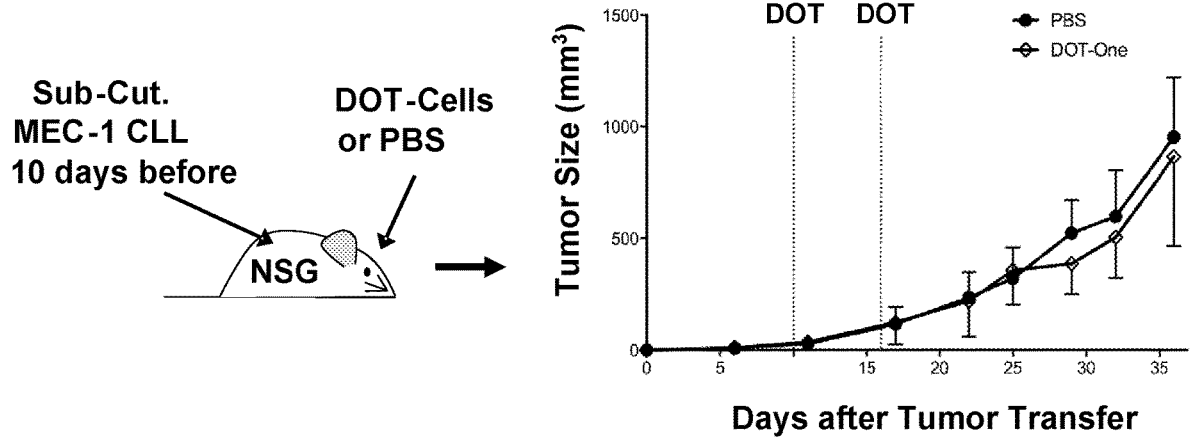
Figure 14B:
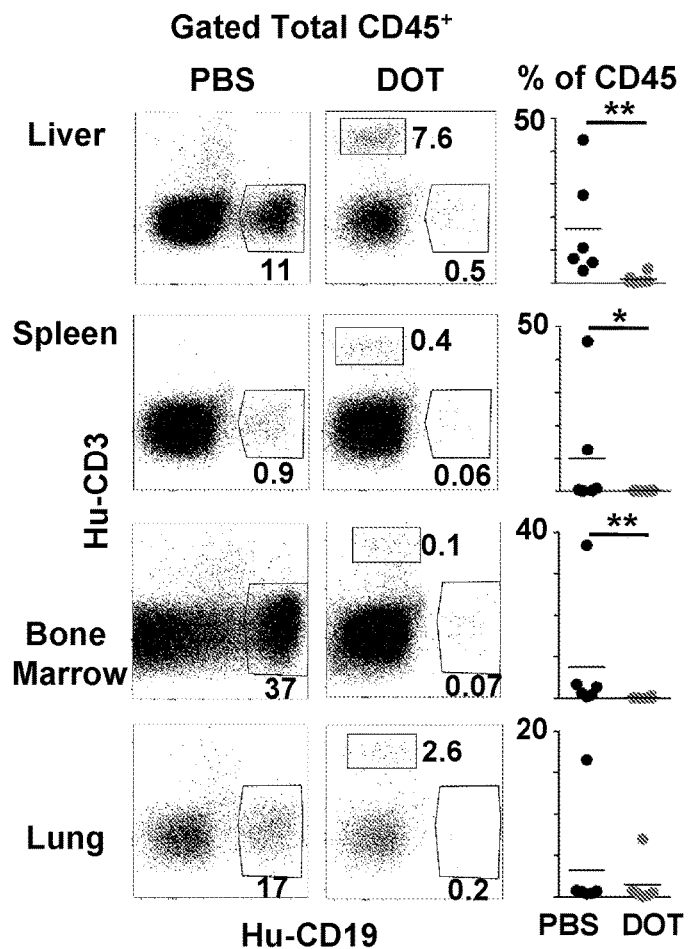
Figure 14C:
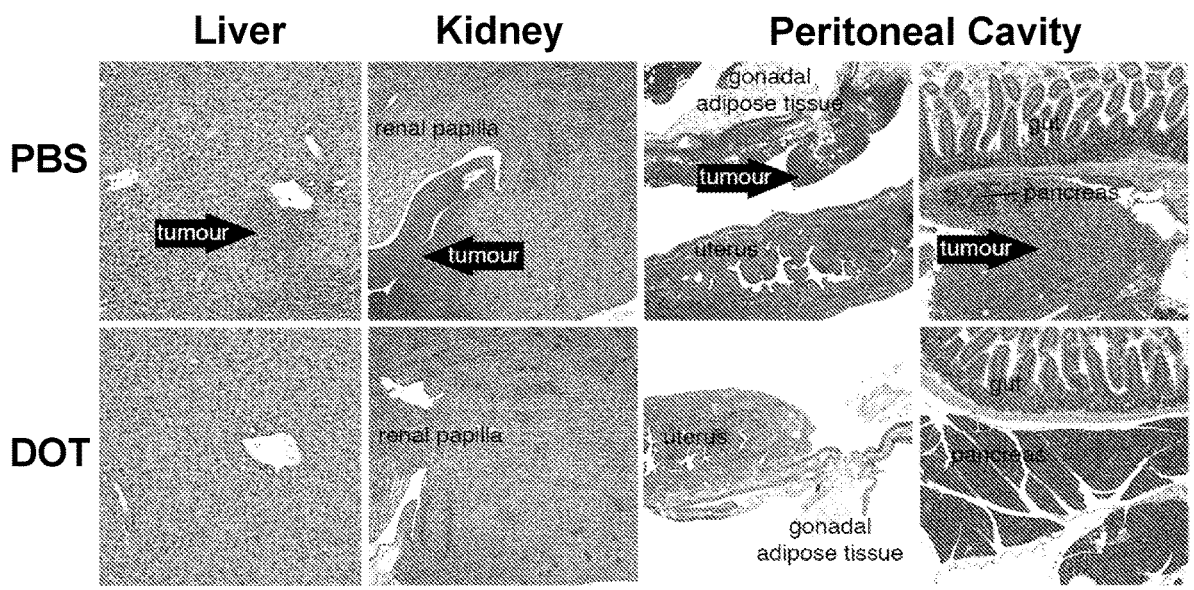
Figure 14D:
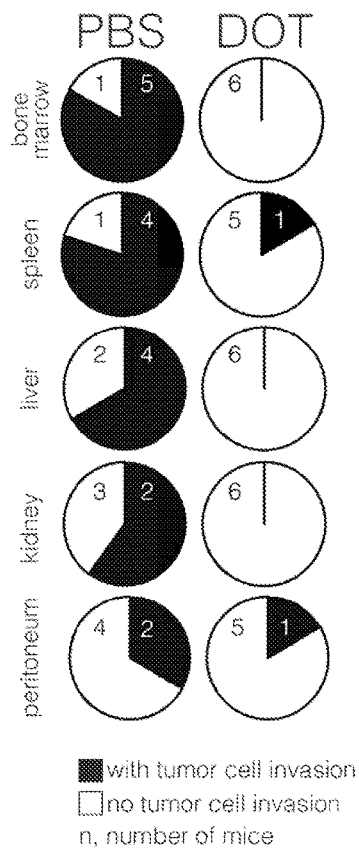

FIG. 13 shows that TCRγδ+ T cells can limit tumour growth in vivo. $10^7$ Luciferase-expressing MEC-1 CLL/SLL tumour cells were transferred subcutaneously into immunodeficient BRG hosts. 10 and 15 days after transfer, $10^7$ TCRγδ+ T cells or control PBS were transferred i.v. into CLL tumour bearing hosts, as verified by luminescence analysis. CLL/SLL tumour growth was periodically measured using a caliper. Tumour size is shown, note the effect of TCRγδ+ T cells visible in CLL tumour size (n=8 mice per group).

FIGS. 14A, 14B, 14C and 14D show that TCRγδ+ T cells limit CLL tumour spread. A. $10^7$ Luciferase-expressing MEC-1 CLL/SLL tumour cells were transferred subcutaneously into immunodeficient NSG hosts. 10 and 15 days after transfer, TCRγδ+ T cells ($2\times10^7$) or control PBS were transferred i.v. into CLL/SLL tumour bearing hosts, as verified by luminescence analysis. CLL/SLL tumour growth was periodically measured using a Caliper. Tumour size is shown, note the partial and transient tendency early upon treatment but TCRγδ+ T cells were not able to limit the faster bulk CLL/SLL tumour growth in these hosts. B-D. The CLL/SLL tumour line is able to spread to other organs in these experiments. Plots shown in B depict FACS analysis of organs recovered at the end of the experiment from NSG hosts receiving TCRγδ+ T cells transfer or control PBS. We observed a generalized reduction in CLL/SLL tumour cells recovered in different organs but this effect was more pronounced in the liver, a major organ for tumour spreading in this model. C. histological (H&E) analysis of a representative animal from each group, showing CLL/SLL tumour metastasis in the indicated anatomical sites of PBS treated animals and absence of tumour infiltrates in treated animals. (*$p<0.05$; **$p<0.01$). D. Summary of histological analysis is shown, depicting animals from each group where CLL/SLL tumour infiltrates were found against animals free of tumour infiltrates. Scoring was performed blindly by a certified pathologist on H&E stained histological samples from the indicated tissues from animals in experiment depicted in FIG. 15. Results are shown for all animals analysed and show a clear reduction in overall tumour spread in the group of animals treated with in vitro expanded TCRγδ+ T cells.

Figures 15A, 15B:
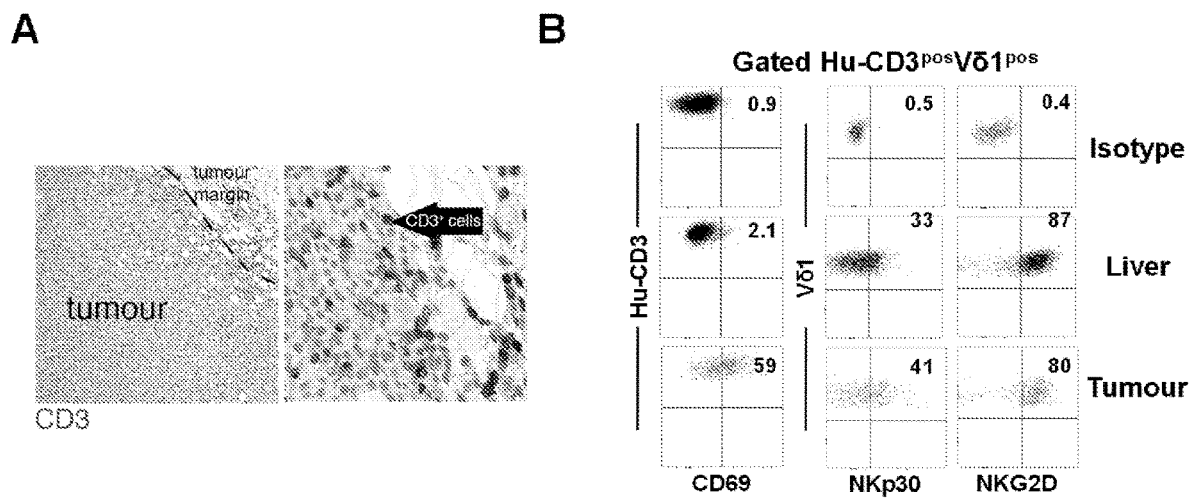

FIGS. 15A and 15B show that TCRγδ+ T cells can infiltrate primary tumour and are activated in vivo. A. Depicted is IHC analysis of CD3-stained sections of primary CLL/SLL tumour from NSG animals transferred with MEC-1 tumour cells and treated with TCRγδ+ T cells. B. We analysed CD69 (n=3, a representative dot-plot is shown), Nkp30 and NKG2D expression (n=2) in vivo in different organs and found recently activated TCRγδ+ T cells, with major expression of these activation markers in TCRγδ+ T cells recovered from the CLL/SLL tumour.

Figures 16A, 16B:
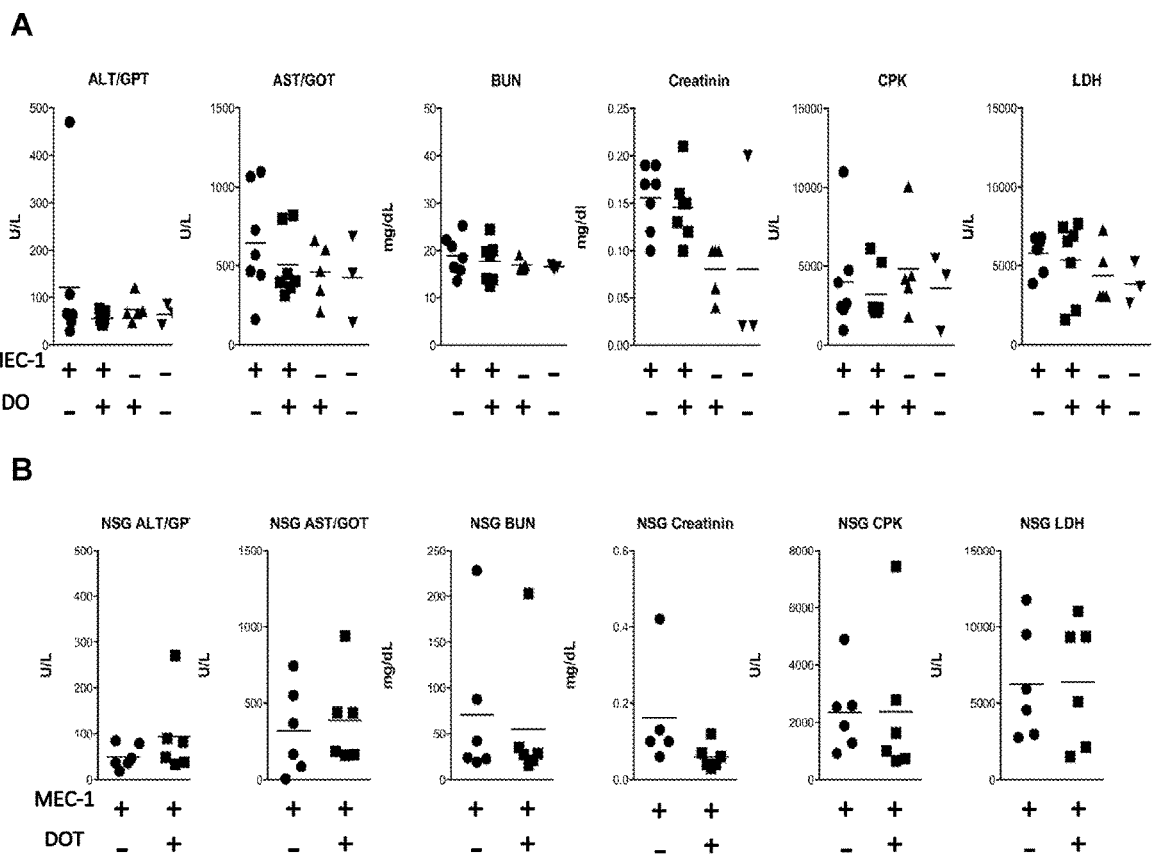

FIGS. 16A and 16B show biochemical analysis of blood samples. (A) Blood was collected at the time of necropsy from animals from experiment shown in FIG. 14 and biochemical analysis performed for Alanin-Aminotransferase (ALT/GPT), Aspartate Aminotransferase (AST/GOT), Blood Urea Nitrogen (BUN), Creatinin, Creatin phosphokinase (CPK) and Lactate Dehiidrogenase (LDH). (B) The same as in A, for animals shown in FIG. 11. We found no evidence for toxicity associated with DOT cell treatment.

Detailed Methods of the In Vivo Studies:

Balb/c Rag$^{-/-}$γc$^{-/-47}$ animals were obtained from Taconic (USA); NOD-SCIDγc$^{-/-48}$ mice were obtained from the Jackson Laboratories (USA). BRG or NSG mice were injected subcutaneously with MEC-1 cells and treated after 6 and 11 days with two intravenous transfers of $10^7$ or $2\times10^7$ DOT cells, and then analyzed (tumor size, histology, flow cytometry of tumor or organ infiltrates, and blood biochemistry) as detailed. All animal procedures were performed in accordance to national guidelines from the Direção Geral de Veterinária and approved by the relevant Ethics Committee. For phenotyping after in vivo DOT-cell transfer, animals were euthanized using Eutasil in order for blood collection via cardiac puncture; and quickly perfused with PBS+ Heparin. Organs were homogenized and washed in 70 μM cell strainers. Femurs were flushed and then filtered. Cells were then stained with the following antibodies from ebioscience, Biolegend, Myltenyi Biotec or Beckton Dickinson: anti-mouse CD45 (30-F11), and anti-Human: CD45 (HI30). Other antibodies used are common with the in vitro studies. Antibodies were coupled to FITC, PE, PerCP, PerCP-Cy5, PE-Cy7, APC, APC-Cy7, Pacific Blue, Brilliant Violet 421 and Brilliant Violet 510 fluorochromes. Statistical analysis was performed using Graphpad-Prism software. Sample means were compared using the unpaired Student's t-test. In case variances of the two samples were found different using F-test, the data was log transformed and if variances were then found not to be different, the unpaired t-test was applied to the log-transformed data. For Survival data, log-rank (Mantel-Cox) test was used.

In vivo experimental design: We used a previously described model of xenografted human CLL upon subcutaneous adoptive transfer of CLL/SLL-derived MEC-1 cells into Balb/cRag$^{-/-}$γc$^{-/-}$ (BRG) animals, which we further adapted using NOD-SCIDγc$^{-/-}$ (NSG) animals as hosts. In order to ensure that animals receiving treatment or PBS control were tumor-bearing animals, we transduced MEC-1 CLL cells with firefly-luciferase in order to detect and measure tumor engraftment at early time-points before ascribing treatment cells. After 7 or 4 days (in different studies) we injected luciferin i.p. to determine tumour load as a function of luminescence, before ascribing treatment (or PBS control) to the animals. Animals were distributed randomly in cages and assigned to each treatment (PBS or DOT-Cells) according to luminescence measured at day 7, in such a way that animal with highest luminescence received treatment, second highest received PBS, third highest received treatment, etc. This resulted in a non-randomized distribution into groups but randomized distribution in the different cages. 2 additional animals received DOT-Cells in the indicated experiments for initial homing analysis. We performed two $10^7$ or $2\times10^7$ DOT-Cells transfers (within 5 days), using cells from one different donor per experiment. Tumor was measured using a Caliper and taking three perpendicular measurements. The formula used was ½×L× W×H.[49] Animals were sacrificed when tumor measurements reached 1000 mm$^3$.

Luminescence Analysis: After transduction of MEC-1 Cell line with GFP-firefly luciferase, growing cells were screened and sorted according to GFP expression using a FACS-Aria (Becton Dickinson, USA), up to >95% GFP positive cells. These cells were then kept in culture until transferred subcutaneous into host animals (in 50 μl PBS). At the indicated time points after transfer, animals were anesthetized (Ketamin/Medetomidine) and Luciferin was injected (i.p.). 4 min later luciferase activity was detected and acquired using IVIS Lumina (Calliper LifeSciences) at the IMM bioimaging facilities. Anesthesia was then reverted and animals returned to previous housing.

Lymphocyte counts: Cell counts were performed with a hemocytometer or using Accuri Flow cytometer (Becton Dickinson, USA). Counts per organ were estimated when parts of the organ were sampled for histological analysis by weighting organs before and after the samples were split. Numbers presented are then corrected for the whole organ. In Bone Marrow data, absolute numbers were calculated and are displayed for one femur. Histopathology and Immunohistochemistry: Mice were sacrificed with anesthetic overdose, necropsies were performed and selected organs (lung, heart, intestine, spleen, liver, kidney, reproductive tract, brain, cerebellum, spinal cord, and femur) were harvested, fixed in 10% neutral-buffered formalin, embedded in paraffin and 3 μm sections were stained with hematoxylin and eosin (H&E). Bones were further decalcified in Calci-Clear™ (Fisher Scientific) prior to embedding. Tissue sections were examined by a pathologist, blinded to experimental groups, in a Leica DM2500 microscope coupled to a Leica MC170 HD microscope camera. Immunohistochemical staining for CD3 (Dako, cat. no. A0452) was performed by the Histology and Comparative Pathology Laboratory at the IMM, using standard protocols, with a Dako Autostainer Link 48. Antigen heat-retrieval was performed in DAKO PT link with low pH solution (pH 6), and incubation with ENVISION kit (Peroxidase/DAB detection system, DAKO, Santa Barbara, Calif.) was followed by Harri's hematoxylin counterstaining (Bio Otica, Milan, IT). Negative control included the absence of primary antibodies; and CD3 staining was not observed in the negative controls. Images were acquired in a Leica DM2500 microscope, coupled with a Leica MC170 HD microscope camera.

Mouse Blood Biochemistry: Mice were deeply anaesthetised and blood was collected from the heart to heparin-coated tubes, sent for analysis of biochemical parameters shown at an independent laboratory. Biochemical parameters were measured in serum, in a RX monaco clinical chemistry analyser (RANDOX).

Figure 17:
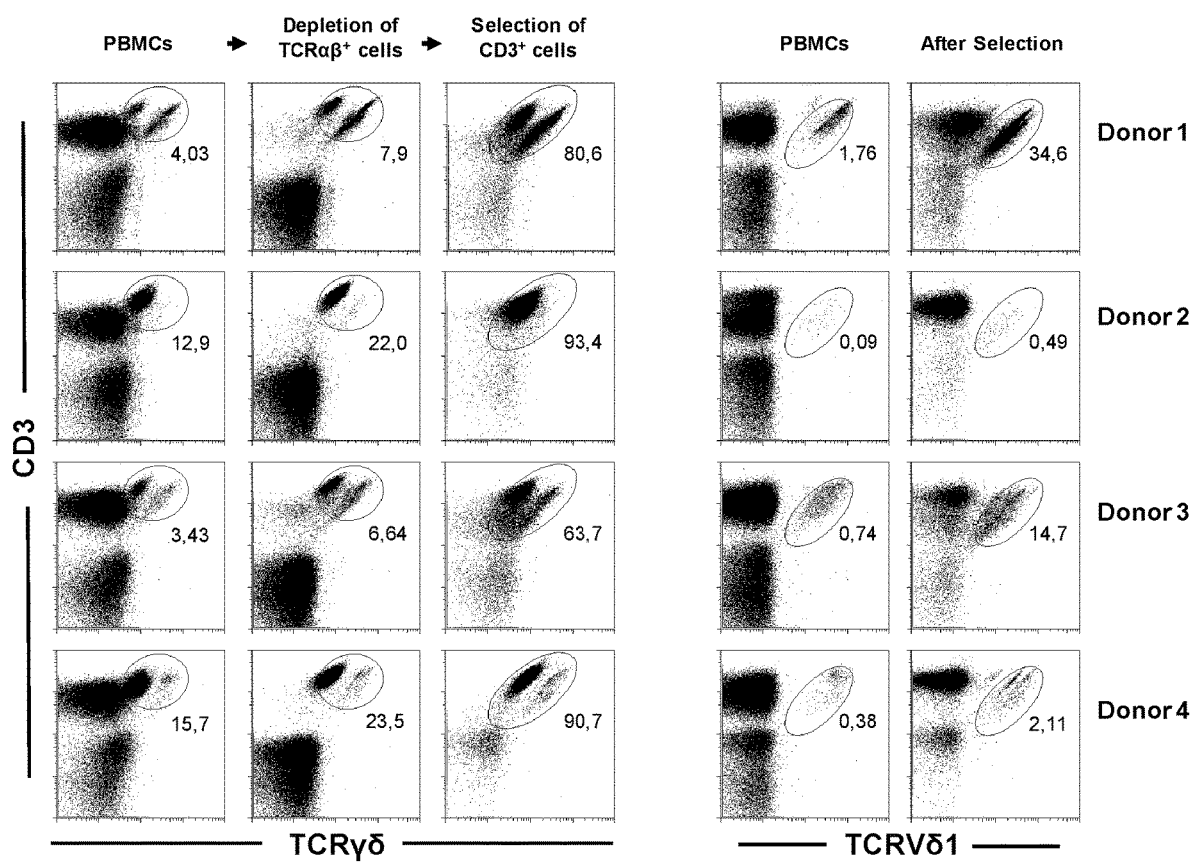

FIG. 17 shows TCRγδ$^+$ PBL enrichment after two-step MACS-sorting.

Peripheral blood (obtained from buffy coats) was collected from 4 healthy volunteers, and total TCRγδ$^+$ T cells were isolated by MACS: first, TCRαβ depletion was performed and then CD3$^+$ cells were positively selected. Cells were stained for TCRγδ, CD3 and TCRVδ1 and analyzed by flow cytometry. Dot plots show fractions of TCRγδ$^+$ PBLs before and after each MACS-sorting step (left panels); and initial and final percentages of Vδ1$^+$ T cells (right panels).

Figure 18A:
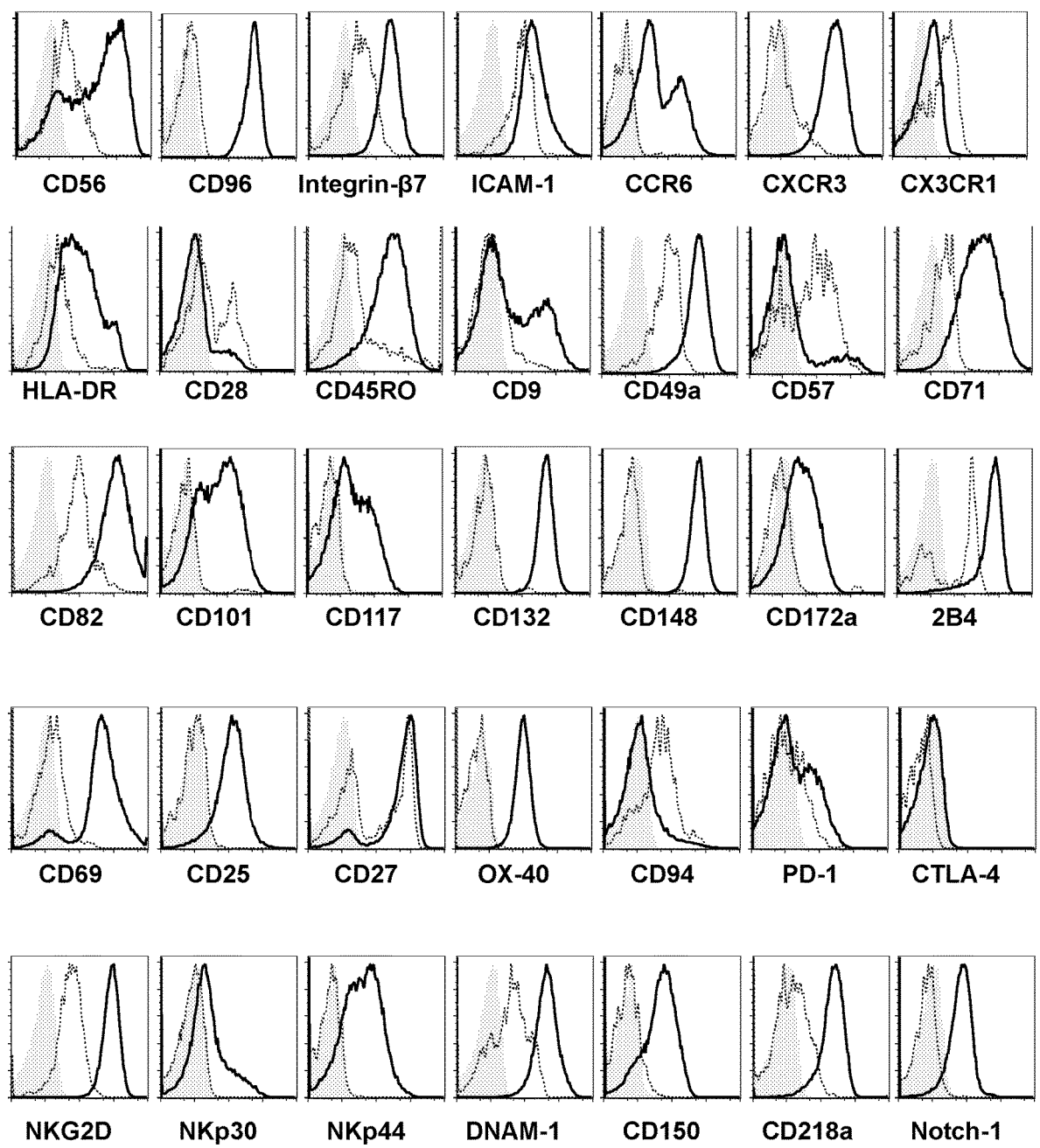

FIG. 18 shows the characterization of the activation and maturation phenotype of the obtained Vδ/1$^+$ T cells.

(A) Flow cytometry comparison of the cell surface phenotype of Vδ1$^+$ T cells at day 21 of culture (using the previously described 2-step culture protocol); (full lines) with freshly-isolated Vδ1$^+$ T cells (dotted lines), as analyzed using the LEGENDScreen kit (Biolegend). Shown are histogram overlays for several markers related to lymphocyte activation and differentiation, and markers implicated in adhesion and migration. Cells from one healthy donor are shown. (B) Heatmap representing percentages of positive cells for each surface marker across cultured Vδ1$^+$ T cells (at day 21 of culture) produced from 4 different healthy donors (Cultur. 1-4), compared to freshly-isolated Vδ1$^+$ T cells (from donors 1 and 2). The color code is presented on the right. For phenotyping after cell production: cells were stained with anti-CD3-APC (clone UCHT1), anti-TCRVδ1-FITC and a panel of receptors using the LegendScreen kit (Biolegend).

Figure 19:

FIG. 19 shows TCR/NCR-dependent cytotoxicity of TCRγδ$^+$ T cells against leukemic (but not healthy) cells.

Expanded and differentiated TCRγδ$^+$ T cells produced from two healthy donors (using the previously described 2-step culture protocol), were tested in different experiments against MEC-1 (CLL) target cells at increasing effector/target ratios (left plot, gray bars) and also in presence of blocking antibodies for (α, anti-) the indicated molecules, either individually (Expt 1) or in combinations (Expt 2). The highest Effector/Target ratio (10:1) was used in blocking experiments and gray bar at this ratio (with IgG isotype antibody) serves as control. Shown are the percentages of dead (Annexin-V$^+$) MEC-1 target cells. * and # indicate significant differences relative to IgG isotype control or α-TCRVδ1, respectively (Mean+SD; *, #p<0.05; **, ##p<0.01; Student's t-test).

For cytotoxicity assays, MEC-1 tumor cells were cultured in T25 flasks in complete 10% RPMI 1640 with 10% Fetal Bovine Serum, 2 mM L-Glutamine and maintained at 10$^5$ up to 10$^6$ cells/mL by dilution and splitting in a 1:3 ratio every 3-4 days. In vitro expanded TCRγδ$^+$ T cells were plated in 96-well round-bottom plates. Tumor cells were stained with CellTrace Far Red DDAO-SE (1 μM; Molecular Probes, Invitrogen) and incubated at the indicated target:effector ratio with TCRγδ$^+$ T cells in RPMI 1640 medium for 3 hours at 37° C. and 5% CO$_2$, in the presence of 70 ng/ml IL-15. For receptor blocking, γδ PBLs were pre-incubated for 1 hour with blocking antibodies: human anti-TCRγδ (clone B1); human anti-NKG2D (clone 1D11); human anti-CD2 (clone RPA-2.10); human anti-CD3 (clone OKT-3); human anti-NKp30 (clone P30-15); human anti-NKp44 (clone P44-8), mouse IgG1,k (clone MOPC-21), mouse IgG2b (clone MPC-11), mouse IgG3k (clone MG3-35), all from Biolegend. Human anti-CD226 (clone DX11) was from BD Biosciences. Human anti-Vδ1 TCR (clones TCS-1 or TS8.2) were from Fisher Scientific, and human anti-TCRγδ (clone IMMU510) was from BD Biosciences. The blocking antibodies were maintained in the culture medium during the killing assays.

Finally, all cells were then stained with Annexin V-FITC (BD Biosciences) and analyzed by flow cytometry.

Figure 20:
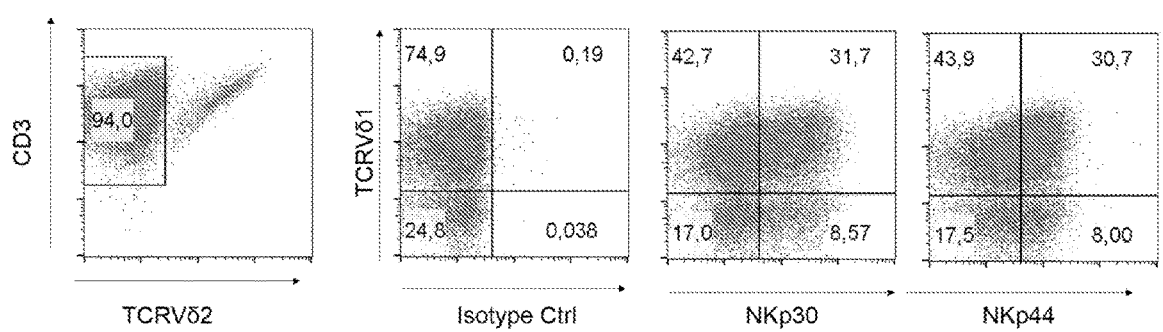

FIG. 20 shows the expression of activating cell surface NK receptors in in vitro expanded Vδ1$^+$ and Vδ1$^-$ Vδ2$^-$ T cells. Expanded and differentiated TCRγδ$^+$ T cells were produced from healthy donors, using the previously described 2-step culture protocol. Shows expression of the activating receptors NKp30 and NKp44 in CD3$^+$ Vδ1$^+$ cells and in CD3$^+$ Vδ1$^-$ Vδ2$^-$ T cells after 21 days of culture. First, CD3$^+$ Vδ2$^+$ cells were identified (with anti-CD3 and anti-Vδ2 mAbs conjugated to fluorochromes) and were excluded from the analysis. The remaining CD3+ cells were analyzed for the expression of Vδ1 and NKp30, NKp44 and Isotype Control. Shows representative results of 4 independent experiments with 4 different donors.

Figure 21:
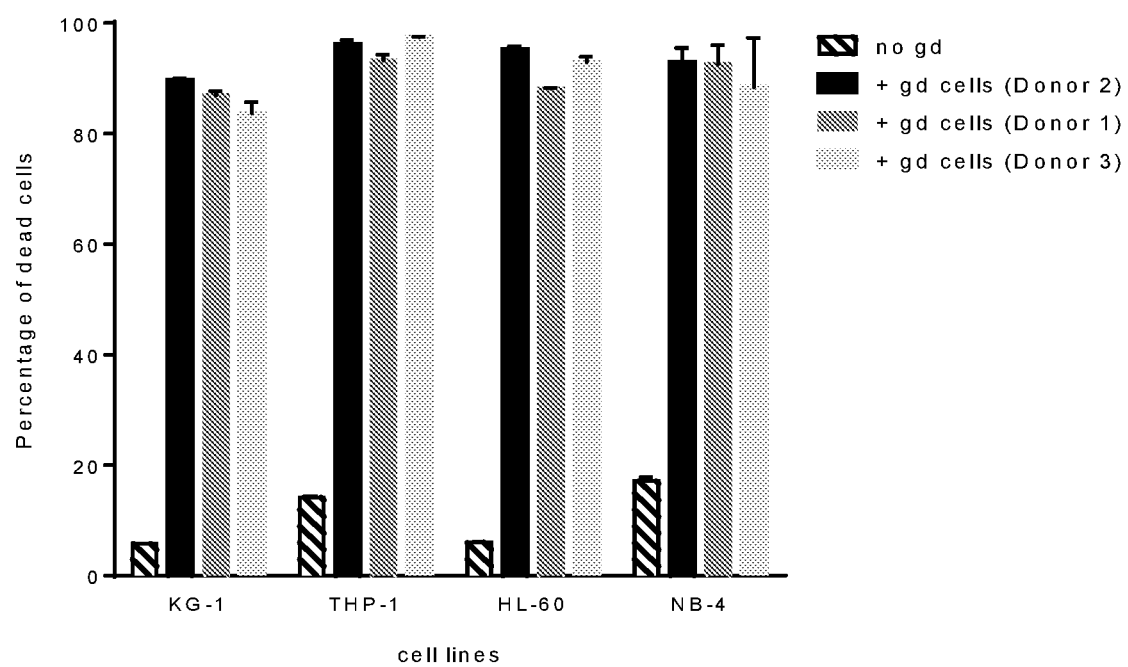

FIG. 21 shows cytotoxicity of the expanded Vδ1$^-$ Vδ2$^-$ T cell subset of TCRγδ$^+$ T cells against leukemic cells.

Expanded and differentiated TCRγδ$^+$ T cells produced from one healthy donor (using the previously described 2-step culture protocol) were stained for CD3, Vδ1 and Vδ2 T cell markers with monoclonal antibodies conjugated to fluorochromes, and the CD3$^+$ Vδ1$^-$ Vδ2$^-$ T cell population was isolated by flow cytometry. Isolated cells were then tested in a killing assay in vitro against acute myeloid leukemia (AML) target cell lines (KG-1, THP-1, HL-60 and NB-4) at an effector/target ratio of 10:1. The killing assay was performed as previously described.

Tables:

Table 1 describes the molecules used to stimulate the proliferation of Vδ1+ T cells during the optimization stage. Reagents were used at a concentration range from 0.1 ng/ml to 80 μg/ml. The column on the right shows reagent distributor or manufacturer.

Table 2 shows a summary of tested culture conditions. TCRγδ+ PBLs were isolated by MACS from a healthy donor and cultured at 1 million cells/ml in 96 well plates, at 37° C. and 5% $CO_2$. Cells were expanded in complete medium (Optmizer CTS, GIBCO) supplemented with 5% autologous plasma, 1 mM L-glutamine and with the described growth factors. At the end of the culture period, cells were counted and cell phenotype was analyzed by flow cytometry. Shows selected results of 4 consecutive experiments. The best culture conditions in each experiment are ranked by fold increase. Fold expansion rate of Vδ1+ T cells was calculated as: (absolute number of Vδ1+ T cells at the end of the culture)/(absolute number of Vδ1+ T cells at day 0 of culture). Shows representative results of 2 independent experiments.

Table 3 shows a summary of tested culture conditions. TCRγδ+ PBLs were isolated by MACS from a healthy donor and cultured for 14 days in the presence of the described growth factors. At day 14 of culture, cells were split: one fraction of cells was cultured as before, while the other fraction of cells was cultured in the absence of IL-4 and in the presence of the indicated growth factors. At day 21, cells were counted and cell phenotype was analyzed by FACS. Shows representative results from 2 independent experiments. A cytotoxicity assay was also performed at day 21 using the generated TCRγδ+ cells against MOLT-4 leukemia targets (method is described in FIG. 8). Apoptotic (dying) target cells were detected by positive staining with Annexin-V reagent in a Fortessa II flow cytometry machine (BD Biosciences). Basal tumor cell death (i.e., the percentage of apoptotic tumor cells in tumor samples that were not co-cultured with TCRγδ+ cells) was 10±3%. Shows average of two technical replicates.

Table 4 shows a summary of tested culture conditions. TCRγδ+ PBLs were isolated by MACS from a healthy donor and cultured for 15 days in a two-step and three-step culture protocols, in the presence of the described growth factors. Cells were counted and cell phenotype was analyzed by FACS at the end of the culture period. Shows representative results of 2 independent experiments.

Table 5 shows a summary of tested culture conditions. TCRγδ+ PBLs were isolated by MACS from a healthy donor in a two-step protocol and cultured for 21 days in the presence of the described growth factors. Cells were counted and cell phenotype was analyzed by FACS at the end of the culture period. Shows representative results of 2 independent experiments Table 6 shows the purity and phenotype of TCRγδ+ PBLs isolated via a two-step MACS protocol. PBMCs were obtained by density gradient centrifugation in ficoll from Buffy Coat products collected from 8 healthy donors. TCRγδ+ T cells were further isolated by a two-step MACS protocol as described in FIG. 2. Cell phenotype was characterized by flow cytometry analysis of cell surface antigens. Data correspond to percentages of total live cells.

Table 7 shows the purity and phenotype of in vitro expanded TCRγδ+ T cells. MACS-sorted TCRγδ+ T cells from healthy donors (same as in Table 6) were cultured for 21 days in cell culture bags, according to the previously described two-step culture protocol. Cell populations were characterized by flow cytometry. Indicates percentages of TCRγδ+ T cells and contaminant cells, relative to total live cells present in the cultures.

Table 8 shows the expression of NCRs and NKG2D in freshly-isolated versus cultured Vδ1+ T cells. Expression of the activating receptors NKp30, NKp44 and NKG2D in CD3+ Vδ1+ T cells after 16 or 21 days of cytokine and anti-CD3 mAb treatment. Data in this table are representative of data obtained from 10 independent donors, noting that NKp30 and NKp44 expression varied between around 10% and 70% among different donors, while NKG2D was expressed by more than 80% of Vδ1+ PBLs of all tested donors.

Table 9 shows the purity and phenotype of pre- and post-MACS-sorted TCRγδ+ PBLs from CLL/SLL patients. B-cell chronic lymphocytic leukemia (CLL) cells were obtained from the peripheral blood of patients at first presentation, after informed consent and institutional review board approval. TCRγδ+ T cells were MACS-sorted from the peripheral blood of 3 CLL patients (CLL-1-3) and cell population phenotype was characterized by flow cytometry analysis of cell surface antigens. Shows percentages of TCRγδ+ T cells and contaminant cells, obtained immediately before and after the 2-step magnetic isolation procedure. Each cell subset was gated on total live cells.

Table 10 shows that contaminant autologous B-CLL cells become a residual population in culture. TCRγδ+ T cells were MACS-sorted from the peripheral blood of 3 CLL/SLL patients (CLL-1-3; as in Table 9) and cultured in vitro for 16 days as previously described. Cell population phenotype was characterized by flow cytometry analysis of cell surface antigens. Shows percentages of TCRγδ+ T cells and contaminant cells. Each cell subset is gated on total live cells, except NKp30 and NKG2D expression that were gated on Vδ1+ T cells.

Table 11 shows in more detail the tested culture conditions presented in Table 2 of a previous application. TCRγδ+ PBLs were isolated by MACS from a healthy donor and cultured at 1 million cells/ml in 96 well plates, at 37° C. and 5% $CO_2$. Cells were expanded in complete medium (Optmizer CTS, GIBCO) supplemented with 5% autologous plasma, 1 mM L-glutamine and with the described growth factors. At the end of the culture period, cells were counted and cell phenotype was analyzed by flow cytometry. Shows selected results of 4 consecutive experiments (the same experiments described in Table 2 of a previous application, but further discloses results of parallel control culture conditions, marked with an asterisk, for a more complete understanding of the results). It also shows the percentage of NKp30+ Vδ1+ T cells obtained with each condition. Culture conditions in each experiment were ranked by fold increase. Fold expansion rate of Vδ1+ T cells was calculated as: (absolute number of Vδ1+ T cells at the end of the culture)/(absolute number of Vδ1+ T cells at day 0 of culture). Shows representative results of 2 independent experiments.

Table 12 shows a summary of tested culture conditions. TCRγδ+ PBLs were isolated and expanded from a healthy donor, as described previously, in the presence of the indicated growth factors. Shows selected results of one experiment with multiple culture conditions. To better understand the effects of IL15/IL-2/IL-7 and IFN-γ on cultured TCRγδ+ cells, TCRγδ+ cells were cultured in culture medium and three different concentrations of IL-4 and anti-CD3 mAb, in the presence or absence of IL15/IL-2/IL-7 and IFN-γ. Shows the detrimental effect of IL-15, IL-2 and IL-7 on TCRγδ+ T cell expansion, when these cells were cultured in the presence of IL-4 and IFN-γ. Shows representative results of 2 independent experiments.

Table 13 shows the total absolute number of TCRγδ+ cells obtained before and after the large-scale 2-step cell culture protocol. MACS-sorted peripheral blood TCRγδ+ cells obtained from healthy donors (represented in FIG. 6) were counted with a haemocytometer before and after cell culture expansion/differentiation. Each Buffy Coat was concentrated from 450 ml of peripheral blood and contained around 450-550 million PBMCs. On average, 17 million TCRγδ+ T cells could be collected by MACS from each Buffy Coat. However, in future clinical applications, starting samples will be Leukapheresis products that contain larger numbers of cells and are collected by an Apheresis machine. In previous studies, unstimulated leukapheresis products collected from leukemia patients contained on average $13.4 \times 10^9$ (range $4.4$-$20.6 \times 10^9$) peripheral blood cells, of which around 160 million TCRγδ+ T cells (range $1.0$-$3.0 \times 10^8$) were obtained after MACS (Wilhelm, M., et al., *Successful adoptive transfer and in vivo expansion of haploidentical gammadelta T cells*. J Transl Med, 2014. 12: p. 45.). This represents, on average, about 9 times more initial cells than what was obtained with Buffy Coats. Consequently, the average estimated number of cells that would be generated in the same culture system if leukapheresis products were used as starting sample is about $10.2 \times 10^9$ cells (range: $3.9 \times 10^9$ $14.4 \times 10^9$ cells).

Table 14 shows reagents and materials used to produce pharmaceutical grade TCRγδ+ T cells.

Examples

Optimization of the Ex-Vivo Expansion of Human Vδ1+ TCRγδ+ T Cells

The inventors performed a series of experiments aiming to improve the expansion and purity levels of in vitro cultured Vδ2− γδ T cells. Since there was no commercially available antibody against the Vδ3+ chain of the TCR, an anti-TCRVδ1 mAb was used to identify Vδ1+ T cells in cell samples, during the culture optimization stage. TCRγδ+ PBLs from a panel of healthy donors were isolated by MACS and tested for their reactivity to in vitro stimulation with IL-2 and PHA (i.e., detectable changes in cell activation and proliferation). One donor with reactive Vδ1+ PBLs was selected to provide blood samples for the rest of the optimization study. The preference for a fixed healthy donor was important, since a more reliable comparison could be performed between results obtained in different experiments. The selected donor had a normal (but high) percentage of TCRγδ+ T cells in the peripheral blood (10%-12% of total PBLs), although a very low percentage of Vδ1+ PBLs (0.3% of total PBLs, or 3.0% of total TCRγδ+ T PBLs; FIG. 1). He was considered a suitable donor to use in these experiments since every minor improvement in the final number and purity levels of cultured Vδ1+ T-cells could be readily detected by flow cytometry.

The single-step MACS protocol used to isolate TCRγδ+ T cells from PBMCs was very efficient, generating highly pure cell populations (FIG. 1). However, one critical reagent (i.e., the human anti-TCRγδ mAb conjugated with magnetic microbeads, from Miltenyi Biotec) is not currently approved for clinical applications. The clinical-grade production, validation and regulatory approval of such reagent can take many years, and this problem will prevent any immediate use of the described protocol in clinical applications. A different, but equivalent method for isolating TCRγδ+ T cells was then developed and adopted. The process consisted of two steps of magnetic cell separation, as described in FIG. 2. The final purity levels of the obtained TCRγδ+ T cells were lower than with the previous (single-step) method, but still acceptable for cell culture. Importantly, this new cell isolation method used only reagents already approved for clinical applications (manufactured by Miltenyi Biotec GmbH, Germany).

The inventors then tested multiple combinations of clinical-grade agonist antibodies and cytokines for their capacity to expand and differentiate (over 2-3 weeks) Vδ1+ T cells from the peripheral blood. MACS-sorted TCRγδ+ PBLs collected from the previously selected healthy donor were incubated in culture medium for 2-3 weeks in 96-well plates, at 37° C. and 5% $CO_2$, in the presence of 58 different T/NK cell activating molecules (Table 1). These included 13 different TCR agonists, 23 different co-receptor agonists, and 22 different cytokines, which were tested in 2.488 different combinations and concentrations. Antibodies were used in both soluble and plastic-bound presentations. Cytokines were tested at a concentration range from 0.1 ng/ml to 1000 ng/ml; TCR agonists were used at 0.1 ng/ml to 40 μg/ml, and co-receptor agonists were used at final concentration 0.5 μg/ml to 80 μg/ml.

Several sequential cell isolation and cell culture expansion experiments were performed from the same donor; each experiment testing the effect of about 100-400 different combinations of activating molecules. The optimization started from the basic, non-optimized cocktail (i.e., culturing TCRγδ+ T cells in the presence of IL-2 and PHA). Fresh medium containing the same chosen cocktail of activating molecules was added every 5 days. After 14 days, cells were collected and their phenotype was analyzed by flow cytometry. The best culture condition of each experiment was identified (for the highest fold expansion of Vδ1+ T cells), and selected for further optimization, combined to all available reagents, tested at various concentrations. Fold expansion and purity levels of Vδ1+ T cells gradually increased during the optimization stage, after each superior culture condition was obtained.

Results of experiments 1-4 are summarized in Table 2. Experiment no. 1 confirmed previous observations that IL-4 is a key growth factor in promoting Vδ1+ T cell proliferation and enrichment in culture.[27, 42] In this experiment, the inventors tested the activity of 22 different cytokines on cultured TCRγδ+ T cells, in the presence of a T cell mitogen and IL-2. Clearly, IL-4 was unique in the ability to induce a strong enrichment and expansion of these cells. In contrast, the use of increasing concentrations of IL-2, or the combination of IL-2 with different T cell mitogens, did not produce an equivalent effect, most probably because of increased activation-induced-cell-death (AICD) of cultured cells (conditions 2-3; Table 2).

TABLE 1

| TCR agonists | Monoclonal antibodies (soluble and plate-bound) | anti-human TCR Vδ1 mAb (Clone TS8.2); purified | Thermo Fisher Sci. |
|---|---|---|---|
| | | anti-human TCR δTCS-1 mAb (Clone TS-1); purified | Thermo Fisher Sci. |
| | | anti-human TCR PAN γδ mAb (Clone IMMU510); purified | Beckman Coulter |
| | | anti-human CD3 mAb (Clone OKT3); purified | BioXcell/ Biolegend |
| | Plant lectins (soluble) | Lectin from *Phaseolus vulgaris* (red bean; PHA-P), pur. | Sigma-Aldrich, Co. |
| | | Concanavalin A (from *Canavalia ensiformis*; Con-A), pur. | |
| | | Lectin from *Phytolacca americana*; purified | |
| | | Lectin from *Triticum vulgaris* (wheat); purified | |
| | | Lectin from *Lens culinaris* (lentil); purified | |

TABLE 1-continued

|  |  |  |  |
|---|---|---|---|
|  |  | Lectin from *Glycine max* (soybean); purified |  |
|  |  | Lectin from *Maackia amurensis*; purified |  |
|  |  | Lectin from *Pisum sativum* (pea); purified |  |
|  |  | Lectin from *Sambucus nigra* (elder); purified |  |
| Co-receptor agonists | Monoclonal antibodies (soluble and plate-bound) | anti-human CD2 mAb (Clone S5.2); purified | BD Biosciences |
|  |  | anti-human CD6 mAb (Clone UMCD6/3F7B5); purified | Ancell Corporation |
|  |  | anti-human CD9 mAb (Clone MEM-61); purified | Exbio Praha, a.s. |
|  |  | anti-human CD28 mAb (Clone CD28.2); purified | Biolegend |
|  |  | anti-human CD43 mAb (Clone MEM-59); purified | Exbio Praha, a.s. |
|  |  | anti-human CD94 mAb (Clone HP-3B1); purified | Santa Cruz Biotech |
|  |  | anti-human CD160 mAb (Clone CL1-R2); purified | Novus Biologicals |
|  |  | anti-human SLAM mAb [Clone A12(7D4)]; purified | Biolegend |
|  |  | anti-human NKG2D mAb (Clone 1D11); purified | Exbio Praha, a.s. |
|  |  | anti-human 2B4 mAb (Clone C1.7); purified | Biolegend |
|  |  | anti-human HLA-A, B, C mAb (Clone W6/32); purified | Biolegend |
|  |  | anti-human ICAM-3 mAb (Clone MEM-171); purified | Exbio Praha, a.s. |
|  |  | anti-human ICOS mAb (Clone C398.4A); purified | Biolegend |
|  | Recombinant proteins (soluble) | Human SECTM-1/Fc Chimera (CD7 ligand) | R&D Systems |
|  |  | Human CD26 (Dipeptidyl Peptidase IV) | Sigma-Aldrich, Co. |
|  |  | Human CD27L (CD27 ligand); | PeproTech, inc. |
|  |  | Human CD30L (CD30 ligand); | PeproTech, inc. |
|  |  | Human CD40L (CD40 ligand); | PeproTech, inc. |
|  |  | Human OX40L (OX40 ligand); | PeproTech, inc. |
|  |  | Human 4-1BBL (4-1BB ligand) | PeproTech, inc. |
|  |  | Human ICAM-1 | PeproTech, inc. |
|  |  | Human Fibronectin | Sigma-Aldrich, Co. |
|  |  | Human Hydrocortisone | Sigma-Aldrich, Co. |
| Cytokines | Recombinant proteins (soluble) | Human IFN-γ (Interferon-γ); | PeproTech, inc. |
|  |  | Human TGF-β (Transforming growth factor beta); | PeproTech, inc. |
|  |  | Human IL-1-β (interleukin-1β); | PeproTech, inc. |
|  |  | Human IL-2 (interleukin-2); | PeproTech, inc. |
|  |  | Human IL-3 (interleukin-3); | PeproTech, inc. |
|  |  | Human IL-4 (interleukin-4); | PeproTech, inc. |
|  |  | Human IL-6 (interleukin-6); | Biolegend |
|  |  | Human IL-7 (interleukin-7); | PeproTech, inc. |
|  |  | Human IL-9 (interleukin-9); | PeproTech, inc. |
|  |  | Human IL-10 (interleukin-10); | PeproTech, inc. |
|  |  | Human IL-12 (interleukin-12); | PeproTech, inc. |
|  |  | Human IL-13 (interleukin-13); | PeproTech, inc. |
|  |  | Human IL-15 (interleukin-15); | PeproTech, inc |
|  |  | Human IL-18 (interleukin-18); | Southern Biotech |
|  |  | Human IL-21 (interleukin-21); | PeproTech, inc. |
|  |  | Human IL-22 (interleukin-22); | PeproTech, inc. |
|  |  | Human IL-23 (interleukin-23); | PeproTech, inc. |
|  |  | Human IL-27 (interleukin-27); | Biolegend |
|  |  | Human IL-31 (interleukin-31); | PeproTech, inc. |
|  |  | Human IL-33 (interleukin-33); | PeproTech, inc. |
|  |  | Human GM-CSF (Granul.-macroph. col. stimul. factor); | PeproTech, inc. |
|  |  | Human FLT3-L (FMS-like tyrosine kinase 3 ligand); | PeproTech, inc. |

TABLE 2

| Exp. | Cond. No | Condition: (cultured 1 million cells/ml for 14 days in 96-well plates) | Total Live cells (%) | Vδ1+ T cells (%) | Fold increase of Vδ1+ T cells |
|---|---|---|---|---|---|
| 1 | 1 | 20 ng/ml IL-2 + 1 μg/ml PHA + 20 ng/ml IL-4 | 68.9 | 31.6 | 77 |
|  | 2 | 500 ng/ml IL-2 + 1 μg/ml PHA | 63.3 | 10.5 | 4 |
|  | 3 | 20 ng/ml IL-2 + 1 μg/ml PHA (control) | 68.8 | 1.90 | 1 |
| 2 | 1 | 20 ng/ml IL-2 + 1 μg/ml α-CD3 mAb + 20 ng/ml IL-4 | 90.0 | 51.7 | 75 |
|  | 2 | 20 ng/ml IL-2 + 1 μg/ml α-Vδ1 TCR mAb + 20 ng/ml IL-4 | 85.2 | 55.9 | 69 |
|  | 3 | 5 ng/ml IL-2 + 1 μg/ml PHA + 20 ng/ml IL-4 | 84.0 | 61.9 | 62 |
|  | 4 | 20 ng/ml IL-2 + 1 μg/ml PHA + 20 ng/ml IL-4 (previous best) | 72.0 | 45.3 | 27 |
|  | 5 | 100 ng/ml IL-2 + 1 μg/ml PHA + 20 ng/ml IL-4 | 71.3 | 55.7 | 22 |
|  | 6 | 300 ng/ml IL-2 + 1 μg/ml PHA + 20 ng/ml IL-4 | 71.3 | 57.0 | 21 |
| 3 | 1 | 5 ng/ml IL-15 + 1 μg/ml α-CD3 mAb + 20 ng/ml IL-4 | 91.7 | 61.4 | 138 |
|  | 2 | 5 ng/ml IL-2 + 1 μg/ml α-CD3 mAb + 20 ng/ml IL-4 | 81.4 | 59.4 | 124 |
|  | 3 | 20 ng/ml IL-2 + 1 μg/ml α-CD3 mAb + 20 ng/ml IL-4 (prev. best) | 84.2 | 45.4 | 105 |
|  | 4 | 5 ng/ml IL-15 + 1 μg/ml PHA + 20 ng/ml IL-4 | 68.0 | 76.2 | 21 |
|  | 5 | 5 ng/ml IL-2 + 1 μg/ml PHA + 20 ng/ml IL-4 | 60.1 | 69.1 | 19 |
|  | 6 | 20 ng/ml IL-15 + 1 μg/ml PHA + 20 ng/ml IL-4 | 68.6 | 69.9 | 13 |
|  | 7 | 20 ng/ml IL-2 + 1 μg/ml PHA + 20 ng/ml IL-4 | 62.9 | 67.7 | 11 |
| 4 | 1 | 20 ng/ml IFN-γ + 1 μg/ml α-CD3 mAb + 20 ng/ml IL-4 | 87.1 | 79.5 | 1 349 |
|  | 2 | 3 ng/ml IFN-γ + 1 μg/ml α-CD3 mAb + 20 ng/ml IL-4 | 85.5 | 67.4 | 1 014 |

TABLE 2-continued

| Exp. | Cond. No | Condition: (cultured 1 million cells/ml for 14 days in 96-well plates) | Total Live cells (%) | Vδ1+ T cells (%) | Fold increase of Vδ1+ T cells |
|---|---|---|---|---|---|
| | 3 | 2 ng/ml IL-15 + 1 µg/ml α-CD3 mAb + 20 ng/ml IL-4 | 87.9 | 81.6 | 909 |
| | 4 | 1 µg/ml α-CD3 mAb + 20 ng/ml IL-4 | 85.9 | 67.8 | 804 |
| | 5 | 5 ng/ml IL-15 + 1 µg/ml α-CD3 mAb + 20 ng/ml IL-4 (prev. best) | 78.9 | 69.4 | 624 |

Results of experiment no. 2 demonstrated that IL-2 (when in the presence of IL-4 and PHA) must be used at low concentrations, for increased proliferation and enrichment of Vδ1+ T cells in culture (conditions 3-7, Table 2). This effect was not observed in the previous experiment (exp. no 1), in which fold expansion was higher in the presence of PHA and high levels of IL-2, in the absence of IL-4. Furthermore, the anti-CD3 mAb was shown to be the most effective mitogen promoting survival and proliferation of Vδ1+ T cells in culture (see condition 1 versus condition 2, Table 2).

Results of experiment no 0.3 (Table 2) confirmed previous observations and showed that even lower (than previously used) concentration levels of IL-2 (in the presence of IL-4 and a T cell mitogen), promoted even higher Vδ1+ T cell proliferation, survival and enrichment in culture. Also, when used at the same concentration, IL-15 was more effective than IL-2 in promoting Vδ1+ T cell survival, enrichment and proliferation. Again, the anti-CD3 mAb was shown to be the most effective mitogen of our tests.

Results of experiment no 4 further indicated that the presence of high levels of IL-15 in the culture medium was detrimental for the proliferation of Vδ1+ T cells. Indeed, even lower (than previously used) concentration levels of IL-15 promoted even higher expansion levels of Vδ1+ T cells, when in the presence of IL-4 and α-CD3 (Conditions 3-5, Table 2). Finally, in a totally unexpected finding, the replacement of IL-15 by INF-γ (i.e., the absence of IL-15 and the presence of IFN-γ in the culture medium), was shown to generate increased expansion levels of cultured Vδ1+ T cells.

Figure 3D:
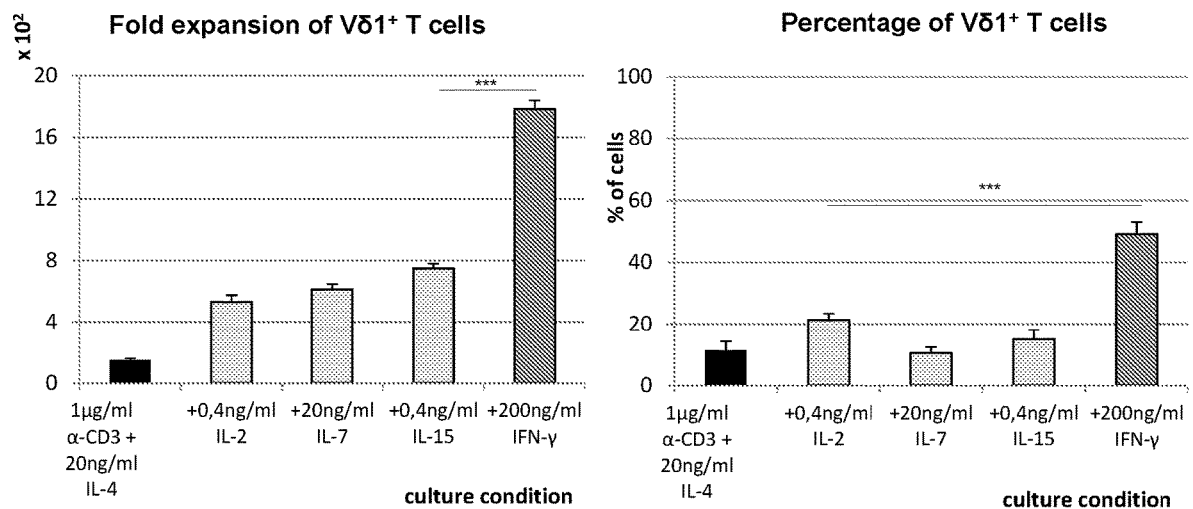

Although many different concentrations and combinations of IL-2, IL-7 and IL-15 were tested in parallel, IFN-γ was consistently found to be a much more effective reagent for promoting the selective expansion of Vδ1+ T cells in culture (when used in the presence of IL-4 and a T cell mitogen, such as anti-CD3 mAb; FIG. 3). The higher performance of IFN-γ in these cultures was independent of the concentrations of IL-4 and anti-CD3 mAb used (FIGS. 3A-C and FIG. 4). Importantly, the use of IFN-γ (but not of IL-2, IL-15 or IL-7), induced a drastic increase in the enrichment and expansion levels of Vδ1+ T cells in bulk cultures of CD3+ T cells (FIG. 3D). In these cultures, contaminating TCRαβ+ T cells present in the starting samples responded to and proliferated in the presence of IL-2, IL-15 and IL-7, but not in the presence of IFN-γ, that seems to be a more selective activator of Vδ1+ T cells. These experiments showed that the specific (and not previously described) combination of IFN-γ with IL-4 and a T cell mitogen, in the absence of IL-2, IL-7 and IL-15 for the production of Vδ1+ T cells has unique advantages that can be used in a variety of novel therapeutic and commercial applications.

IFN-γ is a dimerized soluble cytokine and is the only member of the type II class of interferons.[50] It is structurally and functionally different from common γ-chain cytokines such as IL-2, IL-4, IL-7 or IL-15 and is serologically distinct from Type I interferons: it is acid-labile, while the type I variants are acid-stable.

Although we have obtained a new and improved method for expanding and enriching populations of Vδ1+ T cells in culture, we also sought to analyze the anti-tumor function of the generated cells, in vitro. We found that the presence of IL-4 in the culture medium strongly inhibited or decreased the expression of activating receptors such as Natural Cytotoxicity Receptors (NCRs, namely NKp30 and NKp44), and NKG2D on expanded Vδ1+ T-cells (Table 3).

Activating Natural Killer (NK) receptors (such as NKp30, NKp44 and NKG2D) are known to play a critical role in the anti-tumor and anti-viral function of Vδ1+ T cells, through binding to their molecular ligands expressed on the surface of tumor or infected cells. Receptor-ligand binding triggers the production and release of granzymes and perforines by Vδ1+ T cells, leading to the death of target cells.[29] In our study, we found that the presence of IL-4 in the culture medium induced a decrease in the levels of activating NK receptors located at the surface of cultured TCRγδ+ T cells, thereby decreasing their cytotoxic function against MOLT-4 leukemia cells (Table 3). Of note, the inhibition induced by IL-4 seemed to affect all TCRγδ+ T cell subsets present in the final cellular product, including both Vδ1- and Vδ1+ TCRγδ+ T cells (Table 3).

TABLE 3

| Condition N° | Culture condition (days 1-14) | Culture condition (days 15-21) | Live cells (%) | Vδ1+ T cells (%) | Fold increase of Vδ1+ T cells | Vδ1+ NKp30+ T cells (%) | Vδ1+ NKp44+ T cells (%) | Vδ1+ NKG2D+ T cells (%) | Dead tumor target cells (%) |
|---|---|---|---|---|---|---|---|---|---|
| 1 | | 100 ng/ml IL-15 1 µg/ml a-CD3 mAb (control) | 61.4 | 50.3 | 108 | 45.0 | 38.0 | 99.8 | 62.6 |
| 2 | | 100 ng/ml IL-4 70 ng/ml IFN-γ 1 µg/ml a-CD3 mAb | 81.0 | 92.6 | 8 064 | 0.9 | 0.2 | 48.2 | 14.0 |
| 3 | | 100 ng/ml IL-4 1 µg/ml a-CD3 mAb | 83.1 | 83.1 | 2 185 | 0.1 | 0.3 | 46.4 | 17.5 |
| 4 | | 100 ng/ml IL-4 1 µg/ml a-TCRVδ1 mAb | 68.4 | 92.8 | 1 263 | 1.6 | 1.1 | 38.4 | 13.3 |

TABLE 3-continued

| Condition N° | Culture condition (days 1-14) | Culture condition (days 15-21) | Live cells (%) | Vδ1+ T cells (%) | Fold increase of Vδ1+ T cells | Vδ1+ NKp30+ T cells (%) | Vδ1+ NKp44+ T cells (%) | Vδ1+ NKG2D+ T cells (%) | Dead tumor target cells (%) |
|---|---|---|---|---|---|---|---|---|---|
| 5 | | 100 ng/ml IL-4 1 µg/ml PHA | 69.6 | 73.8 | 464 | 1.5 | 2.2 | 58.7 | 9.0 |
| 6 | 100 ng/ml IL-4 70 ng/ml IFN-γ | 100 ng/ml IL-15 1 µg/ml a-CD3 mAb | 87.3 | 85.9 | 24 152 | 30.1 | 14.7 | 98.9 | 68.5 |
| 7 | 1 µg/ml a-CD3 mAb | 100 ng/ml IL-2 1 µg/ml a-CD3 mAb | 80.1 | 88.1 | 16 374 | 29.0 | 18.2 | 99.4 | 70.2 |
| 8 | | 100 ng/ml IL-7 1 µg/ml a-CD3 mAb | 78.3 | 85.4 | 18 366 | 15.6 | 15.4 | 99.2 | 67.6 |
| 9 | 100 ng/ml IL-4 1 µg/ml a-CD3 mAb | 100 ng/ml IL-15 1 µg/ml a-CD3 mAb | 83.1 | 80.6 | 9 636 | 19.5 | 17.7 | 99.0 | 64.6 |
| 10 | | 100 ng/ml IL-2 1 µg/ml a-CD3 mAb | 84.0 | 85.5 | 7 747 | 23.0 | 12.9 | 98.4 | 54.4 |
| 11 | | 100 ng/ml IL-7 1 µg/ml a-CD3 mAb | 76.5 | 83.0 | 10 567 | 10.1 | 4.4 | 99.2 | 50.6 |
| 12 | 100 ng/ml IL-4 1 µg/ml a-Vδ1 mAb | 100 ng/ml IL-15 1 µg/ml a-Vδ1 mAb | 69.4 | 72.6 | 5 564 | 23.2 | 6.6 | 95.4 | 54.5 |
| 13 | 100 ng/ml IL-4 1 µg/ml PHA | 100 ng/ml IL-15 1 µg/ml PHA | 67.8 | 65.6 | 2 454 | 17.6 | 13.4 | 95.6 | 46.0 |

This was in line with a recent study showing that IL-4 promotes the generation of regulatory Vδ1+ T cells via IL-10 production. IL-4-treated Vδ1+ T cells secreted significantly less IFN-γ and more IL-10 relative to Vδ2+ T cells. Furthermore, Vδ1+ T cells showed relatively low levels of NKG2D expression in the presence of IL-4, suggesting that Vδ1+ T cells weaken the TCRγδ+ T cell-mediated anti-tumor immune response.[42]

Since we were looking for novel culture methods with the objective of improving the anti-tumor effector functions of Vδ1+ T cells, we attempted to recover the expression of activating NK receptors on IL-4-treated cells, also recovering the cytotoxic phenotype of these cells, something that was never tried before.

TCRγδ+ T cells were cultured in a two-step protocol. The first step consisted of treating cells in culture medium in the presence of a T cell mitogen (such as anti-CD3 mAb or PHA) and IL-4, and in the absence of IL-2, IL-15 and IL-7, to promote the selective expansion of Vδ1+ T-cells. The second culture step consisted of treating cells in a culture medium in the absence of IL-4, and in the presence of a T cell mitogen and IL-2, or IL-7 or IL-15, to promote cell differentiation, and NKR expression (Table 3 and Table 4).

Conditions 1-5 (Table 3) confirmed previous results, showing that Vδ1+ T cells cultured in the presence of IL-4 could expand in culture several thousand fold, but could not differentiate, becoming inefficient killers of tumor cells. In contrast, as seen in conditions 6-13, when cells were sub-cultured in a second culture medium in the absence of IL-4 and in the presence of a T cell mitogen and IL-2, or IL-7, or IL-15, the ability to eliminate tumor cells increased radically. The presence of each one of these three cytokines (IL-2, IL-7 and IL-15), alone or in combination, was able to revert the phenotype of cultured Vδ1+ T cells and thus can be used for this purpose.

Results of experiments no. 6 and 7 (Table 4) showed that 2-step protocols and even 3-step protocols could be more efficiently used to stimulate the proliferation and differentiation of Vδ1+ T-cells. In the case of 3-step protocols, where cells were cultured in 3 different culture media (see for example condition 2 of experiment no 7 of Table 4), it was very important to separate the IL-4 containing medium from medium containing IL-2 or IL-7 or IL-15. From these results it could also be concluded that a fraction of old culture medium should be removed during each subculture step for improved cell expansion; and that in the second culture medium, IL-15 is slightly more efficient than IL-2 in promoting Vδ1+ T-cell proliferation.

Additional experiments using 3-step and 4-step culture protocols further demonstrated that other growth factors can be added to the first and/or second culture medium (Table 3 and Table 4) for increased expansion levels of Vδ1+ T cells and expression of NK receptors on these cells. INF-γ, IL-21 and IL-1β were identified as efficient inducers of Vδ1+ T cell expansion and survival (Table 5). These growth factors could be used in the first or in the second culture media.

Finally, the addition of a soluble ligand of the CD27 receptor, or a soluble ligand of the CD7 receptor or a soluble ligand of SLAM receptor resulted in enhanced expansion of Vδ1+ T cells (Conditions 3-6 of Table 5). CD27 receptor is typically required for the generation and long-term maintenance of T cell immunity. It binds to its ligand CD70, and plays a key role in regulating B-cell activation and immunoglobulin synthesis. CD7 receptor is a member of the immunoglobulin superfamily. This protein is found on thymocytes and mature T cells. It plays an essential role in T-cell interactions and also in T-cell/B-cell interaction during early lymphoid development. SLAM receptor is a member of the signaling lymphocytic activation molecule family of immunomodulatory receptors.

TABLE 4

| Exp. | Cond. No | Condition: (cultured 5 × 10⁵ million cells/ml for 15 days in 96-well plates): | Vδ1+ T cells (%) | Fold increase of Vδ1+ T cells | Vδ1+ NKp30+ T cells (%) |
|---|---|---|---|---|---|
| 6 | 1 | Days 0-5: 100 ng/ml IL-4 + 1 µg/ml α-CD3 + 70 ng/ml IFN-γ Days 6-15: 100 ng/ml IL-15 + 2 µg/ml α-CD3 | 72.4 | 7 635 | 39.4 |

TABLE 4-continued

| Exp. | Cond. No | Condition: (cultured 5 × 10⁵ million cells/ml for 15 days in 96-well plates): | Vδ1+ T cells (%) | Fold increase of Vδ1+ T cells | Vδ1+ NKp30+ T cells (%) |
|---|---|---|---|---|---|
| | 2 | Days 0-5: 100 ng/ml IL-4 + 1 µg/ml α-CD3 + 70 ng/ml IFN-γ<br>Days 6-15: 100 ng/ml IL-7 + 2 µg/ml α-CD3 | 60.1 | 5 100 | 37.9 |
| | 3 | Days 0-5: 100 ng/ml IL-4 + 1 µg/ml α-CD3 + 70 ng/ml IFN-γ<br>Days 6-15: 100 ng/ml IL-2 + 2 µg/ml α-CD3 | 68.2 | 4 135 | 36.5 |
| 7 | 1 | Days 0-5: 100 ng/ml IL-4 + 1 µg/ml α-CD3 + 70 ng/ml IFN-γ<br>Days 6-10: 100 ng/ml IL-15 + 2 µg/ml α-CD3<br>Days 11-15: remove medium, 100 ng/ml IL-15 + 2 µg/ml α-CD3 | 65.0 | 4 468 | 45.4 |
| | 2 | Days 0-5: 30 ng/ml IL-4 + 1 µg/ml α-CD3 + 70 ng/ml IFN-γ<br>Days 6-10: 100 ng/ml IL-15 + 1 µg/ml α-CD3 + 2 ng/ml IL-21<br>Days 11-15: 100 ng/ml IL-15 + 1 µg/ml α-CD3 + 5 ng/ml IL-21 | 80.5 | 3 987 | 36.0 |
| | 3 | Days 0-5: 100 ng/ml IL-4 + 1 µg/ml α-CD3 + 70 ng/ml IFN-γ<br>Days 6-10: remove medium, 100 ng/ml IL-15 + 2 µg/ml α-CD3<br>Days 11-15: 100 ng/ml IL-15 + 2 µg/ml α-CD3 | 64.0 | 3 683 | 41.0 |

Of note, several different culture media were tested (FIG. 5). These tests have shown that the present invention works very well with different culture media, including commercially available, serum free, clinical-grade media produced by different manufacturers, and suitable for clinical applications.

viable cells initially present after MACS. However, within 11-21 days of treatment following the optimized 2-step culture method and in the presence of the described cocktail of cytokines and T cell mitogen, Vδ1+ T cells became the dominant cell subset in culture, varying between 60-80% of total cells between donors (FIG. 6). Of note, a very repro-

TABLE 5

| Condition number: | Culture condition (days 1-6) | Culture condition (days 7-11) | Culture condition (days 12-16) | Culture condition (days 17-21) | Vδ1+ T cells (%) | Fold increase of Vδ1+ T cells | Vδ1+ NKp30+ T cells (%) |
|---|---|---|---|---|---|---|---|
| 1 | 100 ng/ml IL-4<br>70 ng/ml IFN-γ<br>70 ng/ml α-CD3 mAb<br>70 ng/ml IL-21<br>15 ng/ml IL-1β | | 70 ng/ml IFN-γ<br>2 µg/ml α-CD3 mAb<br>100 ng/ml IL-15 | | 75.0 | 61 417 | 54.1 |
| 2 | 100 ng/ml IL-4<br>70 ng/ml IFN-γ<br>70 ng/ml α-CD3 mAb<br>70 ng/ml IL-21 | | 70 ng/ml IFN-γ<br>2 µg/ml α-CD3 mAb<br>100 ng/ml IL-15 | | 80.1 | 37 457 | 38.5 |
| 3 | | 100 ng/ml IL-4<br>70 ng/ml IFN-γ<br>70 ng/ml α-CD3 mAb<br>1 µg/ml sCD27L | 1 µg/ml α-CD3 mAb<br>100 ng/ml IL-15 | | 72.4 | 10 535 | 22.5 |
| 4 | | 100 ng/ml IL-4<br>70 ng/ml IFN-γ<br>70 ng/ml α-CD3 mAb<br>1 µg/ml α-SLAM mAb | | | 69.6 | 9 566 | 25.4 |
| 5 | | 100 ng/ml IL-4<br>70 ng/ml IFN-γ<br>70 ng/ml α-CD3 mAb<br>1 µg/ml sCD7L | | | 70.7 | 7 764 | 24.5 |
| 6 | | 100 ng/ml IL-4<br>70 ng/ml IFN-γ<br>70 ng/ml α-CD3 mAb | | | 72.8 | 5 594 | 21.4 |

In Vitro Characterization of Large-Scale Expanded TCRγδ+ T Cells

Having established an effective protocol for the isolation and expansion of Vδ1+ T cells in culture, we sought to test it with blood samples collected from a larger number of healthy donors and also from cancer patients. This was necessary to test the robustness and general applicability of the new culture method. Moreover, instead of plastic plates or flasks, cells were cultured in closed, large-scale, gas-permeable cell bags developed for clinical applications.

The adopted two-step method of magnetic-associated cell sorting (MACS) produced viable cell populations enriched in TCRγδ+ T cells from 8 different donors (Table 6). Vδ1+ TCRγδ+ cells comprised only about 1% to 44% of the total ducible expansion was achieved and the composition of the final cellular product was remarkably similar across multiple donors (FIG. 6, Table 7). Importantly non-Vδ1+ TCRγδ+ T cells in the final products were found to be mostly Vδ1⁻ Vδ2⁻ TCRγδ+ T cells (which comprised around 17%-37% of total cells). These cells probably consisted of Vδ3+ TCRγδ+ T cells, since this is the third most abundant TCRγδ+ T cell subset in the peripheral blood. It was possible to calculate the percentage of Vδ1⁻ Vδ2⁻ TCRγδ+ T cells in the final cellular products by subtracting the percentage of Vδ1+ T cells and Vδ2+ T cells from the percentage of total TCRγδ+ T cells (Table 7). Fold expansions in these plastic bags were, as expected, of lower magnitude than those from plates, but still generated relevant numbers for clinical translation.

The expression of activating Natural Cytotoxicity Receptors (NCRs; including NKp30 and NKp44), and NKG2D was robustly induced in long-term cultured Vδ1+ T cells, of all tested donors (Table 8 and FIG. 7). The obtained TCRγδ+ T cells (which included both Vδ1+ and Vδ1− Vδ2− cell subsets) were highly cytotoxic against CLL cells (both MEC-1 cell line and primary CLL patient samples), but did not target healthy autologous PBMCs (FIG. 8A and FIG. 8C). Preliminary experiments with the use of blocking antibodies against TCRγδ+ T cell activating receptors showed that anti-tumor cytotoxicity was partially reliant on NKG2D and NKp30 receptors (FIG. 8B). Furthermore, expanded and differentiated TCRγδ+ T cells produced high levels of the pro-inflammatory cytokine IFN-γ (FIG. 9).

Finally, Vδ2− TCRγδ+ T cells could be efficiently isolated and expanded from the PBLs of elderly CLL patients with very high tumour burden (Table 9 and Table 10 and FIG. 10A), and displayed potent anti-tumour and anti-viral activities (FIG. 10B). Of note, contaminating autologous leukemic B cells were eliminated during the in vitro culture of TCRγδ+ T cells (Table 10).

This collection of data fully demonstrates the unique ability of the invention to generate functional Vδ2− γδ T cells (namely from cancer patients) for autologous or allogeneic adoptive cell therapy. The method is robust enough to enrich (>60%) and expand (up to 2,000-fold) Vδ1+ T cells from highly unpurified samples obtained from CLL patients, differentiating them into NKR-expressing and highly cytotoxic TCRγδ+ T cells.

Importantly, preliminary tests also demonstrated in vitro reactivity of cultured TCRγδ+ T cells against tumor cells of other tissue origins (FIG. 11), suggesting that expanded and differentiated Vδ2− γδ T cells can also be used for treating these conditions.

TABLE 6

| | Cell lineage: | | | | | | | |
|---|---|---|---|---|---|---|---|---|
| Donor | B cells (CD19+ CD20+ cells) | NK cells (CD56+ CD3− cells) | T cells (CD3+ cells) | TCRαβ+ T cells (TCRαβ+ CD3+ cells) | TCRγδ+ T cells (TCRγδ+ CD3+ cells) | Vδ1+ T cells (TCRVδ1+ CD3+ cells) | Vδ2+ T cells (TCRVδ2+ CD3+ cells) | Total cell viability (Trypan Blue− cells) |
| A | 24.6 | 9.92 | 43.5 | 0.01 | 41.9 | 13.5 | 23.6 | 79.4 |
| B | 6.69 | 0.07 | 75.0 | 0.71 | 63.2 | 21.6 | 30.0 | 80.1 |
| C | 1.36 | 0.36 | 95.3 | 0.37 | 94.5 | 1.25 | 92.6 | 95.2 |
| D | 13.9 | 6.79 | 41.2 | 0.76 | 40.2 | 18.3 | 21.5 | 89.1 |
| E | 17.0 | 1.84 | 65.8 | 2.80 | 59.6 | 17.7 | 40.9 | 89.9 |
| F | 0.28 | 8.14 | 91.4 | 0.81 | 90.0 | 2.05 | 86.1 | 93.7 |
| G | 7.32 | 0.25 | 87.5 | 0.58 | 81.8 | 24.0 | 45.0 | 84.0 |
| H | 3.51 | 0.10 | 88.8 | 0.80 | 84.8 | 44.0 | 27.0 | 86.0 |

TABLE 7

| | Cell lineage: | | | | | | | |
|---|---|---|---|---|---|---|---|---|
| Donor | B cells (CD19+ CD20+ cells) | NK cells (CD56+ CD3− cells) | T cells (CD3+ cells) | TCRαβ+ T cells (TCRαβ+ CD3+ cells) | TCRγδ+ T cells (TCRγδ+ CD3+ cells) | Vδ1+ T cells (TCRVδ1+ CD3+ cells) | Vδ2+ T cells (TCRVδ2+ CD3+ cells) | Total cell viability (Trypan Blue− cells) |
| A | 0 | 0.50 | 99.5 | 0.01 | 99.3 | 82.6 | 3.9 | 89.0 |
| B | 0 | 0.02 | 99.7 | 0.06 | 99.5 | 80.8 | 3.7 | 93.3 |
| C | 0 | 0.50 | 96.3 | 0.03 | 92.8 | 69.9 | 4.2 | 90.3 |
| D | 0 | 0.03 | 99.6 | 0.02 | 99.1 | 62.2 | 2.3 | 94.5 |
| E | 0 | 0.11 | 99.5 | 0.01 | 99.2 | 63.3 | 3.3 | 95.9 |
| F | 0 | 0 | 99.9 | 0.02 | 98.0 | 73.3 | 4.3 | 93.2 |
| G | 0 | 0.10 | 99.4 | 0.01 | 98.4 | 71.7 | 3.5 | 90.0 |
| H | 0 | 0.40 | 97.5 | 0 | 98.2 | 72.0 | 1.6 | 89.0 |

TABLE 8

| Donor | Activating receptor | Day 0 | Day 16 | Day 21 |
|---|---|---|---|---|
| A | NKp30 | 0.51 | 66.8 | 65.0 |
|   | NKp44 | 0.30 | 18.3 | 23.3 |
|   | NKG2D | 46.0 | 96.5 | 98.0 |
| B | NKp30 | 0.56 | 71.6 | 68.0 |
|   | NKp44 | 0 | 37.2 | 38.7 |
|   | NKG2D | 55.0 | 90.7 | 95.1 |

TABLE 9

| | Cell lineage: | | | | | | |
|---|---|---|---|---|---|---|---|
| Donor | B cells (CD19$^+$ CD20$^+$ cells) | NK cells (CD56$^+$ CD3$^-$ cells) | T cells (CD3$^+$ cells) | TCRαβ$^+$ T cells (TCRαβ$^+$ CD3$^+$ cells) | TCRγδ$^+$ T cells (TCRγδ$^+$ CD3$^+$ cells) | Vδ1$^+$ T cells (TCRVδ1$^+$ CD3$^+$ cells) | Cell viability (Trypan Blue$^-$ cells) |
| | Before MACS (Day 0) | | | | | | |
| CLL-1 | 63.4 | 1.22 | 30.4 | 27.5 | 0.66 | 0.22 | 92.0 |
| CLL-2 | 85.7 | 0.92 | 8.35 | 6.97 | 0.43 | 0.03 | 90.0 |
| CLL-3 | 90.4 | 0.15 | 3.74 | 3.31 | 0.35 | $1.9 \times 10^{-3}$ | 87.0 |
| | After MACS (Day 0) | | | | | | |
| CLL-1 | 38.0 | 0.72 | 37.2 | 0.19 | 7.32 | 4.00 | 88.0 |
| CLL-2 | 35.4 | 0.26 | 61.3 | 0.05 | 36.7 | 1.70 | 83.0 |
| CLL-3 | 57.0 | 0.45 | 39.5 | 0.02 | 10.4 | 0.28 | 80.0 |

TABLE 10

Cell phenotype after in vitro culture (Day 21)

| | Cell lineage: | | | | | | | |
|---|---|---|---|---|---|---|---|---|
| Donor | B cells (CD19$^+$ CD20$^+$ cells) | NK cells (CD56$^+$ CD3$^-$ cells) | T cells (CD3$^+$ cells) | TCRαβ$^+$ T cells (TCRαβ$^+$ CD3$^+$ cells) | TCRγδ$^+$ T cells (TCRγδ$^+$ CD3$^+$ cells) | Vδ1$^+$ T cells (TCRVδ1$^+$ CD3$^+$ cells) | NKp30$^+$ Vδ1$^+$ T cells (pre-gated) | NKG2D$^+$ Vδ1$^+$ T cells (pre-gated) |
| CLL-1 | 0.04 | 0.11 | 96.8 | 0.08 | 94.1 | 60.1 | 23.0 | 95.6 |
| CLL-2 | 0.07 | 0.01 | 99.5 | 0.02 | 97.4 | 80.0 | 11.0 | 98.9 |
| CLL-3 | 0.05 | 0.01 | 99.8 | 0.01 | 99.6 | 70.1 | 13.4 | 97.2 |

In Vivo Studies of Expanded TCRγδ$^+$ T Cells

Having successfully developed a method to generate large numbers of functional TCRγδ$^+$ T cells, which we called "DOT-cells", we next investigated their homing and anti-leukaemia activity in vivo. We took advantage of a xenograft model of human CLL previously shown to reproduce several aspects of the disease and used to test the efficacy of other cellular therapies, including CAR-T cells.[51, 52] The model relies on the adoptive transfer of CLL/SLL-derived MEC-1 cells into Balb/c Rag$^{-/-}$ γc$^{-/-}$ (BRG) animals, which lack all lymphocytes and thus do not immediately reject the human cells. However, some myeloid lineage-mediated rejection of human xenografts still occurs. This rejection varies in its magnitude according to the mouse strain used, due to different alleles encoding for SIRP-α[53]. We have thus further adapted the model in order to characterize TCRγδ$^+$ T cells at late time points after transfer, using NOD-SCID γc$^{-/-}$ (NSG) animals as hosts. Indeed, upon transfer into tumour-bearing NSG hosts we were able to recover TCRγδ$^+$ T cells in all tissues analysed, 30 days after transfer, with a strong enrichment for CD3±Vδ1$^+$ T cells (FIG. 12). Importantly, we detected the expression of NKp30 and NKG2D in the recovered TCRγδ$^+$ T cells, demonstrating that they stably preserve their characteristics in vivo. Of note, upon transfer into BRG animals we could not recover TCRγδ$^+$ T cells at such late time points, but we observed them in both lung and liver at 72 hours after transfer (FIG. 12). These experiments confirm the better fitness of human xenografted cells in NSG animals, while allowing us to have two different models to test the anti-tumour properties of the expanded Vδ2$^-$ γδ T cells in vivo.

In order to dynamically follow tumour growth using bioluminescence, we transduced MEC-1 cells with firefly luciferase-GFP, and transferred 10$^7$ MEC-1 cells sub-cutaneously into BRG animals. After 7 days we injected luciferin i.p. to determine tumour load as a function of luminescence, before ascribing treatment (or PBS control) to the animals. We performed two transfers of TCRγδ$^+$ T cells within 5 days. We then measured tumour size as a function of time using a Caliper; importantly, we detected a clear reduction in primary tumour size in treated animals when compared to controls (FIG. 13). This reduction was significant 9 days after the second transfer of TCRγδ$^+$ T cells. This result demonstrated that TCRγδ$^+$ T cells are effective in vivo, even if a more extensive characterization of their anti-tumour properties was precluded by the short half-life of the human cells in BRG hosts. To overcome this limitation, we next performed a similar experiment using NSG animals as hosts.

Tumour progression growth was faster in NSG hosts, which seemingly prevented TCRγδ+ T cells from interfering with primary tumour growth (FIG. 14). However, in this model the tumour disseminates to various organs at late time points, and we found that TCRγδ+ T cells were strikingly capable of limiting tumour spread as documented by flow cytometry and histological analysis of an array of tissues (FIG. 14B-D). This included dissemination sites such as the bone marrow and the liver. The data obtained in the two xenograft models collectively demonstrate the in vivo efficacy of TCRγδ+ T cells to reduce primary tumour size (in BRG hosts; FIG. 13) and to control of tumour dissemination to target organs (in NSG hosts; FIG. 14).

Examination of the TCRγδ+ T cell progeny at the end of the experiment in the NSG model confirmed robust infiltration into the tumour tissue (FIG. 15A); and the stable expression of NKp30 and NKG2D on TCRγδ+ T cells (FIG. 15B). Interestingly, we detected high expression of the early activation marker CD69 specifically in tumour-infiltrating TCRγδ+ T cells, suggesting optimal activation of TCRγδ+ T cells within the tumour (FIG. 15B). Importantly, we did not observe any treatment-associated toxicity upon histological analyses (of multiple organs); or biochemical analysis of blood collected at time of necropsy (FIG. 16).

Collectively, these in vivo data provide great confidence in the safety and efficacy of the generated TCRγδ+ T cells for CLL treatment, thus inspiring their clinical application.

In conclusion, we have developed a new and robust (highly reproducible) clinical-grade method, devoid of feeder cells, for selective and large-scale expansion and differentiation of cytotoxic Vδ2− γδ T cells; and tested their therapeutic potential in pre-clinical models of chronic lymphocytic leukemia (CLL). Our cellular product, named DOT-cells, does not involve any genetic manipulation; and specifically targets leukemic but not healthy cells in vitro; and prevents wide-scale tumor dissemination to peripheral organs in vivo, without any signs of healthy tissue damage. Our results provide new means and the proof-of-principle for clinical application of DOT-cells in adoptive immunotherapy of cancer.

Supplementary Data

The following section discloses additional data generated with the use of the previously described invention. The data contained herein confirmed previous results and expanded on previous observations and should be used as supporting information for a better understanding of the subject matter.

As previously explained, the combination of interleukin-2 (IL-2) and interleukin-4 (IL-4) has been used with some success to expand Vδ1+ T cells in vitro. However, we found that the presence of IL-4 in the culture medium induced a strong downregulation of natural killer (NK) activating receptors (such as NKG2D, NKp30 and NKp44) on cultured TCRγδ+ T cells, weakening their anti-tumor responses.

Our previous results of experiments 1-4 are presented here again in more detail (see Table 11). Additional results obtained in parallel culture conditions (marked with an asterisk) are shown, for a more complete understanding of the results. It is also disclosed herein the percentage of NKp30±Vδ1+ T cells observed after cell culture with each condition. The observed downregulation of expression of NKp30 on cultured cells further confirmed that the potent inhibitory effects of IL-4 on Vδ2− γδ T cells also occurred when IL-2 was present in the culture medium (i.e., when the culture medium contained both IL-2 and IL-4). These data confirmed that the inhibitory effects of IL-4 are dominant over the activating effects of IL-2 on cultured TCRγδ+ T cells, and highlighted the importance of removing IL-4 on the second culture step.

As previously explained, although many different concentrations and combinations of IL-2, IL-7 and IL-15 were tested in parallel, IFN-γ was consistently found to be a much more effective reagent for promoting the selective expansion of Vδ1+ T cells in culture (when used in the presence of IL-4 and a T cell mitogen, such as anti-CD3 mAb). As it was previously suggested (but not formally shown), the use of IFN-γ alone was more effective (in promoting cell expansion in culture), than the combination of IFN-γ with either IL-2, IL-7 or IL-15, or than the combination of IL-2 with either IL-15 or IL-7 (Table 12). These data confirmed that IL-15, IL-2 and IL-7 have a detrimental effect on TCRγδ+ T cell expansion, when cells are cultured in the presence of IL-4 and IFN-γ.

As previously explained, fold expansions in large cell culture bags were, as expected, of lower magnitude than those from 96-well plates, but still generated relevant numbers for clinical translation. Total absolute cell numbers obtained after large-scale cell culture in clinical grade cell bags are now detailed in Table 13.

As previously explained, the cell culture protocol obtained with the previously described method is appropriate for use in clinical applications. In fact, several materials and reagents have been approved by at least one regulatory agency (such as the European Medicines Agency or the Food and Drug Administration) for use in clinical applications. The full list is detailed in Table 14.

As previously described, the 2-step method of cell isolation proposed by the described invention generates cell samples enriched in TCRγδ+ T cells that are viable and can be further cultured. FIG. 17 shows in more detail FACS-plots of TCRγδ+ PBL enrichment after two-step MACS-sorting.

As previously explained, a very reproducible expansion was achieved with the culture method of the present invention, and the composition of the final cellular product was remarkably similar across multiple donors.

For a more complete characterization of cells obtained with the previously described invention, and given the novelty of the method and resulting cellular product, we performed large-spectrum phenotyping of 332 different cell surface markers (FIG. 18). Vδ1+ T cells were compared at the beginning (day 0) and the end (day 21) of the cell culture process. We observed marked upregulation of the activation markers CD69 and CD25 and HLA-DR, as well as the costimulatory receptors CD27, CD134/OX-40 and CD150/SLAM, indicators of enhanced proliferative potential of in vitro-generated Vδ1+ T cells (compared to their baseline Vδ1+ T cell counterparts). Moreover, expanded Vδ1+ T cells increased the expression of NK cell-associated activating/cytotoxicity receptors, namely NKp30, NKp44, NKG2D, DNAM-1 and 2B4, all previously shown to be important players in tumor cell targeting. By contrast, key inhibitory and exhaustion-associated molecules such as PD-1, CTLA-4 or CD94, were expressed either at very low levels or not expressed at all, demonstrating a striking "fitness" of expanded and differentiated TCRγδ+ T cells even after 21 days of culture under stimulatory conditions. Notably, the upregulation of multiple molecules involved in cell adhesion (e.g., CD56, CD96, CD172a/SIRPα, Integrin-β7 and ICAM-1) and chemokine receptors (CD183/CXCR3, CD196/CCR6, and CX3CR1) suggested high potential to migrate and recirculate between blood and tissues. Of note, IL-18Rα and Notch1, which are known to promote type 1

Figure 18B:
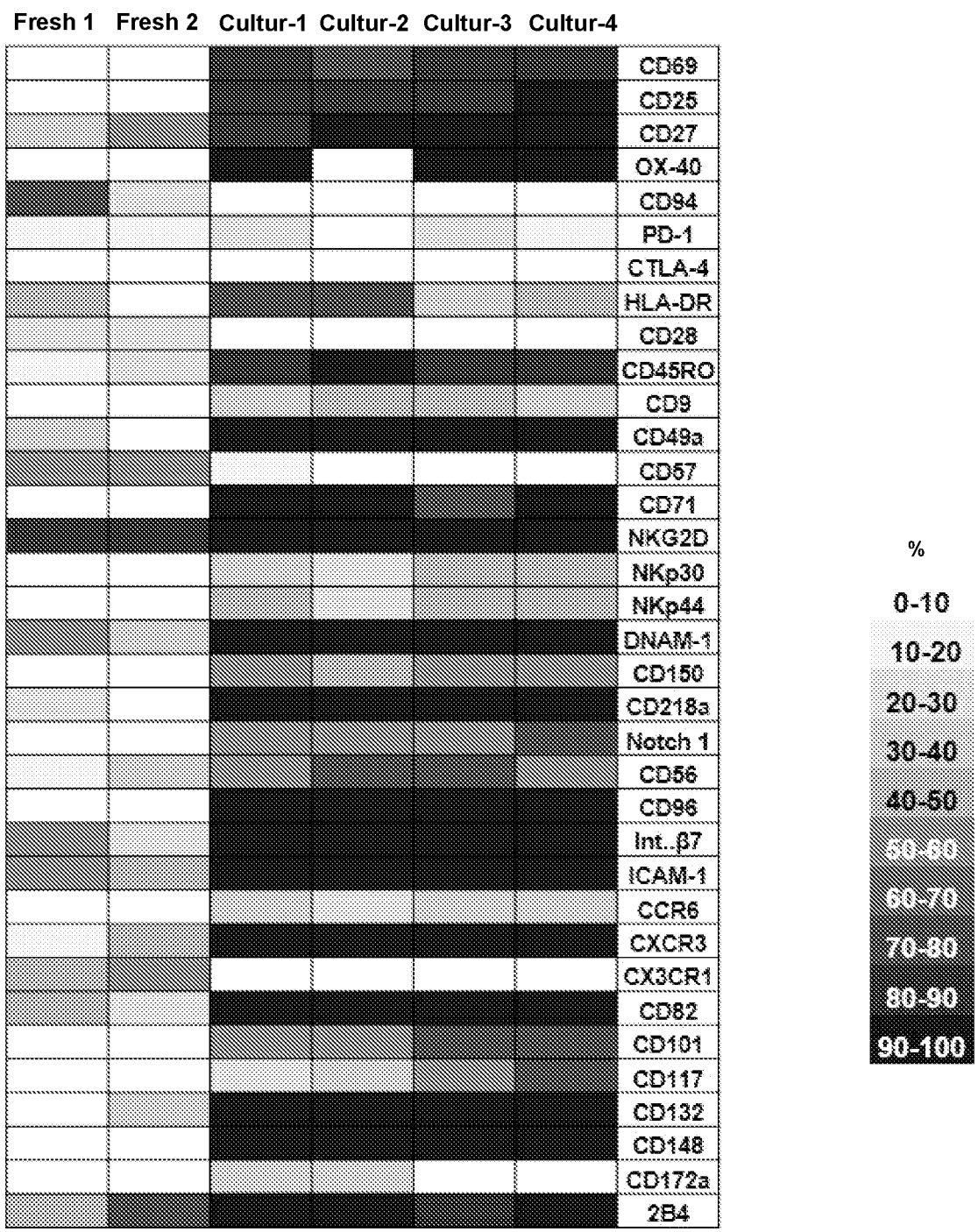

(interferon-γ-producing) responses, were also highly expressed by expanded and differentiated TCRγδ+ T cells. Importantly, in support of the robustness of our method, we found strikingly similar cell phenotypes across all 4 tested donors, as illustrated by the heatmap (FIG. 18B). These data collectively characterize expanded and differentiated TCRγδ+ T cells as a highly reproducible cellular product of activated (non-exhausted) lymphocytes endowed with migratory potential and natural cytotoxicity machinery.

As previously explained, preliminary experiments with the use of blocking antibodies against activating receptors expressed on TCRγδ+ T cells showed that anti-tumor cytotoxicity was partially reliant on NKG2D and NKp30 receptors expressed by the expanded TCRγδ+ T cells. Additional experiments presented herein also revealed a role for the γδTCR in tumor cell recognition (FIG. 19).

As previously explained, the expression of activating Natural Cytotoxicity Receptors (NCRs; including NKp30 and NKp44), and NKG2D was robustly induced in long-term cultured Vδ1+ T cells. Here we show that the same effect was observed in the Vδ1− Vδ2− cell subset. When we applied a gate (in FACS plot analysis) to the expanded (and differentiated) CD3±Vδ1− Vδ2− cell subset in the same cultures, we observed that these cells expressed around the same levels of NCRs as expressed by differentiated Vδ1+ cells (FIG. 20). These data further confirmed that the 2-step protocol described in the present invention can expand and differentiate both Vδ1+ and Vδ1− Vδ2− TCRγδ+ T cell subsets. In the first culture step, in the presence of a T cell mitogen and IL-4 (and in the absence of IL-15, IL-2 or IL-7), both Vδ1+ and Vδ1− Vδ2− TCRγδ+ T cell subsets expanded in culture, but could not differentiate towards a cytotoxic phenotype. When the obtained cells were subcultured in a second culture medium in the presence of a T cell mitogen and IL-2, or IL-7, or IL-15 (and in the absence of IL-4), both cell subsets differentiated expressing high levels of activating NK receptors that, in turn, mediated the killing of tumor cells.

As previously explained, expanded and differentiated Vδ1+ cells obtained with the method of the present invention were highly cytotoxic against leukemia cells in vitro. Here we show in more detail that the expanded and differentiated Vδ1− Vδ2− cell subset is also highly cytotoxic against tumor targets. We sorted CD3±Vδ1+ cells and CD3±Vδ1− Vδ2− cells from the same cultured cell samples by flow cytometry and co-cultured each subset with target tumor cells, in vitro. We observed that both subsets could efficiently eliminate target cells. (FIG. 21).

TABLE 11

| Exp. | Cond. No | Condition: (cultured 1 million cells/ml for 14 days in 96-well plates) | Vδ1+ T cells (%) | Fold increase of Vδ1+ T cells | NKp30+ Vδ1+ T cells (%) |
|---|---|---|---|---|---|
| 1 | 1 | 20 ng/ml IL-2 + 1 µg/ml PHA + 20 ng/ml IL-4 | 31.6 | 77 | 0.5 |
|  | 2* | 20 ng/ml IL-2 + 1 µg/ml α-Vδ1 TCR mAb | 4.7 | 8 | 6.2 |
|  | 3 | 500 ng/ml IL-2 + 1 µg/ml PHA | 10.5 | 4 | 13.4 |
|  | 4* | 20 ng/ml IL-2 + 1 µg/ml α-CD3 mAb | 5.3 | 2 | 9.1 |
|  | 5 | 20 ng/ml IL-2 + 1 µg/ml PHA (control) | 1.9 | 1 | 10.6 |
| 2 | 1 | 20 ng/ml IL-2 + 1 µg/ml α-CD3 mAb + 20 ng/ml IL-4 | 51.7 | 75 | 0.0 |
|  | 2 | 20 ng/ml IL-2 + 1 µg/ml α-Vδ1 TCR mAb + 20 ng/ml IL-4 | 55.9 | 69 | 0.2 |
|  | 3 | 5 ng/ml IL-2 + 1 µg/ml PHA + 20 ng/ml IL-4 | 61.9 | 62 | 0.0 |
|  | 4* | 1 µg/ml PHA + 20 ng/ml IL-4 | 79.6 | 38 | 0.3 |
|  | 5 | 20 ng/ml IL-2 + 1 µg/ml PHA + 20 ng/ml IL-4 (previous best) | 45.3 | 27 | 0.2 |
|  | 6 | 100 ng/ml IL-2 + 1 µg/ml PHA + 20 ng/ml IL-4 | 55.7 | 22 | 0.4 |
|  | 7 | 300 ng/ml IL-2 + 1 µg/ml PHA + 20 ng/ml IL-4 | 57.0 | 21 | 1.6 |
|  | 8* | 20 ng/ml IL-2 + 20 ng/ml IL-4 | 2.4 | 2 | 0.0 |
| 3 | 1 | 5 ng/ml IL-15 + 1 µg/ml α-CD3 mAb + 20 ng/ml IL-4 | 61.4 | 138 | 0.3 |
|  | 2 | 5 ng/ml IL-2 + 1 µg/ml α-CD3 mAb + 20 ng/ml IL-4 | 59.4 | 124 | 1.2 |
|  | 3 | 20 ng/ml IL-2 + 1 µg/ml α-CD3 mAb + 20 ng/ml IL-4 (prev. best) | 45.4 | 105 | 1.0 |
|  | 4 | 5 ng/ml IL-15 + 1 µg/ml PHA + 20 ng/ml IL-4 | 76.2 | 21 | 1.2 |
|  | 5 | 5 ng/ml IL-2 + 1 µg/ml PHA + 20 ng/ml IL-4 | 69.1 | 19 | 1.6 |
|  | 6 | 20 ng/ml IL-15 + 1 µg/ml PHA + 20 ng/ml IL-4 | 69.9 | 13 | 1.3 |
|  | 7 | 20 ng/ml IL-2 + 1 µg/ml PHA + 20 ng/ml IL-4 | 67.7 | 11 | 1.0 |
| 4 | 1 | 20 ng/ml IFN-γ + 1 µg/ml α-CD3 mAb + 20 ng/ml IL-4 | 79.5 | 1 349 | 0.8 |
|  | 2 | 3 ng/ml IFN-γ + 1 µg/ml α-CD3 mAb + 20 ng/ml IL-4 | 67.4 | 1 014 | 0.4 |
|  | 3 | 2 ng/ml IL-15 + 1 µg/ml α-CD3 mAb + 20 ng/ml IL-4 | 81.6 | 909 | 1.8 |
|  | 4 | 5 ng/ml IL-15 + 1 µg/ml α-CD3 mAb + 20 ng/ml IL-4 (prev. best) | 69.4 | 624 | 1.9 |

TABLE 12

| Cond. No | Condition: (cultured 1 million cells/ml for 14 days in 96-well plates) | Total Live cells (%) | Vδ1+ T cells (%) | Fold increase of Vδ1+ T cells |
|---|---|---|---|---|
| 1 | 20 ng/ml IFN-γ + 1 µg/ml α-CD3 mAb + 100 ng/ml IL-4 | 85.9 | 80.1 | 12 166 |
| 2 | 7 ng/ml IFN-γ + 1 µg/ml α-CD3 mAb + 100 ng/ml IL-4 | 89.9 | 93.0 | 10 757 |
| 3 | 3 ng/ml IFN-γ + 1 µg/ml α-CD3 mAb + 100 ng/ml IL-4 | 87.3 | 75.2 | 9 394 |
| 4 | 0.3 ng/ml IL-15 + 2 ng/ml IFN-γ + 1 µg/ml α-CD3 mAb + 100 ng/ml IL-4 | 77.1 | 59.7 | 4 361 |
| 5 | 2 ng/ml IL-15 + 2 ng/ml IFN-γ + 1 µg/ml α-CD3 mAb + 100 ng/ml IL-4 | 90.0 | 67.0 | 811 |
| 6 | 0.3 ng/ml IL-15 + 1 µg/ml α-CD3 mAb + 100 ng/ml IL-4 | 89.7 | 75.5 | 614 |
| 7 | 7 ng/ml IFN-γ + 1 µg/ml α-CD3 mAb + 60 ng/ml IL-4 | 85.7 | 83.2 | 10 083 |
| 8 | 2 ng/ml IL-2 + 2 ng/ml IL-15 + 1 µg/ml α-CD3 mAb + 60 ng/ml IL-4 | 87.5 | 59.4 | 7 208 |

TABLE 12-continued

| Cond. No | Condition: (cultured 1 million cells/ml for 14 days in 96-well plates) | Total Live cells (%) | Vδ1+ T cells (%) | Fold increase of Vδ1+ T cells |
|---|---|---|---|---|
| 9 | 2 ng/ml IL-2 + 7 ng/ml IFN-γ + 1 µg/ml α-CD3 mAb + 60 ng/ml IL-4 | 80.4 | 71.6 | 7 151 |
| 10 | 7 ng/ml IL-7 + 2 ng/ml IL-15 + 1 µg/ml α-CD3 mAb + 60 ng/ml IL-4 | 91.1 | 65.6 | 6 193 |
| 11 | 2 ng/ml IL-2 + 1 µg/ml α-CD3 mAb + 60 ng/ml IL-4 | 88.7 | 70.5 | 5 192 |
| 12 | 1 µg/ml α-CD3 mAb + 60 ng/ml IL-4 | 89.0 | 68.3 | 1 890 |
| 13 | 0.3 ng/ml IFN-γ + 2 µg/ml α-CD3 mAb + 100 ng/ml IL-4 | 82.7 | 59.9 | 6 139 |
| 14 | 2 ng/ml IL-7 + 0.3 ng/ml IFN-γ + 2 µg/ml α-CD3 mAb + 100 ng/ml IL-4 | 87.6 | 72.9 | 5 290 |
| 15 | 0.3 ng/ml IL-15 + 0.3 ng/ml IFN-γ + 2 µg/ml α-CD3 mAb + 100 ng/ml IL-4 | 85.9 | 80.1 | 4 840 |
| 16 | 0.3 ng/ml IL-15 + 2 µg/ml α-CD3 mAb + 100 ng/ml IL-4 | 90.0 | 64.2 | 2 943 |
| 17 | 2 µg/ml α-CD3 mAb + 100 ng/ml IL-4 | 85.8 | 73.0 | 1 826 |

TABLE 13

| | Total live cells generated from 1 Buffy Coat unit: (millions of cells) | |
|---|---|---|
| Donor: | Day 0 | Day 21 |
| A | 2.4 | 968.0 |
| B | 4.8 | 1 004.0 |
| C | 83.3 | 440.0 |
| D | 5.7 | 1 152.0 |
| E | 9.2 | 1 024.0 |
| F | 25.0 | 1 564.0 |
| G | 4.0 | 1 604.0 |
| H | 2.0 | 1 276.0 |

TABLE 14

| Reagent/Material | Manufacturer | Product reference | Manufacturing quality system* |
|---|---|---|---|
| For magnetic depletion of TCRα/β+ cells: | | | |
| CliniMACS ® Plus Instrument | Miltenyi Biotec, GmbH | 151-01 | cGMP, ISO 13485 compliant |
| CliniMACS ® TCRα/β Kit | | 200-070-407 | |
| CliniMACS ® Depletion Tubing Set | | 261-01 | |
| CliniMACS ® PBS/EDTA Buffer | | 700-25 | |
| For magnetic enrichment of CD3+ cells: | | | |
| CliniMACS ® CD3 reagent | Miltenyi Biotec, GmbH | 273-01 | cGMP, ISO 13485 compliant |
| CliniMACS ® Tubing Set TS | | 161-01 | |
| For cell culture: | | | |
| Cell culture cassettes | Saint-Gobain | CC-0500 | cGMP, 21 CFR 820 compliant |
| Clamps | Saint-Gobain | 1C-0022 | |
| VueLife ® cell culture FEP bag | Saint-Gobain | 750-C1 | |
| OpTmizer ™ T-cell expansion medium | Thermo Fisher Scientific | A10485-01 | cGMP, ISO 13485: 2003 or ISO 9001: 2008 compliant |
| L-Glutamine | Thermo Fisher Scientific | 25030-032 | |
| Human anti-CD3 mAb (clone OKT-3) | Miltenyi Biotec, GmbH | 170-076-116 | |
| Recombinant Human IL-4 | CellGenix GmbH | 1003-050 | |
| Recombinant Human IL-21 | CellGenix GmbH | 1019-050 | |
| Recombinant Human IFN-γ | R&D Systems | 285-GMP | |
| Recombinant Human IL-1β | CellGenix GmbH | 1011-050 | |
| Recombinant Human IL-15 | CellGenix GmbH | 1013-050 | |

*Note:
Some products are sold as certified medical devices for use in the EU and/or US. All other products are sold for the manufacturing of cell-based products for clinical research. They can be used in clinical trials under Investigational New Drug (IND) or Investigational Device Exemption (IDE) applications.

FULL CITATIONS FOR REFERENCES REFERRED TO IN THE SPECIFICATION

1. Hayday A C. Gammadelta T cells and the lymphoid stress-surveillance response. *Immunity* 2009; 31(2): 184-96.
2. Pang D J, Neves J F, Sumaria N, Pennington D J. Understanding the complexity of gammadelta T-cell subsets in mouse and human. *Immunology* 2012; 136(3): 283-90.
3. Deniger D C, Maiti S, Mi T, et al. Activating and propagating polyclonal gamma delta T cells with broad specificity for malignancies. *Clin Cancer Res* 2014.
4. Halary F, Pitard V, Dlubek D, et al. Shared reactivity of V{delta}2(neg) {gamma}{delta} T cells against cytomegalovirus-infected cells and tumor intestinal epithelial cells. *J Exp Med* 2005; 201(10): 1567-78.
5. Bennouna J, Bompas E, Neidhardt E M, et al. Phase-I study of Innacell gammadelta, an autologous cell-therapy product highly enriched in gamma9delta2 T lymphocytes, in combination with IL-2, in patients with metastatic renal cell carcinoma. *Cancer Immunol Immunother* 2008; 57(11): 1599-609.
6. Fisher J P, Heuijerjans J, Yan M, Gustafsson K, Anderson J. gammadelta T cells for cancer immunotherapy: A systematic review of clinical trials. *Oncoimmunology* 2014; 3(1): e27572.
7. Dieli F, Vermijlen D, Fulfaro F, et al. Targeting human {gamma}delta T cells with zoledronate and interleukin-2 for immunotherapy of hormone-refractory prostate cancer. *Cancer Res* 2007; 67(15): 7450-7.
8. Gomes A Q, Martins D S, Silva-Santos B. Targeting gammadelta T lymphocytes for cancer immunotherapy: from novel mechanistic insight to clinical application. *Cancer Res* 2010; 70(24): 10024-7.
9. Zocchi M R, Ferrarini M, Migone N, Casorati G. T-cell receptor V delta gene usage by tumour reactive gamma delta T lymphocytes infiltrating human lung cancer. *Immunology* 1994; 81(2): 234-9.
10. Maeurer M J, Martin D, Walter W, et al. Human intestinal Vdelta1+ lymphocytes recognize tumor cells of epithelial origin. *J Exp Med* 1996; 183(4): 1681-96.
11. Choudhary A, Davodeau F, Moreau A, Peyrat M A, Bonneville M, Jotereau F. Selective lysis of autologous tumor cells by recurrent gamma delta tumor-infiltrating lymphocytes from renal carcinoma. *J Immunol* 1995; 154(8): 3932-40.
12. Cordova A, Toia F, La Mendola C, et al. Characterization of human gammadelta T lymphocytes infiltrating primary malignant melanomas. *PLoS One* 2012; 7(11): e49878.
13. Donia M, Ellebaek E, Andersen M H, Straten P T, Svane I M. Analysis of Vdelta1 T cells in clinical grade melanoma-infiltrating lymphocytes. *Oncoimmunology* 2012; 1(8): 1297-304.
14. Godder K T, Henslee-Downey P J, Mehta J, et al. Long term disease-free survival in acute leukemia patients recovering with increased gammadelta T cells after partially mismatched related donor bone marrow transplantation. *Bone Marrow Transplant* 2007; 39(12): 751-7.
15. Lamb L S, Jr., Henslee-Downey P J, Parrish R S, et al. Increased frequency of TCR gamma delta+T cells in disease-free survivors following T cell-depleted, partially mismatched, related donor bone marrow transplantation for leukemia. *J Hematother* 1996; 5(5): 503-9.
16. Catellani S, Poggi A, Bruzzone A, et al. Expansion of Vdelta1 T lymphocytes producing IL-4 in low-grade non-Hodgkin lymphomas expressing UL-16-binding proteins. *Blood* 2007; 109(5): 2078-85.
17. Bartkowiak J, Kulczyck-Wojdala D, Blonski J Z, Robak T. Molecular diversity of gammadelta T cells in peripheral blood from patients with B-cell chronic lymphocytic leukaemia. *Neoplasma* 2002; 49(2): 86-90.
18. Poggi A, Venturino C, Catellani S, et al. Vdelta1 T lymphocytes from B-CLL patients recognize ULBP3 expressed on leukemic B cells and up-regulated by trans-retinoic acid. *Cancer Res* 2004; 64(24): 9172-9.
19. De Maria A, Ferrazin A, Ferrini S, Ciccone E, Terragna A, Moretta L. Selective increase of a subset of T cell receptor gamma delta T lymphocytes in the peripheral blood of patients with human immunodeficiency virus type 1 infection. *The Journal of infectious diseases* 1992; 165(5): 917-9.
20. Hviid L, Kurtzhals J A, Adabayeri V, et al. Perturbation and proinflammatory type activation of V delta1(+) gamma delta T cells in African children with *Plasmodium falciparum* malaria. *Infection and immunity* 2001; 69(5): 3190-6.
21. Dechanet J, Merville P, Lim A, et al. Implication of gammadelta T cells in the human immune response to cytomegalovirus. *J Clin Invest* 1999; 103(10): 1437-49.
22. Siegers G M, Lamb L S, Jr. Cytotoxic and regulatory properties of circulating Vdelta1+ gammadelta T cells: a new player on the cell therapy field? *Molecular therapy: the journal of the American Society of Gene Therapy* 2014; 22(8): 1416-22.
23. Meeh P F, King M, O'Brien R L, et al. Characterization of the gammadelta T cell response to acute leukemia. *Cancer Immunol Immunother* 2006; 55(9): 1072-80.
24. Knight A, Mackinnon S, Lowdell M W. Human Vdelta1 gamma-delta T cells exert potent specific cytotoxicity against primary multiple myeloma cells. *Cytotherapy* 2012.
25. Merims S, Dokouhaki P, Joe B, Zhang L. Human Vdelta1-T cells regulate immune responses by targeting autologous immature dendritic cells. *Hum Immunol* 2011; 72(1): 32-6.
26. Wu D, Wu P, Wu X, et al. expanded human circulating Vdelta1 gammadeltaT cells exhibit favorable therapeutic potential for colon cancer. *Oncoimmunology* 2015; 4(3): e992749.
27. Siegers G M, Dhamko H, Wang X H, et al. Human Vdelta1 gammadelta T cells expanded from peripheral blood exhibit specific cytotoxicity against B-cell chronic lymphocytic leukemia-derived cells. *Cytotherapy* 2011; 13(6): 753-64.
28. Siegers G M, Ribot E J, Keating A, Foster P J. Extensive expansion of primary human gamma delta T cells generates cytotoxic effector memory cells that can be labeled with Feraheme for cellular MRI. Cancer *Immunol Immunother* 2012.
29. Correia D V, Fogli M, Hudspeth K, da Silva M G, Mavilio D, Silva-Santos B. Differentiation of human peripheral blood Vdelta1+ T cells expressing the natural cytotoxicity receptor NKp30 for recognition of lymphoid leukemia cells. *Blood* 2011; 118(4): 992-1001.
30. Mangan B A, Dunne M R, O'Reilly V P, et al. Cutting edge: CD1d restriction and Th1/Th2/Th17 cytokine secretion by human Vdelta3 T cells. *J Immunol* 2013; 191(1): 30-4.
31. Kabelitz D, Hinz T, Dobmeyer T, et al. Clonal expansion of Vgamma3/Vdelta3-expressing gammadelta T cells in an HIV-½-negative patient with CD4 T-cell deficiency. *Br J Haematol* 1997; 96(2): 266-71.
32. Kenna T, Golden-Mason L, Norris S, Hegarty J E, O'Farrelly C, Doherty D G. Distinct subpopulations of gamma delta T cells are present in normal and tumor-bearing human liver. *Clin Immunol* 2004; 113(1): 56-63.
33. Zhou J, Kang N, Cui L, Ba D, He W. Anti-gammadelta TCR antibody-expanded gammadelta T cells: a better choice for the adoptive immunotherapy of lymphoid malignancies. *Cellular & molecular immunology* 2012; 9(1): 34-44.
34. Lopez R D, Xu S, Guo B, Negrin R S, Waller E K. CD2-mediated IL-12-dependent signals render human gamma delta-T cells resistant to mitogen-induced apoptosis, permitting the large-scale ex vivo expansion of functionally distinct lymphocytes: implications for the development of adoptive immunotherapy strategies. *Blood* 2000; 96(12): 3827-37.
35. Fisher J P, Yan M, Heuijerjans J, et al. Neuroblastoma killing properties of Vdelta1 and Vdelta1-negative gammadeltaT cells following expansion by artificial antigen-presenting cells. *Clin Cancer Res* 2014; 20(22): 5720-32.
36. Fisher J, Kramer A M, Gustafsson K, Anderson J. Non-V delta 2 gamma delta T lymphocytes as effectors of cancer immunotherapy. *Oncoimmunology* 2015; 4(3): e973808.
37. Deniger D C, Maiti S N, Mi T, et al. Activating and propagating polyclonal gamma delta T cells with broad specificity for malignancies. *Clin Cancer Res* 2014; 20(22): 5708-19.
38. Siegers G M, Felizardo T C, Mathieson A M, et al. Anti-leukemia activity of in vitro-expanded human gamma delta T cells in a xenogeneic Ph+ leukemia model. *PLoS One* 2011; 6(2): e16700.
39. Wilhelm M, Kunzmann V, Eckstein S, et al. Gammadelta T cells for immune therapy of patients with lymphoid malignancies. *Blood* 2003; 102(1): 200-6.
40. von Lilienfeld-Toal M, Nattermann J, Feldmann G, et al. Activated gammadelta T cells express the natural cytotoxicity receptor natural killer p 44 and show cytotoxic activity against myeloma cells. *Clin Exp Immunol* 2006; 144(3): 528-33.
41. Deniger D C, Moyes J S, Cooper U. Clinical applications of gamma delta T cells with multivalent immunity. *Front Immunol* 2014; 5: 636.
42. Mao Y, Yin S, Zhang J, et al. A new effect of IL-4 on human gammadelta T cells: promoting regulatory Vdelta1 T cells via IL-10 production and inhibiting function of Vdelta2 T cells. *Cellular & molecular immunology* 2015.
43. Silva-Santos B, Serre K, Norell H. gammadelta T cells in cancer. *Nat Rev Immunol* 2015; 15(11): 683-91.
44. Wu P, Wu D, Ni C, et al. gammadeltaT17 cells promote the accumulation and expansion of myeloid-derived suppressor cells in human colorectal cancer. *Immunity* 2014; 40(5): 785-800.
45. Mao Y, Yin S, Zhang J, et al. A new effect of IL-4 on human gammadelta T cells: promoting regulatory Vdelta1 T cells via IL-10 production and inhibiting function of Vdelta2 T cells. *Cellular & molecular immunology* 2016; 13(2): 217-28.
46. Stacchini A, Aragno M, Vallario A, et al. MEC1 and MEC2: two new cell lines derived from B-chronic lymphocytic leukaemia in prolymphocytoid transformation. *Leukemia research* 1999; 23(2): 127-36.
47. Traggiai E, Chicha L, Mazzucchelli L, et al. Development of a human adaptive immune system in cord blood cell-transplanted mice. *Science* 2004; 304(5667): 104-7.
48. Shultz L D, Lyons B L, Burzenski L M, et al. Human lymphoid and myeloid cell development in NOD/LtSz-scid IL2R gamma null mice engrafted with mobilized human hemopoietic stem cells. *J Immunol* 2005; 174(10): 6477-89.
49. Tomayko M M, Reynolds C P. Determination of subcutaneous tumor size in athymic (nude) mice. *Cancer chemotherapy and pharmacology* 1989; 24(3): 148-54.
50. Gray P W, Goeddel D V. Structure of the human immune interferon gene. *Nature* 1982; 298(5877): 859-63.
51. Bertilaccio M T, Scielzo C, Simonetti G, et al. A novel Rag2−/−gammac−/−-xenograft model of human CLL. *Blood* 2010; 115(8): 1605-9.
52. Giordano Attianese G M, Marin V, Hoyos V, et al. In vitro and in vivo model of a novel immunotherapy approach for chronic lymphocytic leukemia by anti-CD23 chimeric antigen receptor. *Blood* 2011; 117(18): 4736-45.
53. Takenaka K, Prasolava T K, Wang J C, et al. Polymorphism in Sirpa modulates engraftment of human hematopoietic stem cells. *Nat Immunol* 2007; 8(12): 1313-23.

We claim:
1. A method for expanding Vδ2⁻ TCRγδ⁺ T cells in a sample comprising:
   (1) culturing cells in the sample in a first culture medium comprising a T cell mitogen and interleukin-4; in the absence of interleukin-15, interleukin-2, or interleukin-7; and
   (2) culturing the cells obtained in step (1) in a second culture medium comprising a T cell mitogen and interleukin-15, interleukin-2, or interleukin-7, in the absence of interleukin-4.
2. A method according to claim 1 wherein the first or second culture medium, or both culture media, further comprise a second growth factor.
3. A method according to claim 2 wherein said growth factor is interferon-γ or a mimetic or functional equivalent thereof.
4. A method according to claim 1 wherein the first or second culture medium, or both culture media, further comprise a second and a third growth factors.
5. A method according to claim 4 wherein said growth factors are interferon-γ and interleukin-21 or a mimetic or functional equivalent thereof.
6. A method according to claim 1 wherein the first or second culture medium, or both culture media, further comprise a second, a third and a fourth growth factor.
7. A method according to claim 6 wherein said growth factors are interferon-γ, interleukin-21 and interleukin-1β or a mimetic or functional equivalent thereof.
8. A method according to claim 1 wherein the first and second culture media further contain serum or plasma.
9. A method according to claim 8 wherein the serum or plasma is present in an amount from about 0.5 to about 25% by volume.
10. A method according to claim 1 wherein prior to step (1) the cells in the sample are enriched for T cells; enriched for TCRγδ⁺ T cells; depleted of TCRαβ⁺ T cells; first depleted of TCRαβ⁺ T cells, and then enriched for CD3⁺ cells; or depleted of non-TCRγδ⁺ T cells.
11. A method according to claim 1 wherein the sample is blood or tissue or fractions thereof.
12. A method according to claim 11 wherein the sample is selected from peripheral blood, umbilical cord blood, lymphoid tissue, epithelia, thymus, bone marrow, spleen, liver, cancerous tissue, infected tissue, lymph node tissue or fractions thereof.
13. A method according to claim 1 wherein the sample consists of low density mononuclear cells (LDMCs) or peripheral blood mononuclear cells (PBMCs).
14. A method according to claim 1 wherein in the first culture medium the T cell mitogen is present in an amount from about 10 to about 5000 ng/ml and interleukin-4 is present in an amount from about 1 to about 1000 ng/ml.
15. A method according to claim 1 wherein in the second culture medium the T cell mitogen is present in an amount from about 0.1 to about 50 µg/ml and interleukin-15 is present in an amount from about 1 to about 1000 ng/ml.
16. A method according to claim 7 wherein in the first or second culture medium, or in both culture media, having interferon-γ is present in an amount from about 1 to about 1000 ng/ml; and interleukin-21 and interleukin 1β are present in an amount from 1 to about 500 ng/ml.
17. A method according to claim 1, wherein the T cell mitogen is an antibody or a fragment thereof.
18. A method according to claim 17 wherein the antibody binds to CD3 or a fragment thereof.

* * * * *